US007439063B2

(12) United States Patent
Digicaylioglu et al.

(10) Patent No.: US 7,439,063 B2
(45) Date of Patent: Oct. 21, 2008

(54) NEUROPROTECTIVE SYNERGY OF ERYTHROPOIETIN AND INSULIN-LIKE GROWTH FACTORS

(75) Inventors: Murat Digicaylioglu, San Diego, CA (US); Stuart A. Lipton, Rancho Santa Fe, CA (US)

(73) Assignees: Burnham Institute for Medical Research, La Jolla, CA (US); Brigham and Women's Hospital, Inc., Boston, MA (US)

( * ) Notice: Subject to any disclaimer, the term of this patent is extended or adjusted under 35 U.S.C. 154(b) by 628 days.

(21) Appl. No.: 10/460,550

(22) Filed: Jun. 11, 2003

(65) Prior Publication Data

US 2004/0092444 A1    May 13, 2004
US 2005/0197284 A9    Sep. 8, 2005

Related U.S. Application Data

(60) Provisional application No. 60/458,145, filed on Mar. 26, 2003, provisional application No. 60/388,058, filed on Jun. 11, 2002.

(51) Int. Cl.
*C12N 1/00* (2006.01)
*C12N 5/00* (2006.01)
*C07K 14/65* (2006.01)
*C07K 14/505* (2006.01)

(52) U.S. Cl. .................. 435/375; 435/325; 530/350; 530/397; 530/399

(58) Field of Classification Search .................. None
See application file for complete search history.

(56) References Cited

U.S. PATENT DOCUMENTS

| | | | |
|---|---|---|---|
| 4,745,179 A | 5/1988 | Ueda et al. | 530/350 |
| 4,876,242 A | 10/1989 | Applebaum et al. | 514/3 |
| 5,164,370 A | 11/1992 | Ballard et al. | 514/12 |
| 5,470,828 A | 11/1995 | Ballard et al. | 514/12 |
| 5,578,324 A | 11/1996 | Dohi et al. | 424/499 |
| 5,622,932 A | 4/1997 | DiMarchi et al. | 514/12 |
| 5,624,898 A | 4/1997 | Frey, II | |
| 5,652,214 A | 7/1997 | Lewis et al. | |
| 5,750,376 A | 5/1998 | Weiss et al. | |
| 5,767,078 A | 6/1998 | Johnson et al. | |
| 5,837,675 A | 11/1998 | Brox | 514/8 |
| 5,885,962 A | 3/1999 | Lu | |
| 6,153,407 A * | 11/2000 | Sytkowski et al. | 435/69.4 |
| 6,165,783 A | 12/2000 | Weiss et al. | |
| 6,180,603 B1 | 1/2001 | Frey, II | |
| 6,201,072 B1 | 3/2001 | Rathi et al. | 525/415 |
| 6,251,865 B1 | 6/2001 | Clark et al. | 514/15 |
| 6,313,093 B1 | 11/2001 | Frey, II | |
| 6,342,478 B1 | 1/2002 | Frey, II | |
| 6,407,061 B1 | 6/2002 | Frey, II | |
| 6,464,959 B1 | 10/2002 | Cutie et al. | 424/45 |
| 6,531,121 B2 | 3/2003 | Brines et al. | 424/85.1 |
| 6,908,902 B2 * | 6/2005 | Plata-Salaman et al. | 514/23 |
| 7,041,794 B2 * | 5/2006 | Escary | 530/350 |

FOREIGN PATENT DOCUMENTS

DE    19857609 A1 *    6/2000

OTHER PUBLICATIONS

Loddick et al. Neuroprotective effects of insulin-like growth factor (IGF)-I and IGF-binding protein ligand inhibitors:Novel strategies for the treatment of stroke. Pharmacology of cerebral ischemia 1998, International symposium on pharmacology of cerebral ischemia, pp. 349-354 (7th Markburg Jul. 27-29, 1998).*
Ikegaya et al., Regionally selective neurotoxicity of NMDA and colchicine is independent of hippocampal neural circuity. Neuroscience, vol. 113, No. 2, pp. 253-256 (2002).*
Parathath et al. Nitrix oxide synthase isoforms undertake unique roles during excitoxicity. Stroke, vol. 38, pp. 1938-1945 (2007).*
Sakanaka et al. In vivo evidence that erythropoietin protects neurons from ischemic damage. Abstract; Proc. Natl. Acad. Sci. USA vol. 95, pp. 4635-4640 (Apr. 1998).*
Siren et al. Erythropoietin prevents neuronal apoptosis after cerebral ischemia and metabolic stress. Abstract; Proc. Natl. Acad. Sci. USA vol. 98/7, pp. 4044-4049 (Mar. 2001).*
Morishita et al. Erythropoietin receptor is expressed in rat hippocampal and cerebral cortical neurons, and erythropoietin prevents in vitro glutamate-induced neuronal death. Abstract; Neuroscience vol. 76/1 pp. 105-116 (1997).*

(Continued)

*Primary Examiner*—Marianne P Allen
*Assistant Examiner*—Regina M DeBerry
(74) *Attorney, Agent, or Firm*—McDermott Will & Emery LLP

(57) ABSTRACT

The present invention provides a method of providing acute neuroprotection by inducing the erythropoietin (EPO) signaling pathway in neuronal cells close to or subsequent to the time of excitatory insult; and inducing an insulin-like growth factor (IGF) signaling pathway in the neuronal cells close to or subsequent to the time of excitatory insult, thereby producing a synergistic acute neuroprotective effect in the neuronal cells. The invention also provides a method of preventing or reducing the severity of a neurologic condition in a subject by administering to the subject EPO or an active fragment or analog thereof at a dose of at most 2000 U/kg; and administering to the subject an IGF or an active fragment or analog thereof, thereby providing neuroprotection and preventing or reducing the severity of the neurologic condition. Such a method can be used to prevent or reduce the severity of, for example, Alzheimer's disease, Parkinson's disease, Huntington's disease, epilepsy, amyotrophic lateral sclerosis, multiple sclerosis, a movement disorder, HIV-associated dementia, HIV-associated neuropathy, neuropathic pain, migraine, glaucoma, drug addiction, drug withdrawal, drug dependency, depression or anxiety.

68 Claims, 10 Drawing Sheets

OTHER PUBLICATIONS

Heck et al. Insulin-like growth factor-1-mediated neuroprotection against oxidative stress is associated with activation of nuclear kappaB. Abstract; J. Biol. Chem. vol. 274/14 pp. 9828-9835 (Apr. 1999).*

Sizonenko et al. Neuroprotective effects of the N-terminal tripeptide of IGF-1, glycine-proline-glutamate, in the immature rat brain after hypoxic-ischemic injury. Abstract; Brain Res. vol. 922/1 pp. 42-50 (Dec. 2001).*

Liu et al. Intranasal administration of insulin-like growth factor-I bypasses the blood-brain barrier and protects against focal cerebral ischemic damage. Abstract; J. Neurol. Sci. vol. 187/1-2 pp. 91-97 (Jun. 2001).*

Tagami et al. Insulin-like growth factors prevent apoptosis in cortical neurons isolated from stroke-prone spontaneously hypertensive rats. Abstract; Lab Invest. vol. 76/5 pp. 603-612 (May 1997).*

Digicaylioglu et al. Erythropoietin protects rat central neurons from NMDA- and NO-induced apoptosis. Society for Neuroscience Abstracts, 1997, vol. 23, No. 1-2, pp. 1667. Meeting Info:27th Annual Meeting of the Society for Neuroscience, New Orleans, Louisiana, USA (Oct. 25-30, 1997).*

Tagami et al. Insulin-like growth factors prevent apoptosis in cortical neurons isolated from stroke-prone spontaneously hypertensive rats. Laboratory Investigation, vol. 76, No. 5, pp. 603-612 (1997).*

Arsenijevic and Weiss, "Insulin-like growth factor-I is a differentiation factor for postmitotic CNS stem cell-derived neuronal precursors: distinct actions from those of brain-derived neurotrophic factor," *J. Neurosci.* 18:2118-2128 (1998).

Bain et al., "Embryonic stem cells express neuronal properties in vitro," *Devel. Biol.* 168:342-357 (1995).

Barbone et al., "New epoetin molecules and novel therapeutic approaches," *Nephrol. Dial. Transplant* 14 (Suppl. 2) :80-84 (1999).

Bayne et al., "The roles of tyrosines 24, 31, and 60 in the high affinity binding of insulin-like growth factor-I to the type 1 insulin-like growth factor receptor," *J. Biol. Chem.* 265:15648-15652 (1990).

Bhatia et al., "A newly discovered class of human hematopoietic cells with SCID-repopulating activity," *Nature Medicine* 4:1038-1045 (1998).

Brines et al., "Erythropoietin crosses the blood-brain barrier to protect against experimental brain injury," *Proc. Natl. Acad. Sci. USA* 97:10526-10531 (2000).

Brooker et al., "Endogenous IGF-1 regulates the neuronal differentiation of adult stem cells," *J. Neurosci. Res.* 59:332-341 (2000).

Cascieri and Bayne, "Analysis of the interaction of IGF-I analogs with the IGF-I receptor and IGF binding proteins," in LeRoith and Raizada, *Current Directions in Insulin-like Growth Factor Research*, Plenum Press, New York, 1994.

Damen et al., "Phosphorylation of tyrosine 503 in the erythropoietin receptor (EpR) is essential for binding the P85 subunit of phosphatidylinositol (PI) 3-kinase and for EpR-associated PI 3-kinase activity," *J. Biol. Chem.* 270:23402-23408 (1995).

Derby et al., "Identification of the residues involved in homodimer formation of recombinant human erythropoietin," *Int. J. Peptide Protein Res.* 47:201-208 (1996).

DePaolis et al., "Characterization of erythropoietin dimerization," *J. Pharm. Sci.* 84:1280-1284 (1995).

Digicaylioglu and Lipton, "Erythropoietin-mediated neuroprotection involves cross-talk between Jak2 and NF-kappaB signalling cascades," *Nature* 412:641-647 (2001).

Digicaylioglu and Lipton, "Erythropoietin and IGF-1 Provide Neuroprotection from NMDA-Induced Apoptosis via a P13 Kinase/AKT Signaling Pathway," Center for Neuroscience and Aging, The Burnham Institute, La Jolla, CA, USA, Session #764.16 (Aug. 2001).

Elliott et al., "Activation of the erythropoietin (EPO) receptor by bivalent anti-EPO receptor antibodies," *J. Biol. Chem.* 271:24691-24697 (1996).

Francis et al., "Novel recombinant fusion protein analogues of insulin-like growth factor (IGF)-I indicate the relative importance of IGF-binding protein and receptor binding for enhanced biological potency," *J. Mol. Endocrinol.* 8:213-223 (1992).

Gary and Mattson, "Integrin signaling via the PI3-kinase-Akt pathway increases neuronal resistance to glutamate-induced apoptosis," *J. Neurochem.* 76:1485-1496 (2001).

Ghosh and Greenberg, "Distinct roles for bFGF and NT-3 in the regulation of cortical neurogenesis," *Neuron* 15:89-103 (1995).

He et al., "Association of the p85 regulatory subunit of phosphatidylinositol 3-kinase with an essential erythropoietin receptor subdomain," *Blood* 82:3530-3538 (1993).

Heck et al., "Insulin-like growth factor-1-mediated neuroprotection against oxidative stress is associated with activation of nuclear factor kB," *J. Biol. Chem.* 274:9828-9835 (1999).

Holcik and Korneluk, "XIAP, the guardian angel," *Nat. Rev. Mol. Cell. Biol.* 2:550-556 (2001).

Holly et al., "The role of growth hormone in diabetes mellitus," *J. Endocrin.* 118:353-364 (1988).

Iwasaki and Ikeda, "Prevention by insulin-like growth factor-I and riluzole in motor neuron death after neonatal axotomy," *J. Neurological Sci.* 169:148-155 (1999).

Johe et al., "Single factors direct the differentiation of stem cells from the fetal and adult central nervous system," *Genes Develop.* 10:3129-3140 (1996).

Leverrier et al., "Role of PI3-kinase in Bcl-X induction and apoptosis inhibition mediated by IL-3 or IGF-1 in Baf-3 cells," *Cell Death and Differentiation* 6:290-296 (1999).

Lipton and Rosenberg, "Excitatory amino acids as a final common pathway for neurologic disorders," *New Engl. J. Med.* 330:613-622 (1994).

Liu et al., "Intranasal administration of insulin-like growth factor-I bypasses the blood-brain barrier and protects against focal cerebral ischemic damage," *J. Neur. Sci.* 187:91-97 (2001).

Lowman et al., "Molecular mimics of insulin-like growth factor 1 (IGF-1) for inhibiting IGF-1: IGF-Binding protein interactions," *Biochemistry* 37:8870-8878 (1998).

Masuda et al., "Functional erythropoietin receptor of the cells with neural characteristics," *J. Biol. Chem.* 268:11208-11216 (1993).

Matthews et al., "A sequential dimerization mechanism for erythropoietin receptor activation," *Proc. Natl. Acad. Sci. USA* 93:9471-9476 (1996).

Miyoshi et al., "Transduction of human CD34+ cells that mediate long-term engraftment of NOD/SCID mice by HIV vectors," *Science* 283:682-686 (1999).

Morishita et al., "Erythropoietin receptor is expressed in rat hippocampal and cerebral cortical neurons, and erythropoietin prevents in vitro glutamate-induced neuronal death," *Neuroscience* 76:105-116 (1997).

Okajima et al., "Insulin-like growth factor-I augments erythropoietin-induced proliferation through enhanced tyrosine phosphorylation of STAT5," *J. Bio. Chem.* 273:22877-22883 (1998).

Pietrowsky et al., "Brain potential changes after intranasal vs. intravenous administration of vasopressin: Evidence for a Direct nose-brain pathway for peptide effects in humans," *Soc. Biological Psych.* 39:332-340 (1996).

Qureshi et al., "Mimicry of erythropoietin by a nonpeptide molecule," *Proc. Natl. Acad. Sci. USA* 96:12156-12161 (1999).

Sakanaka et al., "In vivo evidence that erthropoietin protects neurons from ischemic damage," *Proc. Natl. Acad. Sci. USA* 95:4635-4640 (1998).

Scheid and Woodgett, "PKB/AKT: Functional insights from genetic models," *Nat. Rev. Mol. Cell. Biol.* 2:760-768 (2001).

Schneider et al., "Homodimerization of erythropoietin receptor by a bivalent monoclonal antibody triggers cell proliferation and differentiation of erythroid precursors," *Blood* 89:473-482 (1997).

Seigel et al., "Inhibition of neuroretinal cell death by insulin-like growth factor-1 and its analogs," *Molecular Vision* 6:157-163 (2000).

Shimoda et al., "Effects of dose, pH and osmolarity on intranasal absorption of recombinant human erythropoietin in rats," *Biol. Pharm. Bull.* 18:734-739 (1995).

Sinor and Greenberg, "Erythropoietin protects cultured cortical neurons, but not astroglia, from hypoxia and AMPA toxicity," *Neurosci. Letters* 290:213-215 (2000).

Siren et al., "Erythropoietin prevents neuronal apoptosis after cerebral ischemia and metabolic stress," *Proc. Natl. Acad. Sci. USA* 98:4044-4049 (2001).

Sizonenko et al., "Neuroprotective effects of the N-terminal tripeptide of IGF-1, glycine-proline-glutamate, in the immature rat brain after hypoxic-ischemic injury," *Brain Research* 922:42-50 (2001).

Slieker et al., "Insulin and IGF-1 analogs: Novel approaches to improved insulin pharmacokinetics," pp. 35-32 in LeRoith and Raizada, *Current Directions in Insulin-Like Growth Factor Research*, Plenum Press, New York, 1994.

Sytkowski et al., "Human erythropoietin dimers with markedly enhanced in vivo activity," *Proc. Natl. Acad. Sci. USA* 95:1184-1188 (1998).

Tagami et al., "Insulin-like growth factor-1 attenuates apoptosis in hippocampal neurons caused by cerebral ischemia and reperfusion in stroke-prone spontaneously hypertensive rats," *Lab. Invest.* 76:613-617 (1997).

Uchida et al., "Direct isolation of human central nervous system stem cells," *Proc. Natl. Acad. Sci. USA* 97:14720-14725 (2000).

Vaillant et al., "Depolarization and neurotrophins converge on the phosphatidylinositol 3-kinase-Akt pathway to synergistically regulate neuronal survival," *J. Cell Biol.* 146:955-966 (1999).

Williams et al., "A PDGF-regulated immediate early gene response initiates neuronal differentiation in ventricular zone progenitor cells," *Neuron* 18:553-562 (1997).

Wrighton et al., "Small peptides as potent mimetics of the protein hormone erythropoietin," *Science* 273:458-463 (1996).

Wrighton et al., "Increased potency of an erythropoietin peptide mimetic through covalent dimerization," *Nature Biotech.* 15:1261-1265 (1997).

Yin et al., "AC133, a novel marker for human hematopoietic stem and progenitor cells," *Blood* 90:5002-5012 (1997).

Digicaylioglu et al., "Acute neuroprotective synergy of erythropoietin and insulin-like growth factor I," *Proc. Natl. Acad. Sci. USA* 101:9855-9860 (2004).

\* cited by examiner

A
```
   1 cccggagccg gaccggggcc accgcgcccg ctctgctccg acaccgcgcc ccctggacag
  61 ccgccctctc ctccaggccc gtggggctgg ccctgcaccg ccgagcttcc cgggatgagg
 121 gcccccggtg tggtcacccg gcgcgcccca ggtcgctgag ggaccccggc caggcgcgga
 181 gatgggggtg cacgaatgtc ctgcctggct gtggcttctc ctgtccctgc tgtcgctccc
 241 tctgggcctc ccagtcctgg gcgcccacc acgcctcatc tgtgacagcc gagtcctgga
 301 gaggtacctc ttggaggcca aggaggccga aatatcacg acgggctgtg ctgaacactg
 361 cagcttgaat gagaatatca ctgtcccaga caccaaagtt aatttctatg cctggaagag
 421 gatggaggtc gggcagcagg ccgtagaagt ctggcagggc ctggccctgc tgtcggaagc
 481 tgtcctgcgg ggccaggccc tgttggtcaa ctcttcccag ccgtgggagc cctgcagct
 541 gcatgtggat aaagccgtca gtggccttcg cagcctcacc actctgcttc gggctctgcg
 601 agcccagaag gaagccatct ccctccaga tgcggcctca gctgctccac tccgaacaat
 661 cactgctgac actttccgca aactcttccg agtctactcc aatttcctcc ggggaaagct
 721 gaagctgtac acaggggagg cctgcaggac aggggacaga tgaccaggtg tgtccacctg
 781 ggcatatcca ccacctccct caccaacatt gcttgtgcca cacctcccc cgccactcct
 841 gaacccgtc gagggctct cagctcagcg ccagcctgtc ccatggacac tccagtgcca
 901 gcaatgacat ctcaggggcc agaggaactg tccagagagc aactctgaga tctaaggatg
 961 tcacagggcc aacttgaggg cccagagcag gaagcattca gagagcagct ttaaactcag
1021 ggacagagcc atgctgggaa gacgcctgag ctcactcggc ccctgcaaa atttgatgcc
1081 aggacacgct ttggaggcga tttacctgtt ttcgcaccta ccatcaggga caggatgacc
1141 tggagaactt aggtggcaag ctgtgacttc tccaggtctc acgggcatgg gcactccctt
1201 ggtggcaaga gcccccttga caccggggtg gtgggaacca tgaagacagg atgggggctg
1261 gcctctggct ctcatggggt ccaagttttg tgtattcttc aacctcattg acaagaactg
1321 aaaccaccaa aaaaaaaaa aa
```

B MGVHECPAWLWLLLSLLSLPLGLPVLGAPPRLICDSRVLERYLL
EAKEAENITTGCAEHCSLNENITVPDTKVNFYAWKRMEVGQQAVEVWQGLALLSEAVL
RGQALLVNSSQPWEPLQLHVDKAVSGLRSLTTLLRALRAQKEAISPPDAASAAPLRTI
TADTFRKLFRVYSNFLRGKLKLYTGEACRTGDR

C APPRLICDSRVLERYLL
EAKEAENITTGCAEHCSLNENITVPDTKVNFYAWKRMEVGQQAVEVWQGLALLSEAVL
RGQALLVNSSQPWEPLQLHVDKAVSGLRSLTTLLRALRAQKEAISPPDAASAAPLRTI
TADTFRKLFRVYSNFLRGKLKLYTGEACRTGDR

FIGURE 1

A
```
  1 cttcagaagc aatgggaaaa atcagcagtc ttccaaccca attatttaag tgctgctttt
 61 gtgatttctt gaaggtgaag atgcacacca tgtcctcctc gcatctcttc tacctggcgc
121 tgtgcctgct caccttcacc agctctgcca cggctggacc ggagacgctc tgcggggctg
181 agctggtgga tgctcttcag ttcgtgtgtg gagacagggg cttttatttc aacaagccca
241 cagggtatgg ctccagcagt cggagggcgc ctcagacagg tatcgtggat gagtgctgct
301 tccggagctg tgatctaagg aggctggaga tgtattgcgc acccctcaag cctgccaagt
361 cagctcgctc tgtccgtgcc cagcgccaca ccgacatgcc caagacccag aaggaagtac
421 atttgaagaa cgcaagtaga gggagtgcag gaaacaagaa ctacaggatg taggaagacc
481 ctcctgagga gtgaagagtg acatgccacc gcaggatcct ttgctctgca cgagttacct
541 gttaaacttt ggaacaccta ccaaaaaata agtttgataa catttaaaag atgggcgttt
601 cccccaatga aatacacaag taaacattcc aacattgtct ttaggagtga tttgcacctt
661 gcaaaaatgg tcctggagtt ggtagattgc tgttgatctt ttatcaataa tgttctatag
721 aaaag
```

B  MGKISSLPTQLFKCCFCDFLKVKMHTMSSSHLFYLALCLLTFTS
SATAGPETLCGAELVDALQFVCGDRGFYFNKPTGYGSSSRRAPQTGIVDECCFRSCDL
RRLEMYCAPLKPAKSARSVRAQRHTDMPKTQKEVHLKNASRGSAGNKNYRM

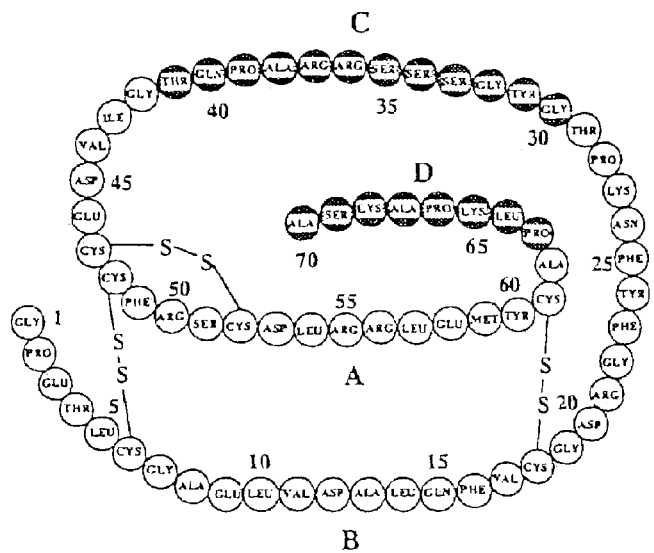

FIGURE 2

NEUROPROTECTIVE SYNERGY OF ERYTHROPOIETIN AND INSULIN-LIKE GROWTH FACTORS

This application claims benefit of the filing date of U.S. Provisional Application No. 60/388,058, filed Jun. 11, 2002, and of U.S. Provisional Application No. 60/458,145, filed Mar. 26, 2003, which are incorporated herein by reference.

This application was made with government support under P01 HD29587, R01 NS43242 and NS43242 awarded by the National Institute of Health. The government has certain rights in the invention.

FIELD OF THE INVENTION

The invention relates to the prevention and treatment of acute and chronic neurodegenerative conditions, and to erythropoietin and insulin-like growth factors and analogs of these factors.

BACKGROUND INFORMATION

For a variety of serious neurodegenerative diseases, there exist no effective therapies or cures. For example, Parkinson's disease is a progressive and ultimately fatal neurodegenerative disorder characterized by loss of the pigmented dopaminergic neurons of the substantia nigra. The symptoms of Parkinson's disease often can be managed initially by administration of L-DOPA, the immediate precursor of dopamine. However, reduced efficacy of L-DOPA treatment typically occurs over time. Programmed cell death (apoptosis) has been implicated in this neurodegenerative disorder.

In Alzheimer's disease, the most common neurodegenerative disease and most frequent cause of dementia, progressive failure of memory and degeneration of temporal and parietal association cortex result in speech impairment and loss of coordination, and, in some cases, emotional disturbance. Alzheimer's disease generally progresses over many years, with patients gradually becoming immobile, emaciated and susceptible to pneumonia.

Neuroprotective therapy has been sought for a variety of acute and chronic neurological conditions, including stroke, Parkinson's disease, Alzheimer's disease, Huntington's disease, amyotrophic lateral sclerosis, multiple sclerosis, epilepsy and pain. Present therapies are relatively ineffective or are accompanied by unwanted side effects. In particular, erythropoietin (EPO) can be neuroprotective when administered in high doses; however, such doses also promote the formation of new red blood cells, consequently causing side effects such as "sludging" of the blood and leading to increased risk of stroke. Thus, there is a need for novel methods of using erythropoietin to achieve neuroprotection, that do not rely on excessively high doses of the factor. The present invention satisfies this need and provides related advantages as well.

SUMMARY OF THE INVENTION

The present invention provides a method of providing acute neuroprotection by inducing the erythropoietin (EPO) pathway in neuronal cells close to or subsequent to the time of excitatory insult; and inducing an insulin-like growth factor (IGF) pathway in the neuronal cells close to or subsequent to the time of excitatory insult, thereby producing a synergistic acute neuroprotective effect in the neuronal cells.

The present invention further provides a method of providing acute neuroprotection by contacting neuronal cells with EPO or an active fragment or analog thereof close to or subsequent to the time of excitatory insult; and contacting the neuronal cells with an IGF or an active fragment or analog thereof close to or subsequent to the time of excitatory insult, thereby producing a synergistic acute neuroprotective effect in the neuronal cells.

Many forms of erythropoietin, as well as active fragments and analogs thereof, can be useful in the methods of the invention. In one embodiment, neuronal cells are contacted with EPO or an active fragment thereof, for example, with human EPO or an active fragment thereof. In another embodiment, neuronal cells are contacted with an EPO analog, which can be, without limitation, a peptide, peptidomimetic, small molecule or nucleic acid EPO analog. In further embodiments, the invention is practiced with an EPO analog that includes the amino acid sequence GGTYSCHFG-PLTWVCKPQGG (SEQ ID NO: 7); GGDYHCRMG-PLTWVCKPLGG (SEQ ID NO: 8); GGVYACRMGPIT-WVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In another embodiment, the invention is practiced with EPO, or an active fragment or analog thereof, which has at least 10-fold higher affinity for the EPO receptor than native human EPO. In another embodiment, the invention is practiced with EPO or an active fragment or analog thereof which is oligomeric, for example, dimeric. As an example, such a dimeric form of EPO can be a dimer in which each monomer contains the amino acid sequence GGTYS CHFGPLTWVCKPQGG (SEQ ID NO: 7).

In a further embodiment, the invention is practiced with EPO or an active fragment or analog thereof that has a half-life greater than the half-life of native human EPO. In an additional embodiment, the invention is practiced with EPO or an active fragment or analog thereof that is hyper-glycosylated-compared to native human EPO. In yet a further embodiment, the invention is practiced by contacting neuronal cells with Darbepoietin. In any embodiment of the invention, soluble EPO receptor can be optionally included, for example, to prolong the half-life of EPO or an active fragment or analog thereof.

A variety of forms of IGF and active fragments and analogs thereof also are useful in the invention. In one embodiment, the invention is practiced by contacting neuronal cells with an IGF or an active fragment thereof, for example, IGF-I or an active fragment thereof. In an additional embodiment, the invention is practiced by contacting neuronal cells with human IGF-I or an active fragment thereof. In further embodiments, the invention is practiced with an IGF analog such as a peptide, peptidomimetic, small molecule or nucleic acid IGF analog including, without limitation, peptide, peptidomimetic, small molecule and nucleic acid IGF-I analogs.

In another embodiment, the invention is practiced with an IGF or active fragment or analog thereof which has at least 10-fold higher affinity for the IGF-I receptor than native human IGF-I. In a further embodiment, the invention is practiced with an IGF or active fragment or analog thereof which has an altered affinity for an IGF-binding protein (IBP). In yet a further embodiment, the invention is practiced with an IGF or active fragment or analog thereof which has a half-life greater than the half-life of native human IGF-I. In the methods of the invention, the two contacting steps can be performed in vitro or in vivo and further can be performed simultaneously or in any order.

Also provided herein is a method of preventing or reducing the severity of an acute neurologic condition in a subject by administering to the subject EPO or an active fragment or analog thereof close to or subsequent to the time of acute injury; and administering to the subject an IGF or an active fragment or analog thereof close to or subsequent to the time of acute injury, thereby providing a synergistic acute neuroprotective effect and preventing or reducing the severity of the acute neurologic condition. Such an acute neurologic condition can be, without limitation, stroke, head or spinal cord trauma, or seizure.

A method of the invention for preventing or reducing the severity of an acute neurologic condition can be practiced, for example, with EPO or an active fragment thereof, such as human EPO or an active fragment thereof. A method of the invention also can be practiced with an EPO analog, which can be, without limitation, a peptide, peptidomimetic, small molecule or nucleic acid analog. In particular embodiments, the invention is practiced with an EPO analog containing one of the following amino acid sequences: GGTYSCHFGPLTWVCKPQGG (SEQ ID NO: 7); GGDYHCRMGPLTWVCKPLGG (SEQ ID NO: 8); GGVYACRMGPITWVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In one embodiment, the invention is practiced with EPO or an active fragment or analog thereof which has at least 10-fold higher affinity for the EPO receptor than native human EPO. In another embodiment, the invention is practiced with EPO or an active fragment or analog thereof which is oligomeric, for example, dimeric. As an example, a method of the invention can be practiced with a dimeric form of EPO in which each monomer contains the amino acid sequence GGTYS<u>CHFGPLTWVC</u>KPQGG (SEQ ID NO: 7).

In a further embodiment, the invention is practiced with EPO or an active fragment or analog thereof which has a half-life greater than the half-life of native human EPO. Such a form of EPO can be hyper-glycosylated as compared to native human EPO and further can be, for example, Darbepoietin. The methods of the invention also optionally include the step of administering soluble EPO receptor to the subject.

A variety of forms of IGF and active fragments and analogs thereof are useful in the invention. In one embodiment, the invention is practiced by administering IGF or an active fragment thereof, for example, IGF-I or an active fragment thereof. In an additional embodiment, the invention is practiced by administering human IGF-I or an active fragment thereof. The invention also can be practiced by administering an IGF analog such as a peptide, peptidomimetic, small molecule or nucleic acid analog including, but not limited to, a variety of IGF-I analogs.

In one embodiment, a method of the invention for preventing or reducing the severity of an acute neurological condition is practiced with an IGF or active fragment or analog thereof which has at least 10-fold higher affinity for the IGF-I receptor than native human IGF-I. In another embodiment, the invention is practiced with an IGF or active fragment or analog thereof which has an altered affinity for an IGF-binding protein. In a further embodiment, the invention is practiced with an IGF or active fragment or analog thereof which has a half-life greater than the half-life of native human IGF. In the methods of the invention, EPO and IGF, or active fragments or analogs thereof, can be administered simultaneously or in any order and in the same or different pharmaceutical compositions.

Also provided by the invention is a method of preventing or reducing the severity of a neurologic condition in a subject by administering to the subject EPO or an active fragment or analog thereof at a dose of at most 2000 U/kg; and administering to the subject an IGF or an active fragment or analog thereof, thereby providing neuroprotection and preventing or reducing the severity of the neurologic condition. The EPO and IGF, or active fragments or analogs thereof, can be administered to the subject simultaneously or in any order and in the same or different pharmaceutical compositions. A variety of acute and chronic neurologic conditions can be treated according to a method of the invention including, but not limited to, Alzheimer's disease; Parkinson's disease; Huntington's disease; epilepsy; amyotrophic lateral sclerosis; multiple sclerosis; movement disorders; HIV-associated dementia; HIV-associated neuropathy; retinal degeneration including macular degeneration and light-induced retinal degeneration such as photoreceptor degeneration; neuropathic pain; migraine; glaucoma; drug addiction; drug withdrawal; drug dependency; and depression or anxiety.

Various forms of EPO and active fragments and analogs thereof are useful for preventing or reducing the severity of a neurologic condition according to a method of the invention. As an example, the invention can be practiced with EPO or an active fragment thereof such as human EPO or an active fragment thereof. A method of the invention also can be practiced with an EPO analog, which can be, without limitation, a peptide, peptidomimetic, small molecule or nucleic acid analog. In particular embodiments, the invention is practiced with an EPO analog containing one of the following amino acid sequences: GGTYSCHFGPLTWVCKPQGG (SEQ ID NO: 7); GGDYHCRMGPLTWVCKPLGG (SEQ ID NO: 8); GGVYACRMGPITWVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In one embodiment, a method of the invention for preventing or reducing the severity of a neurologic condition is practiced with EPO or an active fragment or analog thereof which has at least 10-fold higher affinity for the EPO receptor than native human EPO. In another embodiment, the invention is practiced with EPO or an active fragment or analog thereof which is oligomeric, for example, dimeric. The invention can be practiced, for example, with a dimeric form of EPO in which each monomer contains the amino acid sequence GGTYS<u>CHFGPLTWVC</u>KPQGG (SEQ ID NO: 7). In a further embodiment, the invention is practiced with EPO or an active fragment or analog thereof which has a half-life greater than the half-life of native human EPO. Such a form of EPO can be hyper-glycosylated as compared to native human EPO and further can be, for example, Darbepoietin. The methods of the invention further optionally include the step of administering soluble EPO receptor to the subject.

A variety of forms of IGF and active fragments and analogs thereof also are useful in the invention. In one embodiment, the invention is practiced by administering an IGF or an active fragment thereof, for example, IGF-I or an active fragment thereof. In an additional embodiment, the invention is practiced by administering human IGF-I or an active fragment thereof. In a further embodiment, the invention is practiced by administering an IGF analog such as a peptide, peptidomimetic, small molecule or nucleic acid analog including, but not limited to, a variety of IGF-I analogs.

In one embodiment, a method of the invention for preventing or reducing the severity of a neurological condition is practiced with an IGF or active fragment or analog thereof which has at least 10-fold higher affinity for the IGF-I receptor than native human IGF-I. In another embodiment, the invention is practiced with an IGF or active fragment or analog thereof which has an altered affinity for an IGF-binding protein. In a further embodiment, the invention is practiced with an IGF or active fragment or analog thereof which has a half-life greater than the half-life of native human IGF.

The present invention also provides a method of preventing or reducing the severity of a cerebral neurologic condition in a subject by transnasally administering to the subject EPO or an active fragment or analog thereof at a dose of at most 2000 U/kg; and transnasally administering to the subject an IGF or an active fragment or analog thereof, thereby providing acute neuroprotection and preventing or reducing the severity of the neurologic condition.

BRIEF DESCRIPTION OF THE DRAWINGS

FIG. 1 shows the nucleic acid and corresponding amino acid sequence of human erythropoietin (EPO). (A) Nucleotide sequence (SEQ ID NO: 1) of human EPO (Genbank accession X02157, version X02157.1). The coding sequence is shown as nucleotides 182 to 763 of SEQ ID NO: 1, with nucleotides 263 to 763 of SEQ ID NO: 1 encoding mature EPO. (B) The corresponding amino acid sequence (SEQ ID NO: 2) of human EPO. Residues 1 to 27 make up the signal sequence, with residues 28 to 193 constituting mature human EPO. (C) The amino acid sequence (SEQ ID NO: 3) of mature human EPO.

FIG. 2 shows the nucleic acid and corresponding amino acid sequence of human insulin-like growth factor-I (IGF-I). (A) The nucleotide sequence (SEQ ID NO: 4) human IGF-I (Genbank accession X00173, version X00173.1). The coding sequence is shown as nucleotides 12 to 473 of SEQ ID NO: 4. (B) The corresponding amino acid sequence (SEQ ID NO: 5) of human IGF-I. Residues 1 to 21 make up the signal sequence; residues 22 to 48 constitute a propeptide; residues 49 to 118 constitute mature IGF-I; and residues 119 to 153 make up the carboxy-terminal propeptide (domain E). (C) Mature human IGF-I (SEQ ID NO: 6) is shown schematically.

DETAILED DESCRIPTION OF THE INVENTION

The present invention is directed to the surprising discovery that erythropoietin and insulin-like growth factor (IGF) together mediate more rapid neuroprotection than either factor mediates alone, indicating that combined EPO and IGF treatment can be useful in providing neuroprotection in acute neurological conditions such as stroke, trauma and seizure. The invention also is directed to the surprising discovery that, together, EPO and IGF-I synergize to reduce apoptosis in neurons, providing enhanced neuroprotection at reduced concentrations, indicating that reduced concentrations of EPO and IGF-I can be useful in treating acute and chronic neurological disorders such as, without limitation, Alzheimer's disease, amyotrophic lateral sclerosis (ALS), Huntington's disease, glaucoma, HIV-associated dementia, multiple sclerosis; Parkinson's disease, and neuropathic pain.

Figure 3:
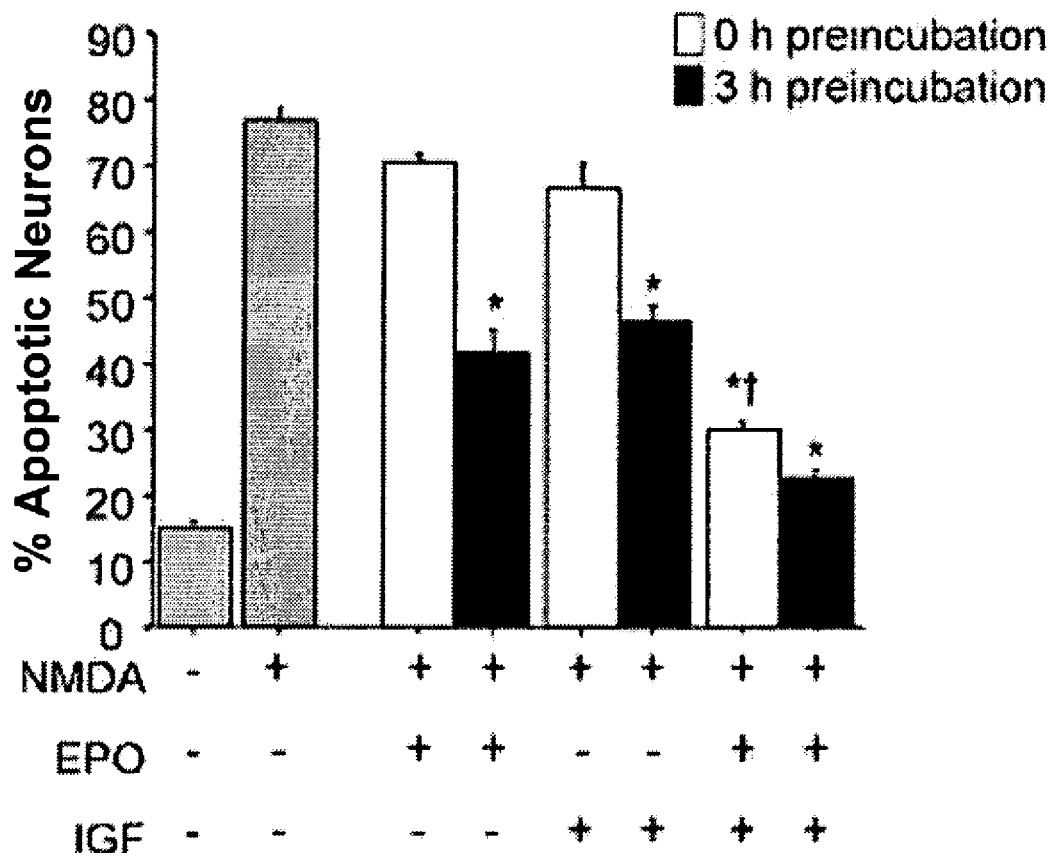
FIG. 3 shows that simultaneous co-administration of EPO and IGF-I ameliorates neuronal apoptosis induced by the excitotoxin N-methyl-D-aspartate (NMDA) acting at the NMDA receptor, a glutamate receptor in the brain. Overstimulation of this receptor mediates, at least in part, a wide range of acute and chronic neurologic disorders by permitting excessive $Ca^{2+}$ influx and subsequent free radical formation (nitric oxide and reactive oxygen species). Cultured rat cerebrocortical cells were incubated with NMDA (200 µM) for 20 minutes, a paradigm known to induce apoptotic neuronal cell death (Bonfoco et al., *PNAS* 92:7162-7166 (1995); Budd et al., *PNAS* 97:6161-6166 (2000)). EPO (10 U/ml), IGF-I (100 ng/ml), or 10 U/ml EPO plus 100 ng/ml IGF-I were applied three hours prior to or concurrent with NMDA exposure. Apoptotic neurons are represented by the percentage of MAP2-positive cells co-labeled by TUNEL 16 hours after NMDA exposure. In this and subsequent figures, results are mean±S.E. (n=3-5). $p<0.05$ by ANOVA versus NMDA (*) or versus simultaneous addition of NMDA and EPO or IGF-I (†).
Figure 9:
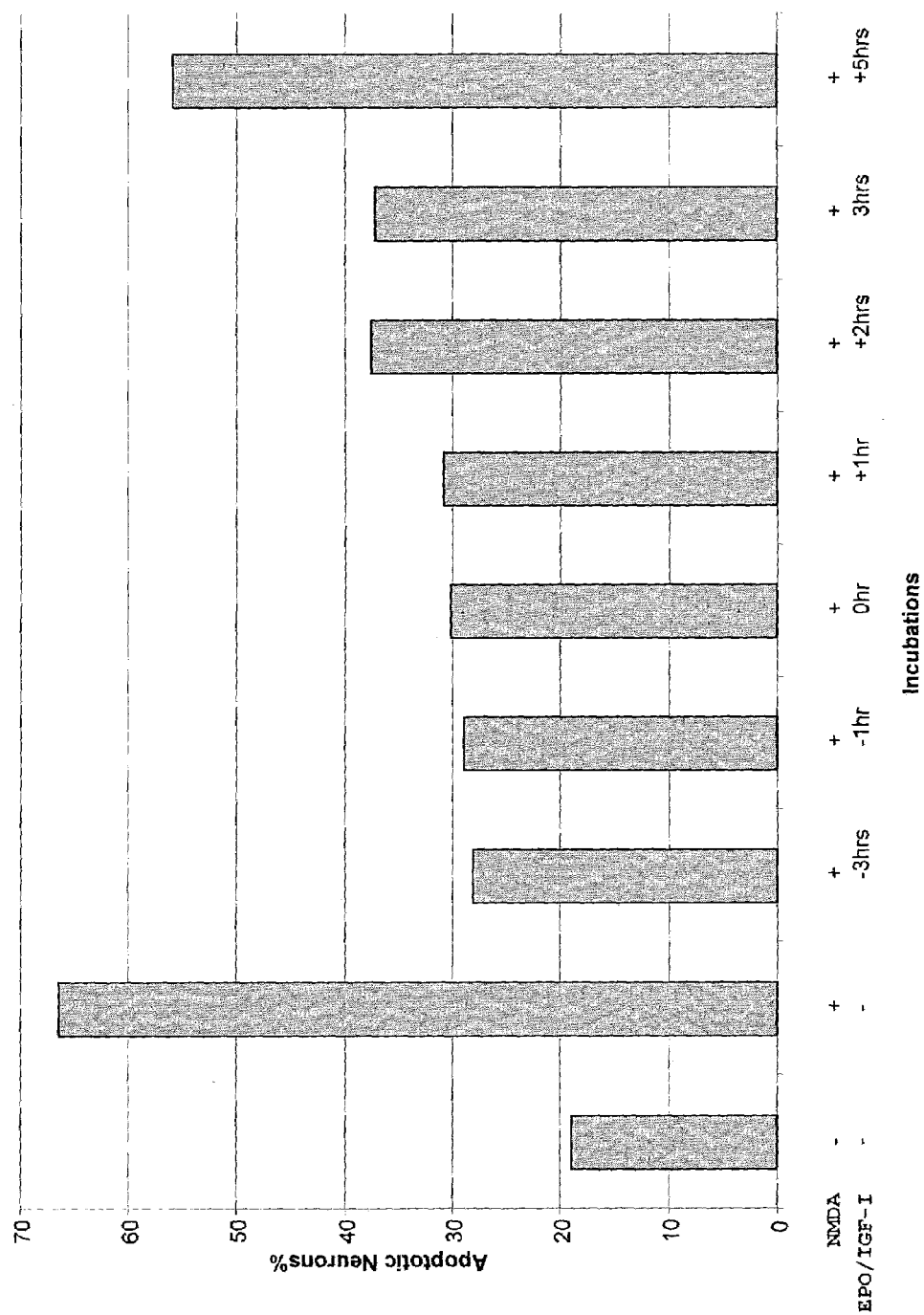
FIG. 9 shows that combined treatment with EPO and IGF-I can be effective in promoting neuronal survival when applied several hours following NMDA exposure. Cells were exposed to NMDA as described above and treated with 10 U/ml EPO and 100 ng/ml IGF-I three hours or one hour prior to NMDA exposure, at the time of NMDA exposure, or one hour, two hours, three hours or five hours subsequent to NMDA exposure. The percentage of apoptotic neurons was determined as described above.
Figure 10:
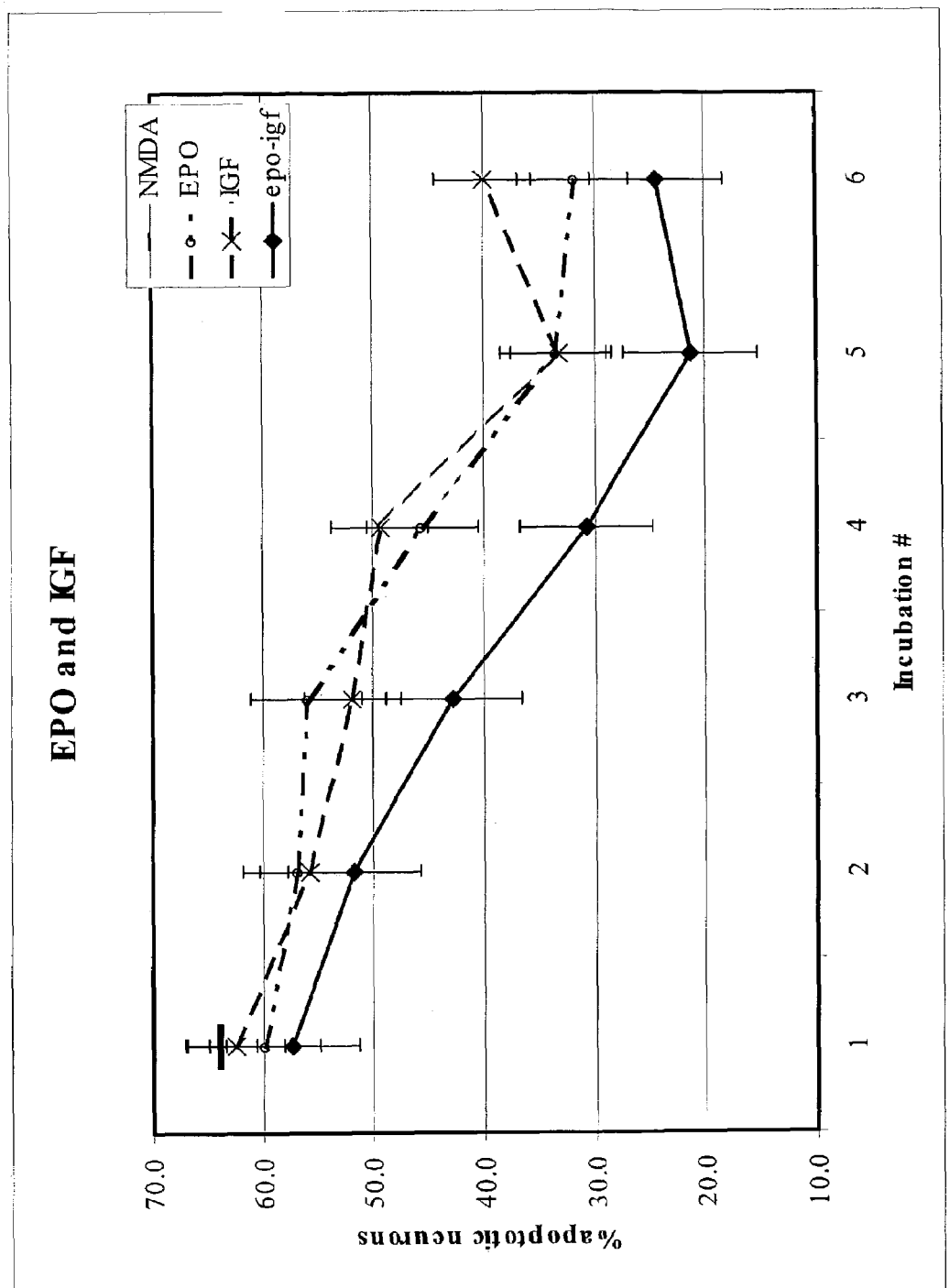
FIG. 10 shows that EPO and IGF-I together are more effective at reducing neuronal apoptosis than when used individually. Cells were exposed to 200 μM NMDA as described above and simultaneously treated with EPO alone, IGF-I alone, or EPO in combination with IGF-I at varying concentrations. Incubation 1: 0.5 U/ml EPO and 1 ng/ml IGF-1, alone or in combination. Incubation 2: 1.0 U/ml EPO and 10 ng/ml IGF-1, alone or in combination. Incubation 3: 2.0 U/ml EPO and 20 ng/ml IGF-1, alone or in combination. Incubation 4: 5.0 U/ml EPO and 50 ng/ml IGF-1, alone or in combination. Incubation 5: 10 U/ml EPO and 20 ng/ml IGF-1, alone or in combination. Incubation 6: 20 U/ml EPO and 400 ng/ml IGF-1, alone or in combination. The percentage of apoptotic neurons was determined 18 hours following NMDA exposure as described above. Incubations 3, 4 and 5 produced results with the EPO/IGF combination which were significantly different ($p<0.02$) from treatment with each cytokine alone.

As disclosed herein in Example I, the neuroprotective effects of concurrent EPO and IGF-I administration were compared to treatment with EPO or IGF-I individually in rat primary cerebrocortical cultures exposed to NMDA, an excitatory insult. Neuronal apoptosis was quantified by double labeling for TUNEL reactivity, which is indicative of apoptosis, and a neuron-specific marker, microtubule associated protein-2 (MAP2) 16 hours after NMDA insult. As shown in FIG. 3, a brief 20 minute exposure to NMDA produced an apoptotic appearance and TUNEL reactivity in 76+7% of MAP2-labeled neurons. Preincubation for three hours with either EPO (10 U/ml) or IGF-I (100 ng/ml) alone significantly attenuated neuronal apoptosis ($p<0.05$); however, treatment of neurons with EPO or IGF-I individually at the time of NMDA insult did not significantly reduce cell death (see FIG. 3). In contrast, application of EPO together with IGF-I at the time of NMDA exposure revealed a synergistic effect between the two factors, which together reduced neuronal apoptosis from about 76% to about 35%. As further shown in FIG. 9, combined EPO/IGF-I treatment dramatically reduced apoptosis when applied concurrently with NMDA exposure or when applied one hour, two hours or three hours following NMDA exposure. These results demonstrate that IGF-I and EPO synergize to mediate more rapid neuroprotection than either factor mediates in the absence of the other.

Figure 4:
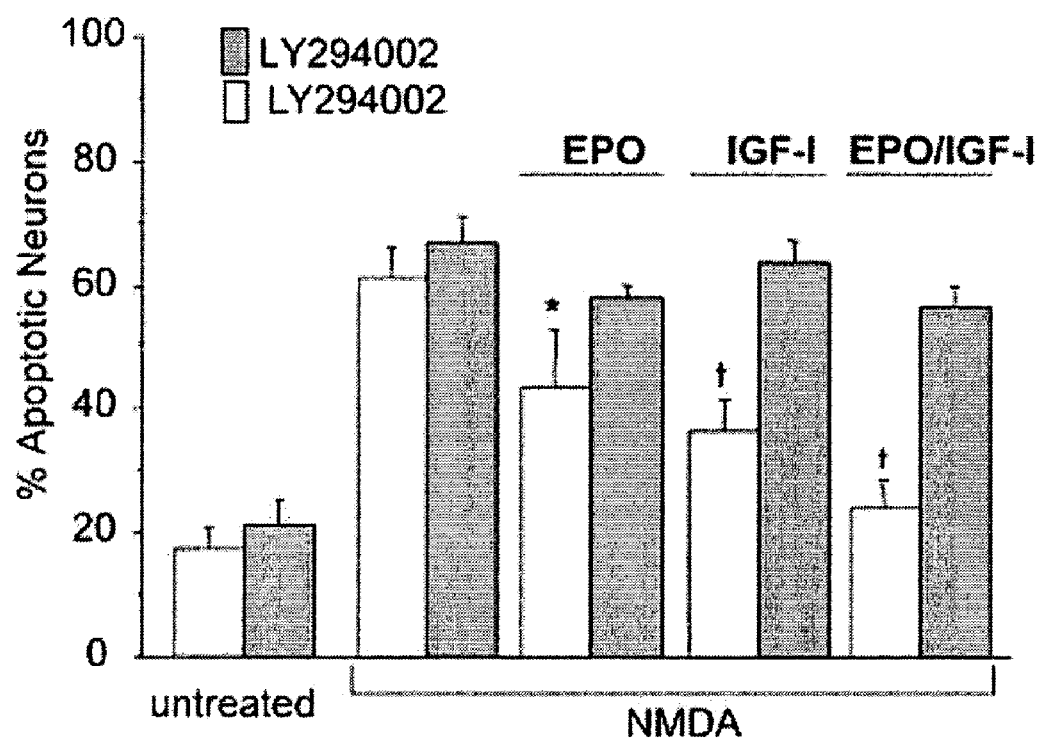
FIG. 4 shows that inhibition of PI3-kinase abrogates the anti-apoptotic effects of combined EPO and IGF-I treatment. Cerebrocortical cultures were exposed to 10 µM LY294002 (gray bars) for 30 minutes prior to incubation with EPO, IGF-I or EPO and IGF-I for three hours, at which time cells were subject to NMDA exposure. Neuronal apoptosis was assessed 16 hours after NMDA exposure by determining the percentage of MAP2 positive cells that were also TUNEL positive. *, $p<0.05$ or †, $p<0.01$ by ANOVA versus same treatment plus LY294002.
Figure 5:
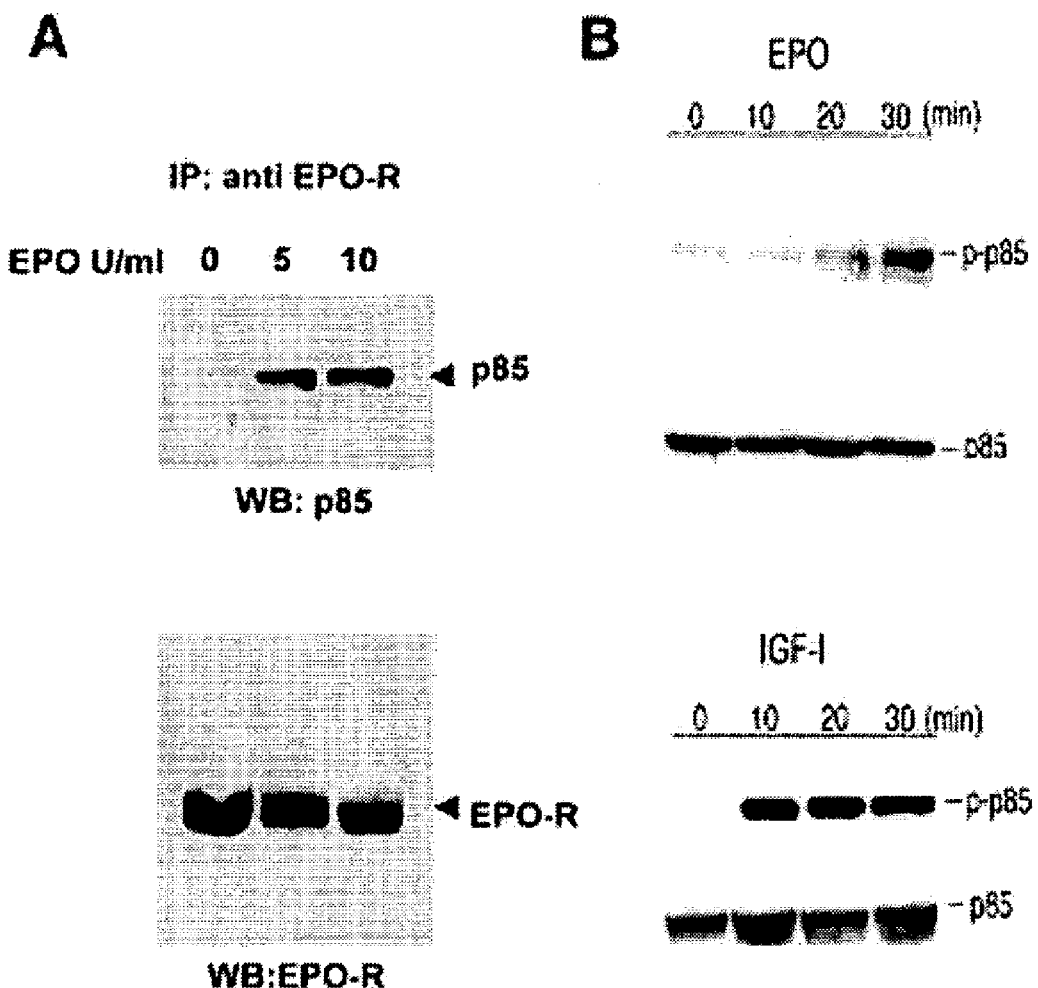
FIG. 5 shows that EPO and IGF-I each signal through PI3-kinase. (A) Treatment with EPO induces association of the p85 subunit of PI3-kinase with the EPO-R. Cerebrocortical cells were stimulated with 5 or 10 U/ml EPO for 30 minutes. EPO-R was immunoprecipitated from total cell lysates and separated on a SDS-polyacrylamide gel. The blot was then probed with anti-EPO-R antibody, stripped and reblotted with anti-p85 antibody. (B) Cerebrocortical cells were stimulated with EPO (5 U/ml, upper panel) or IGF-I (100 ng/ml, lower panel) for the indicated amount of time. Whole cell lysates were run on SDS-polyacrylamide gels; blots were probed with anti-phospho-p85 antibody, stripped, and then reprobed with anti-p85 antibody.

As further disclosed herein in Example IIA, rat cerebrocortical neurons were preincubated for three hours with EPO, IGF-I, or EPO in combination with IGF-I (EPO/IGF-I) in the presence or absence of 10 μM LY294002, a specific PI3-kinase inhibitor. The results shown in FIG. 4 demonstrate that LY294002 abolished the neuroprotective effect of EPO and IGF-I either alone or in combination ($p<0.05$) but did not itself cause neuronal apoptosis in cerebrocortical cultures or increase the amount of apoptosis induced by NMDA, indicating that PI3-kinase activity is required for EPO- and IGF-I-mediated neuroprotection. Furthermore, individual treatment with either EPO or IGF-I induced phosphorylation of the p85 regulatory subunit of PI3-kinase in a time-dependent manner; IGF-I incubation resulted in maximal phosphorylation of the p85 subunit after 10 minutes and EPO-induced phosphorylation was observed after 20 to 30 minutes (Example IIB; FIG. 5A). Given that phosphorylation of the p85 regulatory subunit is known to activate PI3-kinase by leading to release of the catalytic subunit, these results indicate that both EPO and IGF-I activate PI3-kinase.

Figure 6:
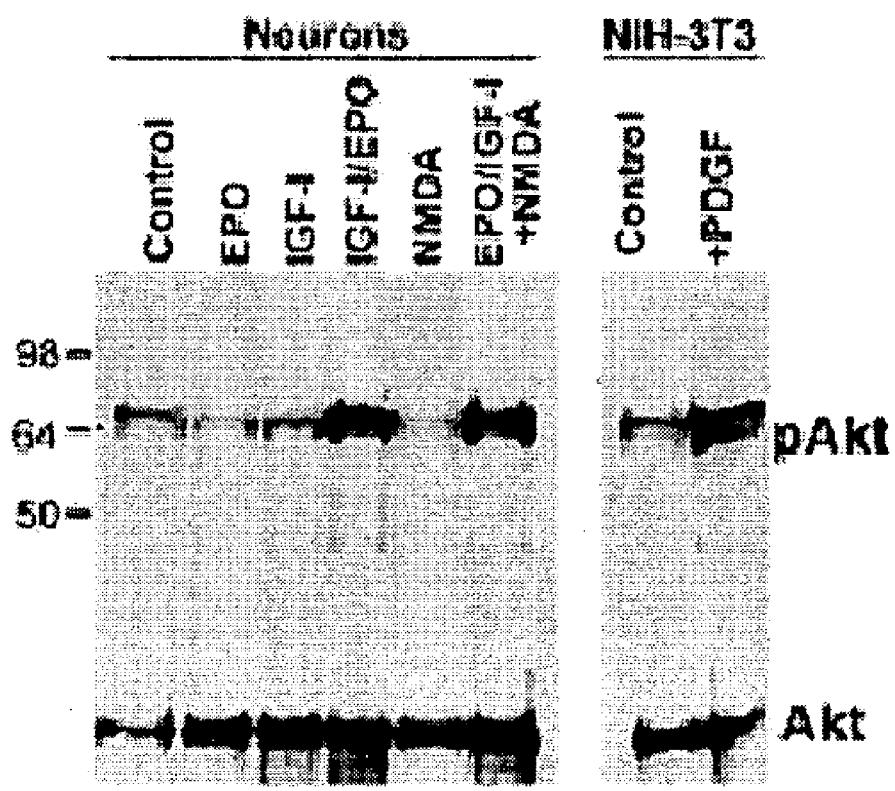
FIG. 6 shows that combined treatment with EPO and IGF-I induces Akt phosphorylation. Mixed neuronal/glial rat cerebrocortical cultures were treated for 20 minutes with 10 U/ml EPO, 100 ng/ml IGF-I, or both EPO and IGF-I, with or without simultaneous application of 200 µM NMDA. NIH3T3 cells stimulated with 100 µg/ml platelet-derived growth factor (PDGF) for 10 minutes served as a positive control. After three hours, cells were lysed, and whole-cell lysates subjected to immunoblot analysis with anti-phospho-Akt antibody; the blot was stripped and reprobed with an anti-Akt antibody.

As further disclosed herein in Example III, EPO and IGF-I treatment of neuronal cells can cooperatively activate Akt kinase, which is a kinase activated downstream of PI3-kinase-mediated production of 3' phospholipids. The Akt kinase is phosphorylated at two critical sites, serine-473 and threonine-308. As shown in FIG. 6A, a three hour incubation with EPO or IGF-I alone resulted in moderate Akt activation, as evidenced by increased phospho-serine-473 Akt, while co-incubation with maximally effective concentrations of EPO and IGF-I together resulted in a much larger increase in phospho-serine-473 Akt. Furthermore, cerebrocortical cultures expressing dominant negative Akt (dn-Akt) and incubated with EPO/IGF-I displayed significantly higher levels of NMDA-induced neuronal apoptosis in comparison with uninfected cultures or cultures infected with wild type Akt (wt-Akt; $p<0.01$). In sum, these results indicate that Akt serine-473 phosphorylation is synergistically induced by the combination of EPO and IGF-I and that Akt phosphorylation and activation play a role in the neuroprotection mediated by combined EPO/IGF-I treatment.

The results disclosed in Example VA show that treatment with EPO in combination with IGF-I prevents NMDA-induced neurotoxicity in cerebrocortical cultures in the presence of the active form of caspase-3. In particular, this result shows that prolonged survival of neurons following NMDA exposure and EPO/IGF-I treatment indicated that EPO/IGF-I neuroprotection occurs, at least in part, downstream of initial caspase-3 activation, which is typically associated with neuronal apoptosis within 16 hours of NMDA insult. Furthermore, as shown in FIG. 8A, combined EPO/IGF-I treatment resulted in long-term neuronal survival.

As disclosed herein in Example VC, cultures were incubated with EPO, IGF-I and NMDA and, after immunoprecipitation of the active form of caspase-3, immunoprecipitates were probed for the presence of XIAP, an anti-apoptotic protein that functions to inhibit caspase-3 activity. FIG. 8B shows that active caspase-3 was associated with XIAP in cultured neurons and that treatment with EPO and IGF-I increased the relative amount of XIAP associated with active caspase-3, consistent with negative regulation of the active form of caspase-3 by association with XIAP. Furthermore, the proteolytic activity of caspase-3 was modulated by combined EPO/IGF-I treatment. As shown in FIG. 8D, NMDA exposure resulted in increased caspase-3 proteolytic activity as indicated by enhanced DEVD substrate cleavage, while simultaneous application or 3 hour preincubation with EPO/ IGF-I diminished the NMDA-induced increase in caspase-3-like activity. This reduction in caspase-3 activity was partially inhibited by infection with a dominant negative Akt in cultures preincubated with EPO and IGF-I, demonstrating that Akt can play a role in regulating the proteolytic activity of neuronal caspase-3 (see FIG. 8D).

Figure 8:
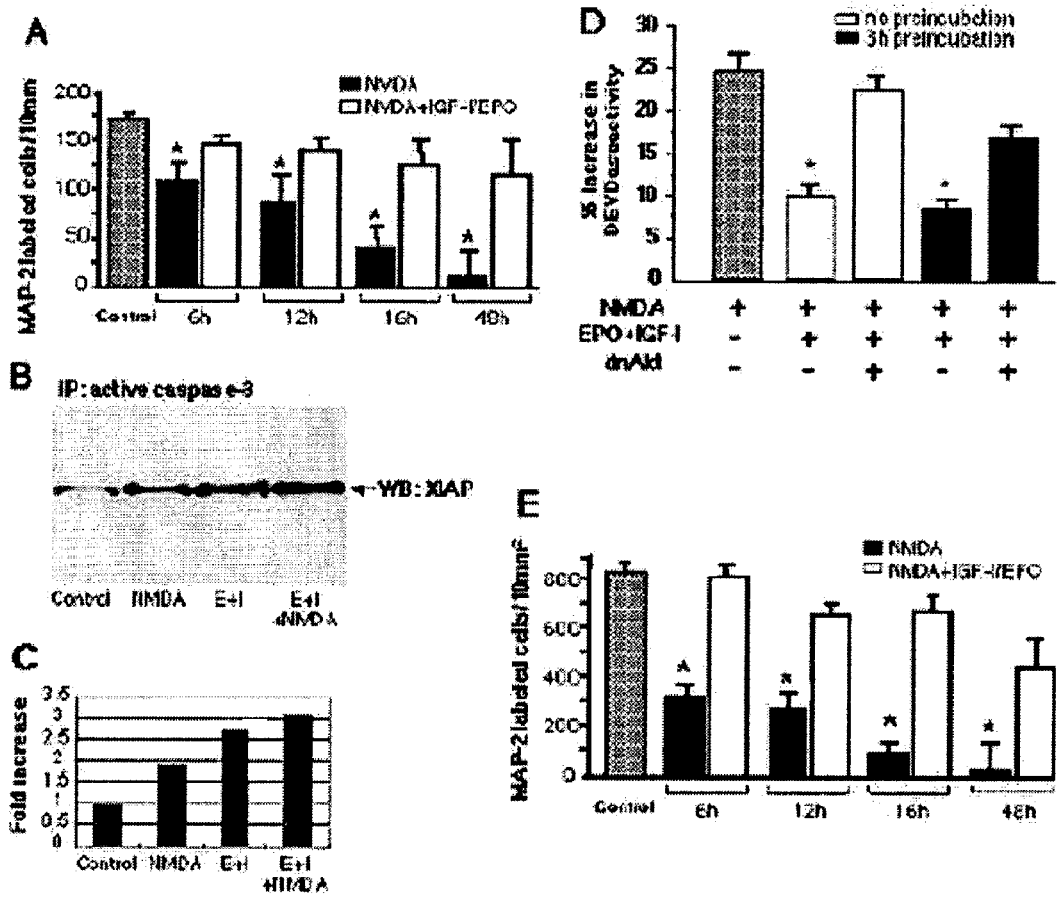
FIG. 8 shows that combined treatment with EPO and IGF-I promotes long-term neuronal survival downstream of caspase activation. (A) Survival of neurons in mixed neuronal-glial cultures after exposure to 200 µM NMDA for 20 minutes (black bars). EPO/IGF-I treatment (10 U/ml and 100 ng/ml, respectively) at the time of NMDA exposure promoted neuronal survival for up to 48 hours after the insult (white bars; *, $p<0.05$). (B) Cerebrocortical cultures were exposed to NMDA or EPO/IGF-I, or concurrently exposed to EPO/IGF-I and NMDA. Culture lysates were subjected to immunoprecipitation with an antibody specifically reactive with the active form of caspase-3. The immunoprecipitates were separated by electrophoresis and transferred to nitrocellulose membranes. EPO/IGF-I (with or without NMDA exposure) led to an increase in the amount of XIAP associated with active caspase-3. (C) Densitometry of XIAP, a protein inhibitor of apoptosis, revealed a 2.5 to 3-fold increase in the amount of XIAP bound to active caspase-3. (D) Caspase-3-like activity is reduced by EPO/IGF-I. Rat cerebrocortical cells were infected with an adenoviral vector encoding dominant-negative Akt (dn-Akt) or control vector. After 36 hours, cultures were incubated with EPO (10 U/ml), IGF-I (100 ng/ml) or EPO/IGF-I. Cells were exposed to 200 µM NMDA three hours after or simultaneously with EPO/IGF-I incubation. Caspase activity in cell lysates was assessed 16 hours after NMDA exposure and is shown as relative DEVDase activity expressed as percent increase over control levels. (E) Neuron-enriched cultures were exposed to NMDA insult (200 µM for 20 minutes) with or without EPO/IGF-I, and neuronal survival assessed at the indicated time points. Even in the absence of non-neuronal cells, EPO/IGF-I was equally effective in promoting long-term neuronal survival after exposure to NMDA.

Furthermore, as shown in FIG. 8E, prolonged survival afforded by combined EPO and IGF-I treatment did not require non-neuronal cells present in the mixed cerebrocortical cultures. Taken together with the results described above, this experiment demonstrates that combined EPO and IGF-I treatment promotes neuronal survival downstream of caspase-3 activation by a signal transduction pathway intrinsic to neurons.

Based on these discoveries, the present invention provides a method of providing acute neuroprotection by inducing the erythropoietin (EPO) pathway in neuronal cells close to or subsequent to the time of excitatory insult; and inducing an insulin-like growth factor (IGF) pathway in the neuronal cells close to or subsequent to the time of excitatory insult, thereby producing a synergistic acute neuroprotective effect in the neuronal cells.

The present invention further provides a method of providing acute neuroprotection by contacting neuronal cells with EPO or an active fragment or analog thereof close to or subsequent to the time of excitatory insult; and contacting the neuronal cells with an IGF or an active fragment or analog thereof close to or subsequent to the time of excitatory insult, thereby producing a synergistic acute neuroprotective effect in the neuronal cells.

Many forms of erythropoietin, as well as active fragments and analogs thereof, can be useful in the methods of the invention. In one embodiment, neuronal cells are contacted with EPO or an active fragment thereof, for example, with human EPO or an active fragment thereof. In another embodiment, neuronal cells are contacted with an EPO analog, which can be, without limitation, a peptide, peptidomimetic, small molecule or nucleic acid EPO analog. In further embodiments, the invention is practiced with an EPO analog that includes the amino acid sequence GGTYSCHFG-PLTWVCKPQGG (SEQ ID NO: 7); GGDYHCRMG-PLTWVCKPLGG (SEQ ID NO: 8); GGVYACRMGPIT-WVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In another embodiment, the invention is practiced with EPO, or an active fragment or analog thereof, which has at least 10-fold higher affinity for the EPO receptor than native human EPO. In another embodiment, the invention is practiced with EPO or an active fragment or analog thereof which is oligomeric, for example, dimeric. As an example, such a dimeric form of EPO can be a dimer in which each monomer contains the amino acid sequence GGTYS CHFGPLTWVCKPQGG (SEQ ID NO: 7).

In a further embodiment, the invention is practiced with EPO or an active fragment or analog thereof that has a half-life greater than the half-life of native human EPO. In an additional embodiment, the invention is practiced with EPO or an active fragment or analog thereof that is hyper-glycosylated compared to native human EPO. In yet a further embodiment, the invention is practiced by contacting neuronal cells with Darbepoietin. In any embodiment of the invention, soluble EPO receptor optionally can be included, for example, to increase the half-life of EPO or an active fragment or analog thereof.

A variety of forms of IGF and active fragments and analogs thereof also are useful in the invention. In one embodiment, the invention is practiced by contacting neuronal cells with an IGF or an active fragment thereof, for example, IGF-I or an active fragment thereof. In an additional embodiment, the invention is practiced by contacting neuronal cells with human IGF-I or an active fragment thereof. In further embodiments, the invention is practiced with an IGF analog such as a peptide, peptidomimetic, small molecule or nucleic acid IGF analog including, without limitation, peptide, peptidomimetic, small molecule and nucleic acid IGF-I analogs.

In another embodiment, the invention is practiced with an IGF or active fragment or analog thereof which has at least 10-fold higher affinity for the IGF-I receptor than native human IGF-I. In a further embodiment, the invention is practiced with an IGF or active fragment or analog thereof which has an altered affinity for an IGF-binding protein (IBP). In yet a further embodiment, the invention is practiced with an IGF or active fragment or analog thereof which has a half-life greater than the half-life of native human IGF-I. In the methods of the invention, the two contacting steps can be performed in vitro or in vivo and further can be performed simultaneously or in any order.

As used herein, the term "neuronal cell" means a nerve cell and is characterized, in part, by containing one or more markers of neuronal differentiation. Such a marker can be, for example, neurofilament, NeuN or MAP2. A neuronal cell further generally is characterized as containing neuronal-like processes.

The methods of the invention produce a synergistic acute neuroprotective effect in neuronal cells. As used herein, the term "acute neuroprotective effect" means a rapid effect that functions to reduce neuronal cell death or deterioration. An acute neuroprotective effect generally occurs within several minutes to about several hours. Thus, medicaments that produce an "acute neuroprotective effect" need not be pre-incubated with the neuronal cells prior to the time of excitatory insult, such as stroke, trauma or seizure, etc. An acute neuroprotective effect can rapidly function to reduce neuronal apoptosis.

The extent of apoptotic cell death can be determined by a variety of assays well known in the art. Such methods include light microscopy for determining the presence of one or more morphological characteristics of apoptosis, such as condensed or rounded morphology, shrinking and blebbing of the cytoplasm, preservation of the structure of cellular organelles including mitochondria, and condensation and margination of chromatin. The percentage of apoptotic cells also can be determined by assaying apoptotic activity using terminal deoxytransferase-mediated (TdT) dUTP biotin nick end-labeling (TUNEL) in conjunction with condensed cell morphology (Gavriel et al., *J. Cell Biol.* 119:493 (1992); Gorczyca et al., *Int. J. Oncol.* 1:639 (1992); Studzinski (Ed.), *Cell Growth and Apoptosis*, Oxford: Oxford University Press (1995)). ApopTag™ (ONCOR, Inc., Gaithersburg, Md.) is a commercially available kit for identification of apoptotic cells using digoxygenin labeling. In addition, apoptotic cells can be identified by detecting characteristic nucleosomal DNA fragments using agarose gel electrophoresis (Studzinski, supra, 1995; Gong et al., *Anal. Biochem.* 218:314 (1994)) or using DNA filter elution methodology to detect apoptosis-associated DNA fragmentation (Bertrand et al., *Drug Devel.*

34:138 (1995)). One skilled in the art understands that these, or other assays for apoptosis, can be performed using methodologies routine in the art.

The term "synergistic," as used herein in reference to an acute neuroprotective effect means an acute neuroprotective effect achieved by the combination of a particular dose of EPO, or active fragment or analog thereof, and a particular dose of IGF, or active fragment or analog thereof, that is significantly greater than the additive acute neuroprotective effect ensuing from individual treatment with the same doses of EPO and IGF, or active fragments or analogs thereof. In particular embodiments, the synergistic acute neuroprotective effect reduces neuronal cell death by at least 20%, 30%, 40%, 50%, 60%, 70%, 80%, 90% or more.

In the methods of the invention for providing acute neuroprotection, neuronal cells are contacted with EPO or an active fragment or analog thereof and IGF or an active fragment or analog thereof close to or subsequent to the time of excitatory insult. As used herein, the term "close to or subsequent to the time of excitatory insult" means that the treatment or contact occurs at any time after the stroke, trauma, seizure, poisoning or other excitatory insult or that the treatment or contact occurs at most an hour prior to the time of excitatory insult. Generally, the neuronal cells are contacted with EPO and IGF from about the time of insult to about 48 hours later and can be contacted, for example, between 30 minutes and 8 hours following the insult. In one embodiment, the EPO and IGF contacting steps occur within 30 minutes following excitatory insult. In another embodiment, the EPO and IGF contacting steps occur within the first hour following excitatory insult. In further embodiments, the EPO and IGF contacting steps occur within the first two hours following the excitatory insult, within the first three hours following the excitatory insult, within the first 12 hours following the excitatory insult, or within the first 24 hours following excitatory insult.

Erythropoietin (EPO) is the principal growth factor that induces proliferation and differentiation of erythroid progenitor cells and is a member of the cytokine family that includes interleukins 2 through 7, G-CSF, GM-CSF, TPO, growth hormone and leptin (Koury and Bondurant, Transfusion 30:673-674 (1992)).

Binding of EPO to its receptor triggers signal transduction by ligand-mediated receptor dimerization on the cell surface. Point mutations that introduce cysteine residues into the membrane proximal part of the extracellular domain of the EPO receptor, and which result in disulfide-linked receptor dimers on the cell surface, are constitutively active. Such receptors lead to cell proliferation of EPO-dependent cell lines and other biological effects of EPO in the absence of the hormone (Yoshimura et al., Nature 348:647-649 (1990); Watowich et al., Proc. Natl. Acad. Sci., USA 89:2140-2144 (1992); and Watowich et al., Mol. Cell. Biol. 14:3539-3549 (1994)). Expression of these constitutive EPO receptors in mice results in erythroleukemia through unregulated activation of the signaling pathway (Longmore and Lodish, Cell 67:1089-1102 (1991); Longmore et al., Mol. Cell. Biol. 14:2266-2277 (1994)). EPO receptor activation has been shown to follow a sequential dimerization mechanism, with binding to a high affinity site 1 on EPO preceding binding of the second receptor to a lower affinity site 2 (Matthews et al., Proc. Natl. Acad. Sci., USA 93: 9471-9476 (1996)).

As used herein, the term "erythropoietin" is synonymous with "EPO" and means a polypeptide that has substantially the amino acid sequence of naturally occurring human EPO or a homolog thereof. EPOs useful in the invention include human and other primate EPOs, mammalian EPOs such as bovine, porcine, murine and rat homologs and other vertebrate homologs such as Danio rerio homologs. Thus, the term EPO encompasses species homologs, alternatively spliced forms, isotype and glycosylation variants and precursors of the mature human EPO sequence (SEQ ID NO: 3) shown in FIG. 1. An EPO generally has an amino acid sequence with at least about 80% amino acid identity to the sequence of naturally occurring, mature human EPO (SEQ ID NO: 3) and can have, for example, 90% or 95% or more amino acid identity with SEQ ID NO: 3.

A variety of forms of erythropoietin with varying glycosylation patterns are available commercially, including but not limited to, EPOGEN (Amgen; Thousand Oaks, Calif.); EPOGIN (Chugai Pharmaceuticals; Tokyo, Japan); EPOMAX (Elanex; Bothell, Wash.); EPREX (Janssen-Cilag; Beerse, Belgium); NEORECORMON and RECORMON (Roche; Basel, Switzerland) and PROCRIT (Ortho Biotech; Raritan, N.J.); various forms of EPO also are available generically as EPOETIN ALFA, EPOETIN BETA and EPOETIN OMEGA. Thus, it is understood that an EPO useful in the invention can be obtained commercially or by a variety of well known methods, including, without limitation, purification from a natural source, recombinant expression, or peptide or chemical synthesis A method of the invention can be practiced, if desired, with an "EPO analog." As used herein, the term "EPO analog" means a molecule that induces or enhances the expression, activity or intracellular signaling of the erythropoietin receptor and that, in combination with an insulin-like growth factor, produces a synergistic acute neuroprotective effect in neurons. Such an analog can be, without limitation, a protein, peptide, peptidomimetic, small molecule, ribozyme, nucleic acid molecule, oligonucleotide, oligosaccharide, cell, phage or virus, or a combination thereof. As described further below, EPO analogs useful in the invention encompass, yet are not limited to, erythropoietin mimetic peptides (EMPs); cyclic molecules such as cyclic peptides or peptidomimetics; dimeric and oligomeric EPO analogs; analogs with increased plasma half-life; anti-EPO receptor antibodies; small molecule drugs that induce EPO receptor dimerization; hyperglycosylated forms of EPO; EPO-encoding nucleic acid molecules; and constitutive forms of the EPO receptor. It is understood that the term EPO analog encompasses active fragments of EPO, which are described hereinabove.

An EPO analog can be an erythropoietin mimetic peptide (EMP) containing at least one copy of the amino acid sequence YXCXXGPXTWXCXP, where X is any amino acid (Wrighton et al., Science 273:458-463 (1996)). In one embodiment, the EPO analog contains two or more copies of YXCXXGPXTWXCXP (Wrighton et al., Nature Biotechn. 15:1261-1265 (1997). In another embodiment, the EPO analog contains the sequence YXCXXGPXTWXCXP, where X is any amino acid and the cyclic portion is indicated by underlining. Erythropoietin mimetic peptides are known in the art and include EMP1 (SEQ ID NO: 7), EMP2 (SEQ ID NO: 8), EMP3 (SEQ ID NO: 9), EMP4 (SEQ ID NO: 10), EMP5 (SEQ ID NO: 11) and AF11154 (SEQ ID NO: 12) as shown in Table 1. Additional cyclic molecules including cyclic peptides and peptidomimetics and disulfide-bonded peptides and peptidomimetics also can be EPO analogs useful in the invention.

TABLE 1

| Analog | Sequence | IC$_{50}$ (μm) | SEQ ID NO: |
|---|---|---|---|
| EMP1 | GGTYSCHFGPLTWVCKPQGO | 0.2 | 7 |
| EMP2 | GGDYHCRMGPLTWVCKPLGG | 0.2 | 8 |

TABLE 1-continued

| Analog | Sequence | IC$_{50}$ (µm) | SEQ ID NO: |
|---|---|---|---|
| EMP3 | GGV<u>Y</u>ACRM<u>GPITWV</u>CS<u>P</u>LGC | 0.3 | 9 |
| EMP4 | VGN<u>YM</u>CHF<u>GPITWV</u>CR<u>P</u>GGG | 0.5 | 10 |
| EMP5 | GGL<u>YL</u>CRF<u>GPVTW</u>D<u>C</u>GYKGG | 1.0 | 11 |
| AF11154 | GG<u>C</u>RI<u>GPITWV</u>CGG | 10.0 | 12 |

Recombinant human EPO forms a dimer upon extensive heating, based on intermolecular disulfide bond formation involving cysteines-7 and -161 as described, for example, in Derby et al., supra, 1996. Thus, oligomeric forms of erythropoietin, as well as oligomeric EPO fragments and analogs thereof, can be useful in the invention. See, in general, DePaolis et al., *J. Pharm. Sci.* 84:1280-1284 (1995), and Derby et al., *Int. J. Peptide Protein Res.* 47:201-208 (1996).

Oligomeric forms of EPO or active fragments-or analogs thereof useful in the invention include dimers and trimers as well as higher multimeric forms. An oligomeric form of EPO can include two or more, three or more, four or more, five or more, six or more, seven or more, eight or more, nine or more, ten or more, fifteen or more, twenty or more, 50 or more, 100 or more, 200 or more, 500 or more, or 1000 or more copies of EPO or an active fragment or analog thereof. As examples, chemical cross-linking, synthetic peptide chemistry, phage display and conjugation of biotin-tagged EPO with streptavidin can be useful in generating oligomeric EPO analogs. Dimeric and trimeric EPO analogs can be formed using heterobifunctional crosslinking reagents, for example, by chemically modifying a first pool of erythropoietin monomers to contain free sulfhydryl residues and mixing this pool with a second pool containing maleimido groups; the oligomeric EPO subsequently can be purified, for example, by size exclusion HPLC as described, in Sytkowski et al., supra, 1998.

Native human erythropoietin has a relatively short plasma half-life of about 4 to 13 hours, while EPO analogs with a larger molecular size can have a reduced rate of clearance and, therefore, increased plasma survival and in vivo biological activity. Thus, higher molecular weight EPO analogs including oligomeric forms of EPO, or active fragments or analogs thereof, can exhibit an increased plasma half-life as compared to the half-life of native monomeric human EPO (Sytkowski et al., *Proc. Natl. Acad. Sci. USA* 95:1184-1188 (1998)). An oligomeric form of EPO can have, for example, a half-life of at least 15, 18, 21, 24, 48, 72 or 96 hours. One skilled in the art recognizes that, if desired, soluble EPO receptor can be included to increase the half-life of native erythropoietin, or an active fragment or analog thereof, and, therefore, therapeutic value.

As discussed above, binding of EPO to the EPO receptor results in receptor dimerization, as is common for growth factor and cytokine receptors. Dimerization of the EPO receptor can be sufficient to induce a biological-response characteristic of EPO. Thus, an EPO analog useful in the invention can promote dimerization of the EPO receptor. In one embodiment, the invention is practiced with an EPO analog which is a multivalent antibody, such as a bivalent monoclonal antibody, that binds the extracellular domain of the erythropoietin receptor and promotes receptor dimerization. Such bivalent anti-EPO receptor antibodies have been shown to mimic EPO activity as described, for example, in Schneider et al., *Blood* 89:473-482 (1997), and Elliot et al., *J. Biol. Chem.* 271: 24691-24697 (1996).

As used herein, the term "antibody" includes polyclonal and monoclonal antibodies, as well as polypeptide fragments of antibodies that retain binding activity for an EPO receptor of at least about 1×10$^{-5}$ M. One skilled in the art understands that anti-EPO receptor antibody fragments, such as Fab, F(ab')$_2$ and Fv fragments, can retain binding activity for EPO receptor and, thus, are included within the definition of the term antibody as used herein. The term antibody also encompasses non-naturally occurring antibodies and fragments containing, at a minimum, one V$_H$ and one V$_L$ domain, such as chimeric antibodies, humanized antibodies and single chain antibodies that specifically bind EPO receptor. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), *Antibody Engineering* (Second edition) New York: Oxford University Press (1995).

A variety of bivalent antibodies are useful in the invention, including, without limitation, naturally occurring monoclonal and polyclonal antibodies such as monoclonal antibody MoAb34 (Schneider et al., supra, 1997); F(ab')$_2$ fragments; and "miniantibodies," which are functional analogs of bivalent whole antibodies that assemble in E. coli. A miniantibody includes two scFv fragments linked to a dimerization domain via a hinge region, such as the murine IgG3 long upper hinge. Useful dimerization domains include anti-parallel amphipathic helices, arranged as a helix-turn-helix bundle (dHLX; see, for example, Borrebaeck, supra, 19.95). One skilled in the art can screen for bivalent antibody EPO analogs using routine assays. A primary screen can be an ELISA utilizing, for example, immobilized EPO receptor extracellular domain (EPObp), and a secondary screen for EPO agonist activity can be, for example, a thymidine uptake proliferation assay using a cell line stably expressing EPO receptor (Schneider et al., supra, 1997).

Anti-EPO receptor antibodies can be prepared, for example, using as an immunogen an EPO receptor fusion protein or a synthetic peptide encoding a portion of the EPO receptor extracellular domain. One skilled in the art understands that purified EPO receptor or an extracellular domain thereof, including peptide portions such as synthetic peptides, can be produced recombinantly and used as immunogens. Furthermore, non-immunogenic fragments or synthetic peptides of an EPO receptor can be made immunogenic by coupling the hapten to a carrier molecule such as bovine serum albumin (BSA) or keyhole limpet hemocyanin (KLH) by well known methods as described, for example, by Harlow and Lane, *Antibodies: A Laboratory Manual* (Cold Spring Harbor Laboratory Press, 1988).

An EPO analog also can be a small molecule drug that can induce EPO receptor dimerization and mimic one or more biological activities of naturally occurring erythropoietin. A small molecule EPO analog can contain, for example, eight copies of N-3-[2-(4-biphenyl)-6-chloro-5-methyl]indoylacetyl-L-lysine methyl ester, for example, attached to a polyamidoamino-octa-4-hydroxymethylbenzamide support via a chemical linker and can be prepared as described in Qureshi et al., *Proc. Natl. Acad. Sci., USA* 96:12156-12161 (1999). Additional small molecule EPO analogs can be routinely identified, for example, by screening compound libraries for molecules able to induce dimerization of soluble EPO receptor. Convenient assays for dimerization include assaying for retention of labeled recombinant EPO-binding protein (rEBP), which is the extracellular domain of the EPO receptor, to unlabeled rEMP immobilized on a plate in the presence of test compound (see Qureshi et al., supra, 1999).

Native erythropoietin is heavily glycosylated, and EPO prepared from Chinese hamster ovary (CHO) cells has three N-linked and one O-linked glycosylation sites with the average carbohydrate content being about 40%. In native EPO, carbohydrate plays an important role in stability, biosynthesis, apical secretion and biological activity. In particular, glycosylation appears to increase both conformational stability and solubility of EPO, although conformation is not affected. Thus, an EPO analog also can be a form of EPO that is hyper-glycosylated compared to native human EPO. Such analogs are known in the art and include, without limitation, Darbepoietin.

An EPO analog also can be a nucleic acid molecule encoding erythropoietin or an active fragment or analog thereof. An exemplary nucleic acid analog of human EPO is provided herein as SEQ ID NO: 1 (see FIG. 1). The skilled person understands that a nucleic acid molecule encoding an active fragment of EPO or a peptide analog of EPO such as one of those described hereinabove also can be an EPO analog useful in the methods of the invention.

As used herein, the term nucleic acid molecule means any polymer of two or more nucleotides, which are linked by a covalent bond such as a phosphodiester bond, a thioester bond, or any of various other bonds known in the art as useful and effective for linking nucleotides. A nucleic acid molecule can be linear, circular or supercoiled, and can be single stranded or double stranded. A nucleic acid molecule can be, for example, DNA or RNA, or a DNA/RNA hybrid.

A nucleic acid EPO analog, including a sense or antisense nucleic acid molecule or oligonucleotide, also can contain one or more nucleotide analogs or phosphothioate bonds, which protect against degradation by nucleases. A ribonucleotide containing a 2-methyl group, instead of the normal hydroxyl group, bonded to the 2'-carbon atom of ribose residues, is an example of a non-naturally occurring RNA molecule that is resistant to enzymatic and chemical degradation. Other examples of non-naturally occurring organic molecules include RNA containing 2'-aminopyrimidines, such RNA being 1000× more stable in human serum as compared to naturally occurring RNA (see Lin et al., *Nucl. Acids Res.* 22:5229-5234 (1994); and Jellinek et al., *Biochemistry* 34:11363-11372 (1995)).

Additional nucleotide analogs also are well known in the art and can be useful, for example, in an EPO analog. For example, RNA molecules containing 2'-O-methylpurine substitutions on the ribose residues and short phosphorothioate caps at the 3'- and 5'-ends exhibit enhanced resistance to nucleases (Green et al., *Chem. Biol.* 2:683-695 (1995)). Similarly, RNA containing 2'-amino-2'-deoxypyrimidines or 2'-fluoro-2'-deoxypyrimidines is less susceptible to nuclease activity (Pagratis et al., *Nature Biotechnol.* 15:68-73 (1997)). Furthermore, L-RNA, which is a stereoisomer of naturally occurring D-RNA, is resistant to nuclease activity (Nolte et al., *Nature Biotechnol.* 14:1116-1119 (1996)); Klobmann et al., *Nature Biotechnol.* 14:1112-1115 (1996)). Such RNA molecules and methods of producing them are well known and routine in the art (see Eaton and Piekern, *Ann. Rev. Biochem.* 64:837-863 (1995)). DNA molecules containing phosphorothioate linked oligodeoxynucleotides are nuclease-resistant and can be useful EPO analogs (Reed et al., *Cancer Res.* 50:6565-6570 (1990)). Phosphorothioate-3' hydroxypropylamine modification of the phosphodiester bond also reduces the susceptibility of a DNA molecule to nuclease degradation (see Tam et al., *Nucl. Acids Res.* 22:977-986 (1994)). Furthermore, thymidine can be replaced with 5-(1-pentynyl)-2'-deoxoridine (Latham et al., *Nucl. Acids Res.* 22:2817-2822 (1994)).

Viral vectors can be particularly useful for introducing a nucleic acid analog into a neuronal cell or neuronal precursor cell in a method of the invention. Such vectors include, for example, retroviral vectors, lentiviral vectors, adenoviral vectors, adeno-associated vectors (AAV) and herpesvirus vectors (see, for example, Kaplitt and Loewy, *Viral Vectors: Gene Therapy and Neuroscience Applications* Academic Press, San Diego, Calif. (1995); Chang, *Somatic Gene Therapy* CRC Press, Boca Raton, Fla. (1995)). Lentiviral, retroviral and adeno-associated vectors can be useful, for example, for permanent expression, and adenovirus and herpesvirus can be used to achieve transient expression lasting for several months to about one year. It is understood that both permanent and transient expression can be useful in the methods of the invention.

A variety of techniques are known in the art for introducing a nucleic acid molecule into a neuronal cell or neuronal precursor cell. Such methods include microinjection, electroporation, lipofection, calcium-phosphate mediated transfection, DEAE-Dextran-mediated transfection, polybrene- or polylysine-mediated transfection, and conjugation to an antibody, gramacidin S, artificial viral envelope or other intracellular carrier such as TAT. See Cibelli et al., Nat. Biotech. 16:642-646 (1998); Lamb and Gearhart, *Cur. Opin. Gen. Dev.* 5:342-348 (1995); Choi (U.S. Pat. No. 6,069,010); and *Current Protocols in Molecular Bioloqy*, John Wiley and Sons, pp 9.16.4-9.16.11 (2000).

The biological effects of erythropoietin also can be mimicked by a constitutively active EPO receptor, which is another EPO analog that can produce acute neuroprotective benefits according to a method of the invention. As used herein, the term "constitutive EPO receptor" is synonymous with "constitutively active EPO receptor" and means a polypeptide having structural similarity to the native human erythropoietin receptor and which has one or more hormone-independent biological activities of the native EPO receptor. Such a constitutive EPO receptor can have a modified dimerization interface such that the receptor dimerizes in the absence of ligand. In one embodiment, the constitutive EPO receptor is a variant of the native human EPO receptor which has an arginine to cysteine mutation at position 129 and which forms disulfide-linked homodimers in the absence of EPO. In other embodiments, a constitutive EPO receptor is a variant of a native EPO receptor containing one or more non-naturally occurring cysteines within the dimerization interface (see, for example, Watowich et al., supra, 1992; Watowich et al., supra, 1994; and Longmore et al., supra, 1994).

An EPO analog also can be a molecule that induces or enhances the intracellular signal transduction cascade of the EPO receptor. Signal is initiated following binding of EPO ligand and results in dimerization of receptor. JAK2 is autophosphorylated and subsequently phosphorylates the EPO receptor and STAT proteins, which then are free to translocate to the nucleus and activate transcription. In addition, cross talk between the JAK2 and NF-$\kappa$B signaling pathways, as well as Akt and bcl-$X_L$ upregulation, can lead to neuroprotection (Digicaylioglu and Lipton, *Nature* 412:641-647 (2001)). Hematopoietic cell phosphatase (HCP), also known as SHP1 or PTP1C, binds to phosphorylated EPO receptor and dephosphorylates JAK2, thereby acting as a negative regulator of the EPO receptor intracellular pathway. Thus, an EPO analog also can be an inhibitor of HCP such as an HCP antisense molecule. HCP inhibitors are known in the art and further can be identified by routine methods (Barbone et al., *Nephrol. Dial. Transplant.* 14[Suppl. 2]:80-84 (1999)).

Naturally occurring human IGF-I, also known as somatomedin C, is a hormone of 70 amino acids. IGF-I is a basic peptide (pI 8.4) with about 43% amino acid homology to proinsulin. Naturally occurring IGF-II is a relatively neutral peptide (pI 6.4) with 60% amino acid homology to native IGF-I.

The sequence of mature human IGF-I (SEQ ID NO: 6) is known in the art and is shown in FIG. 2 (Rotwein et al., *J. Biol. Chem.* 261:4828-4832 (1986); and Jansen et al., *Nature* 306: 609-611 (1983)). The 70 amino acids that make up mature human IGF-I have been divided into four principle domains. The first 29 residues of IGF-I bear a strong resemblance to the B chain of insulin and are therefore denoted the "B domain." Similarly, IGF-I residues 42-62 are homologous to the insulin A chain and are consequently denoted the "A domain." Intervening between the B and A domains (residues 30-41) is the "C domain;" the carboxy-terminal 7 amino acids (residues 63-70) are known as the "D domain."

NMR solution structure of the core of human IGF-I shows striking similarity to insulin (Cooke et al., Biochem. 30:5484-5491 (1991)), and IGF-I is known to bind the insulin receptor, although with lower affinity than to the IGF type I receptor. Consistent with this model, the IGF-I C and D domains may be "flaps," which flank the insulin-conserved receptor binding cleft, and which contribute to specific binding to the type 1 receptor. Mutagenesis experiments have revealed that residues in the carboxy-terminal extended region of the B domain and residues in the C domain proximal to the B domain are involved in receptor binding, and that tyrosines 24 and 31 are involved in specific receptor interactions.

Unlike most other growth factors, the IGFs are present in high concentrations in the circulation; however, only a relatively small fraction is available in a "free" or unbound form. Specific binding proteins of high molecular weight and with a high binding capacity for IGF-I and IGF-II act as carrier proteins and modulate IGF functions (Holly et al., Endocrin. 118:7-18 (1988)). Most IGFs in blood circulate as part of a non-covalently associated ternary complex made up of IGF-I or IGF-II, IGFBP-3 and a protein known as the "acid-labile subunit" (ALS).

As used herein, the term "insulin-like growth factor" is synonymous with "IGF" and means a polypeptide that has substantially the amino acid sequence of naturally occurring human IGF-I or naturally occurring human IGF-II or a homolog of one of these proteins. Insulin-like growth factors useful in the invention include human and other primate IGFs, mammalian IGFs such as bovine, porcine, murine and rat homologs, and other vertebrate homologs such as chicken and *Danio rerio* homologs. Thus, the term IGF encompasses species homologs, alternatively spliced forms, isotype variants and precursors of the mature human IGF-I sequence shown in FIG. 2, and species homologs, alternatively spliced forms, isotype variants and precursors of mature human IGF-II. An IGF-I generally has an amino acid sequence with at least about 80% amino acid identity to the sequence of naturally occurring mature human IGF-I (SEQ ID NO: 6) and can have, for example, 90% or 95% or more amino acid identity with SEQ ID NO: 6. Similarly, an IGF-II generally has an amino acid sequence with at least about 80% amino acid identity to the sequence of naturally occurring mature human IGF-II and can have 90% or 95% or more amino acid identity with mature human IGF-II. It is understood that an IGF useful in the invention can be obtained by a variety of well known methods, including, without limitation, purification from a natural source, recombinant expression, and peptide or chemical synthesis. As an example, IGF-I can be prepared in bacteria as a fusion peptide, followed by subsequent cleavage of the fusion product as described, for example, in U.S. Pat. No. 5,708,134.

An active fragment of an IGF also can be useful in the invention. An active fragment has an amino acid sequence corresponding to a portion of full-length IGF-I or IGF-II and retains the ability to synergize with EPO to produce an acute neuroprotective effect. Active fragments of IGF-I and IGF-II useful in the invention include fragments with similar activity or with improved activity or stability relative to the naturally occurring full-length IGF. As a non-limiting example, such an active fragment can lack the first 1 to 5 amino terminal residues of IGF-I. Destripeptide IGF-I, which lacks the native N-terminal residues Gly Pro Glu, stimulates protein and DNA synthesis at concentrations between 4 and 50-fold lower than the levels required for full-length IGF-I. The elimination of 1 to 5 amino acids from the N-terminus of bovine or porcine IGF-I also results in enhanced potency. These and other active fragments of IGF-I find use in the methods of the invention.

A method of the invention can be practiced, if desired, with an "IGF analog." As used herein, the term "IGF analog" means a molecule that induces or enhances expression, activity or intracellular signaling of the type 1 insulin-like growth factor receptor and that, in combination with EPO, produces a synergistic acute neuroprotective effect in neurons. Such an IGF analog can be, without limitation, a protein, peptide, peptidomimetic, small molecule, ribozyme, nucleic acid molecule, oligonucleotide, oligosaccharide, cell, phage or virus, or a combination thereof. It is understood that the term IGF analog encompasses active fragments of IGF-I and IGF-II.

IGF analogs include molecules with improved characteristics relative to native human IGF-I or IGF-II, for example, that facilitate commercial production of the analog; that have improved potency, size, stability or solubility; or that provide a more desirable pharmaceutical formulation. As non-limiting examples, more active IGF analogs can be produced, for example, by a modification affecting the interaction of the IGF with its receptor, an IGF-binding protein (IBP) or heparin.

An IGF analog can be a molecule retaining IGF activity but having reduced affinity for one or more serum components, as described, for example, in Applebaum et al. (U.S. Pat. No. 4,876,242). Such an analog can have equal potency relative to IGF-I at the type I IGF receptor and can display, for example, a 5- to 10-fold increase in activity relative to human IGF-I. As an example, an IGF analog can be a 71 amino acid analog of human IGF-I containing the first 17 residues of the B chain of human insulin in place of the first 16 residues of human IGF-I or another analog incorporating a portion of insulin in place of the native IGF sequence (see, also, Cascieri and Bayne in LeRoith and Raizada, *Current Directions in Insulin-like Growth Factor Research* Plenum Press: New York 1994). An IGF analog also can be a peptide or peptidomimetic analog with a non-naturally occurring amino-terminal sequence. Ballard et al. (U.S. Pat. Nos. 5,470,828 and 5,164,370) describe IGF-I and IGF-II analogs where there is a substitution of Glu3 in IGF-I, or a substitution of Glu5 and Glu6 in IGF-II. The one or more glutamic acid residues can be substituted, without limitation, with Ala, Asn, Phe, Ile, Met, Val, Ser, Pro, Thr, Tyr or Cys. If desired, at least one of the surrounding Gly, Pro or Thr residues also can be absent from the IGF analog.

While naturally occurring IGFs are single chain molecules, an IGF analog can have two or more chains. Two-chain IGF analogs include disulfide-bonded heterodimers composed of a first chain containing the B and C domains, and a second chain containing the A domain. Such a two-chain IGF analog can be an IGF-I analog in which the C domain contains a deletion of the first 8, 10 or 12 residues and can have increased IGF-I activity as compared to native human IGF-I (see, for example, U.S. Pat. No. 5,622,932).

An IGF pathway also can be induced using a molecule which increases the active concentration of an IGF, for example, by inhibiting the interaction of IGF-I or IGF-II with one of their binding proteins but not with the type 1 IGF receptor; such an IGF analog can be used alone or in combination with IGF-I or IGF-II, or an active fragment or analog thereof. Such IGF analogs, which can be a small antagonist mimetics of an IGF binding protein acting as indirect agonists, include peptides and peptidomimetics such as those shown in Table 2. These molecules are well known in the art as described, for example, in U.S. Pat. No. 6,251,865 and Lowman et al., *Biochemistry* 37:8870-8878 (1998).

TABLE 2

| Peptide sequence | SEQ ID NO: |
| --- | --- |
| ASEEVCWPVAEWYLCNMWGR | 13 |
| ASEEVCWPVAEWYLC | 14 |
| GPETCWPVAEWYLCN | 15 |
| EEVCWPVAEWYLCN | 16 |
| EVCWPVAEWYLCN | 17 |
| CWPVAEWYLCN | 18 |
| CPAGPLQWLCEKYFG | 19 |
| SEVGCRAGPLQWLCEKYFG | 20 |

Additional IGF analogs useful in the invention include but are not limited to LR3IGF-I, which contains an Arg for Glu substitution at position 3 and a 13 residue amino-terminal extension (Francis et al., *J. Mol. Endocrinol.* 8:213-223 (1992)) as well as forms containing [Leu24] or [Leu24] [Arg31] (Bayne et al., *J. Biol. Chem.* 265:15648-15652 (1990); Seigel et al., *Molecular Vision* 6:157-163 (2000)), and the $Val_{59}$ IGF-I analog that simplifies production through application of cyanogen bromide (Ueda et al., U.S. Pat. No. 4,745,179).

An IGF analog also can be a nucleic acid molecule that, for example, encodes IGF-I or IGF-II or an active fragment or analog thereof. An exemplary nucleic acid analog of human IGF-I is provided herein as SEQ ID NO: 4. The skilled person understands that a nucleic acid molecule encoding an active fragment of IGF-I or IGF-II, or a peptide analog thereof, such as those described hereinabove also can be a nucleic acid analog of IGF-I or IGF-II useful in the methods of the invention.

Additional IGF analogs can be identified, if desired, by routine methods. As an example, a kinase receptor activation assay (KIRA) can be used to measure activation of the human type I IGF-I receptor and thereby identify an IGF analog as described in Lowman et al., *Biochemistry* 37:8870-8878 (1998). Briefly, human MCF-7 cells (ATCC-HTB 22), which express IGF and insulin receptors, are grown overnight in 96 well plates with 50/50 F12/DMEM medium (Gibco) at 37° C. in 5% C02. Supernatants are decanted, and stimulation media (50/50 F12/DMEM with 25 mM HEPES and 2.0% BSA) containing either test compound or recombinant human IGF-I standards are added. After stimulation at 37° C. for 15 minutes, supernatants are decanted, and the cells lysed. Lysates are transferred to an immunosorbant plate coated with polyclonal anti-IGF-I receptor (Santa Cruz Biotechnology) and blocked with BSA. After incubation for two hours at room temperature, unbound receptor is removed by washing, and bound receptor detected with biotinylated antibody 4G10 (anti-phosphotyrosine), followed by development with HRP-conjugated dextran-streptavidin and tetramethylbenzidine substrate solution. The product absorbance is read at 450 nm with a reference at 650 nm.

An EPO or IGF analog useful in the invention also can be a bifunctional molecule such as a biofunctional peptide having the activity of EPO as well as an IGF. It is understood that such a chimeric EPO/IGF peptide, which has the activity of both EPO and an IGF, can be used in the methods of the invention in the absence of additional EPO or IGF or an active fragment or analog thereof or, if desired, in combination with one or both of EPO or IGF or active fragments or analogs thereof. Thus, while in many cases, the methods of the invention are practiced by contacting neuronal cells or administering a combination of two factors (EPO and an IGF), the methods of the invention also can be practiced by contacting neuronal cells with or by administering to a subject a single bifunctional analog in place of individual EPO and IGF proteins or active fragments or analogs thereof. In one embodiment, the invention is practiced by contacting neuronal cells with an EPO/IGF bifunctional analog which is cleaved after uptake into the neuronal cells to produce individual EPO and IGF analogs. In another embodiment, the invention is practiced by administering to a subject an EPO/IGF bifunctional analog, which is cleaved subsequent to administration to produce individual EPO and IGF analogs.

Peptide analogs can be synthesized by well known methodology, for example, utilizing an Applied Biosystems 430A Peptide Synthesizer (Foster City, Calif.). Boc amino acid resins and other reagents can be obtained from Applied Biosystems and other commercial sources. Sequential Boc chemistry, using double couple protocols and acetic anhydride capping can be applied to the desired Boc-amino acid-4-(oxymethyl)phenylacetamidomethyl [PAM] resin. Asparagine, histidine, glutamine, arginine, α-p-hydroxyphenyl) acetic acids, β-p-hydroxyphenyl proprionic acids, p-hydroxybenzoic acids, p-hydroxycinnamic acids and p-hydroxyphenoxy acetic acids can be coupled using preformed hydroxy benzotrizole esters. Other residues can be conveniently coupled using preformed symmetrical anhydrides with dicyclocarbodiamide (DCC). Recombinant hormones and active fragments and analogs thereof also can be prepared using recombinant methods in prokaryotic host cells or in yeast or other eukaryotic host cells as described, for example, in U.S. Pat. No. 5,104,796 and U.S. Pat. No. 5,084,384 (see, also, U.S. Pat. No. 5,622,932). It is understood that recombinant forms of EPO or IGF can be prepared as fusion proteins and can contain additional heterologous sequences such as signal sequences.

The present invention also provides a method of preventing or reducing the severity of an acute neurologic condition in a subject by administering to the subject EPO or an active fragment or analog thereof close to or subsequent to the time of acute injury; and administering to the subject an IGF or an active fragment or analog thereof close to or subsequent to the time of acute injury, thereby providing a synergistic acute neuroprotective effect and preventing or reducing the severity of the acute neurologic condition. Such an acute neurologic condition can be, without limitation, stroke, head or spinal cord trauma, or seizure.

A method of the invention for preventing or reducing the severity of an acute neurologic condition can be practiced, for example, with EPO or an active fragment thereof, such as human EPO or an active fragment thereof. A method of the invention also can be practiced with an EPO analog, which can be, without limitation, a peptide, peptidomimetic, small molecule or nucleic acid analog. In particular embodiments, the invention is practiced with an EPO analog containing one of the following amino acid sequences: GGTYSCHFG-PLTWVCKPQGG (SEQ ID NO: 7); GGDYHCRMG-PLTWVCKPLGG (SEQ ID NO: 8); GGVYACRMGPIT-WVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In one embodiment, the invention is practiced with EPO or an active fragment or analog thereof which has at least 10-fold higher affinity for the EPO receptor than native human EPO. In another embodiment, the invention is practiced with EPO or an active fragment or analog thereof which is oligomeric, for example, dimeric. As an example, a method of the invention can be practiced with a dimeric form of EPO in which each monomer contains the amino acid sequence GGTYS<u>CHFGPLTWVC</u>KPQGG (SEQ ID NO: 7). In a further embodiment, the invention is practiced with EPO or an active fragment or analog thereof which has a half-life greater than the half-life of native human EPO. Such a form of EPO can be hyper-glycosylated as compared to native human EPO and further can be, for example, Darbepoietin. The methods of the invention also optionally include the step of administering soluble EPO receptor to the subject.

A variety of forms of IGF and active fragments and analogs thereof are useful in the invention. In one embodiment, the invention is practiced by administering IGF or an active fragment thereof, for example, IGF-I or an active fragment thereof. In an additional embodiment, the invention is practiced by administering human IGF-I or an active fragment thereof. The invent-ion also can be practiced by administering an IGF analog such as a peptide, peptidomimetic, small molecule or nucleic acid analog including, but not limited to, a variety of IGF-I analogs.

In one embodiment, a method of the invention for preventing or reducing the severity of an acute neurological condition is practiced with an IGF or active fragment or analog thereof which has at least 10-fold higher affinity for the IGF-I receptor than native human IGF-I. In another embodiment, the invention is practiced with an IGF or active fragment or analog thereof which has an altered affinity for an IGF-binding protein. In a further embodiment, the invention is practiced with an IGF or active fragment or analog thereof which has a half-life greater than the half-life of native human IGF. In the methods of the invention, EPO and IGF, or active fragments or analogs thereof, can be administered simultaneously or in any order and in the same or different pharmaceutical compositions.

As used herein, the term "subject" means any animal containing neurons, for example, a mammal such as a mouse, rat, dog, primate or human. A subject typically suffers from an acute or chronic neurologic condition or is at high risk of developing a neurologic condition.

As used herein, the term "acute neurological condition" means any neurological disorder or disease having a short and relatively severe course. As non-limiting examples, an "acute neurologic condition" can be cerebral ischemia associated with stroke; hypoxia; anoxia; poisoning by carbon monoxide, manganese or cyanide; hypoglycemia; perinatal asphyxia; near death drowning; mechanical trauma to the nervous system such as trauma to the head or spinal cord; epileptic seizure; cardiac arrest; or cerebral asphyxia associated, for example, with coronary bipass surgery. Acute neurological conditions generally are distinguished from chronic neurological conditions, in which the neurological condition is of a relatively long duration, for example, several months or years.

Also provided by the invention is a method of preventing or reducing the severity of a neurologic condition in a subject by administering to the subject EPO or an active fragment or analog thereof at a dose of at most 2000 U/kg; and administering to the subject an IGF or an active fragment or analog thereof, thereby providing neuroprotection and preventing or reducing the severity of the neurologic condition. The EPO and IGF, or active fragments or analogs thereof, can be administered to the subject simultaneously or in any order and in the same or different pharmaceutical compositions using any of a variety of routes of administration including, without limitation, oral, intravenous, intraperitoneal, subcutaneous, intracerebroventricular, intrathecal, transnasal, intravitreal and transcleral administration. A variety of acute and chronic neurologic conditions can be treated according to a method of the invention including, but not limited to, Alzheimer's disease, Parkinson's disease, Huntington's disease, amyotrophic lateral sclerosis, multiple sclerosis, HIV-associated dementia, glaucoma, epilepsy, light-induced retinal degeneration such as photoreceptor degeneration, macular degeneration, and pain.

The present invention also provides a method of preventing or reducing the severity of a cerebral neurologic condition in a subject by transnasally administering to the subject EPO or an active fragment or analog thereof at a dose of at most 2000 U/kg; and transnasally administering to the subject an IGF or an active fragment or analog thereof, thereby providing acute neuroprotection and preventing or reducing the severity of the neurologic condition.

Various forms of EPO and active fragments and analogs thereof are useful for preventing or reducing the severity of a neurologic condition according to a method of the invention. As an example, the invention can be practiced with EPO or an active fragment thereof such as human EPO or an active fragment thereof. A method of the invention also can be practiced with an EPO analog, which can be, without limitation, a peptide, peptidomimetic, small molecule or nucleic acid analog. In particular embodiments, the invention is practiced with an EPO analog containing one of the following amino acid sequences: GGTYSCHFGPLTWVCKPQGG (SEQ ID NO: 7); GGDYHCRMGPLTWVCKPLGG (SEQ ID NO: 8); GGVYACRMGPITWVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In one embodiment, a method of the invention for preventing or reducing the severity of a neurologic condition is practiced with EPO or an active fragment or analog thereof which has at least 10-fold higher affinity for the EPO receptor than native human EPO. In another embodiment, the invention is practiced with EPO or an active fragment or analog thereof which is oligomeric, for example, dimeric. The invention can be practiced, for example, with a dimeric form of EPO in which each monomer contains the amino acid sequence GGTYS<u>CHFGPLTWVC</u>KPQGG (SEQ ID NO: 7). In a further embodiment, the invention is practiced with EPO or an active fragment or analog thereof which has a half-life greater than the half-life of native human EPO. Such a form of EPO can be hyper-glycosylated as compared to native human EPO and further can be, for example, Darbepoietin. The methods of the invention further optionally include the step of administering soluble EPO receptor to the subject.

A variety of forms of IGF and active fragments and analogs thereof also are useful in the invention. In one embodiment, the invention is practiced by administering an IGF or an active fragment thereof, for example, IGF-I or an active fragment thereof. In an additional embodiment, the invention is practiced by administering human IGF-I or an active fragment thereof. In a further embodiment, the invention is practiced by administering an IGF analog such as a peptide, peptidomimetic, small molecule or nucleic acid analog including, but not limited to, a variety of IGF-I analogs.

In one embodiment, a method of the invention for preventing or reducing the severity of a neurological condition is practiced with an IGF or active fragment or analog thereof which has at least 10-fold higher affinity for the IGF-I receptor than native human IGF-I. In another embodiment, the invention is practiced with an IGF or active fragment or analog thereof which has an altered affinity for an IGF-binding protein. In a further embodiment, the invention is practiced with an IGF or active fragment or analog thereof which has a half-life greater than the half-life of native human IGF.

The term "neurological condition" as used herein, encompasses all acute and chronic neurological conditions. Thus, neurological conditions encompass, without limitation, hypoxia-ischemia (stroke); head or spinal cord injury; epilepsy; neurodegenerative disorders such as Parkinson's disease, Huntington's disease, Alzheimer's disease, amyotrophic lateral sclerosis or multiple sclerosis; optic neuropathies such as glaucoma., light-induced retinal degeneration such as photoreceptor degeneration, and macular degeneration; disorders of photoreceptor degeneration such as retinitis pigmentosa; metabolic, mitochondrial and infectious brain abnormalities such as encephalitis; and neuropathic pain (Lipton and Rosenberg, *New Enql. J. Med.* 330: 613 (1994)). Chronic neurological conditions encompass neurodegenerative diseases such as Alzheimer's disease, Huntington's disease; disorders of photoreceptor degeneration such as retinitis pigmentosa and light-induced retinal degeneration; macular degeneration of the retina; forms of dementia including fronto-temporal dementia and HIV-associated dementia (acquired immunodeficiency syndrome dementia complex); neuropathic pain syndromes such as causalgia or painful peripheral neuropathies and other chronic pain syndromes; olivopontocerebellar atrophy; Parkinson's disease; Parkinsonism; amyotrophic lateral sclerosis; mitochondrial abnormalities and other biochemical disorders such as MELAS syndrome, MERRF, Leber's disease, Wernicke's encephalopathy, Rett syndrome, homocysteinuria, hyperhomocysteinemia, hyperprolinemia, nonketotic hyperglycinemia, hydroxybutyric aminoaciduria, sulfite oxidase deficiency, combined systems disease, lead encephalopathy; hepatic encephalopathy, Tourette's syndrome; drug addiction, tolerance, dependency; and depression or anxiety syndromes.

The methods of the invention for preventing or reducing the severity of a neurologic condition in a subject are based, in part, on the discovery that, when administered in conjunction with an IGF such as IGF-I, EPO can be neuroprotective at much lower doses than previously observed. Thus, the methods of the invention are practiced by administering a dose of at most 2000 U/kg EPO, or active fragment or analog thereof. In particular embodiments, the invention is practiced by administering a dose of at most 1500 U/kg, 1000 U/kg, 750 U/kg, 500 U/kg, 250 U/kg, 100 U/kg, 90 U/kg, 80 U/kg, 70 U/kg, 60 U/kg, 50 U/kg, 40 U/kg, 30 U/kg, 20 U/kg, 10 U/kg, 5 U/kg, 2.5 U/kg or 1 U/kg EPO or active fragment or analog thereof. In further embodiments, the invention is practiced by administering at most 2000 U/kg/day, 1500 U/kg/day, 1000 U/kg/day, 750 U/kg/day, 500 U/kg/day, 250 U/kg/day, 100 U/kg/day, 90 U/kg/day, 80 U/kg/day, 70 U/kg/day, 60 U/kg/day, 50 U/kg/day, 40 U/kg/day, 30 U/kg/day, 20 U/kg/day, 10 U/kg/day, 5 U/kg/day, 2.5 U/kg/day or 1 U/kg/day EPO or active fragment or analog thereof. In still further embodiments, a method of the invention for preventing or reducing the severity of a neurologic condition in a subject is practiced by administering EPO, or active fragment or analog thereof, in the range of 0.5 U/kg/day to 200 U/kg/day, 0.5 U/kg/day to 100 U/kg/day, 0.5 U/kg/day to 50 U/kg/day, 0.5 U/kg/day to 25 U/kg/day, 0.5 U/kg/day to 15 U/kg/day, 0.5 U/kg/day to 10 U/kg/day, 0.5 U/kg/day to 5 U/kg/day, 1 U/kg/day to 200 U/kg/day, 1 U/kg/day to 100 U/kg/day, 1 U/kg/day to 50 U/kg/day, 1 U/kg/day to 25 U/kg/day, 1 U/kg/day to 15 U/kg/day, 1 U/kg/day to 10 U/kg/day, 1 U/kg/day to 5 U/kg/day, 2 U/kg/day to 200 U/kg/day, 2 U/kg/day to 100 U/kg/day, 2 U/kg/day to 50 U/kg/day, 2 U/kg/day to 25 U/kg/day, 2 U/kg/day to 15 U/kg/day, 2 U/kg/day to 10 U/kg/day, 2 U/kg/day to 5 U/kg/day, 3 U/kg/day to 200 U/kg/day, 3 U/kg/day to 100 U/kg/day, 3 U/kg/day to 50 U/kg/day, 3 U/kg/day to 25 U/kg/day, 3 U/kg/day to 15 U/kg/day, 3 U/kg/day to 10 U/kg/day, 3 U/kg/day to 5 U/kg/day, 5 U/kg/day to 200 U/kg/day, 5 U/kg/day to 100 U/kg/day, 5 U/kg/day to 50 U/kg/day, 5 U/kg/day to 25 U/kg/day, 5 U/kg/day to 15 U/kg/day, or 5 U/kg/day to 10 U/kg/day. In still further embodiments, a method of the invention for preventing or reducing the severity of a neurologic condition in a subject is practiced by administering EPO, or active fragment or analog thereof, at 3 U/kg/day, 5 U/kg/day, 10 U/kg/day, 15 U/kg/day, 20 U/kg/day or 25 U/kg/day. A unit of EPO, as defined by the World Health Organization and as used herein, is the equivalent of 1.2 international units of EPO activity.

The methods of the invention additionally involve administering an IGF or active fragment or analog thereof to the subject. Such an IGF or active fragment or analog thereof generally is administered to a subject at from 0.5 ng/kg/day to 500 ng/kg/day. In particular embodiments, a method of the invention is practiced by administering an IGF such as IGF-I, IGF-II or an active fragment of analog of one of these factors, in a range of 1 ng/kg/day to 500 ng/kg/day, 1 ng/kg/day to 250 ng/kg/day, 1 ng/kg/day to 100 ng/kg/day, 1 ng/kg/day to 50 ng/kg/day, 1 ng/kg/day to 20 ng/kg/day, 1 ng/kg/day to 10 ng/kg/day, 5 ng/kg/day to 500 ng/kg/day, 5 ng/kg/day to 250 ng/kg/day, 5 ng/kg/day to 100 ng/kg/day, 5 ng/kg/day to 50 ng/kg/day, 5 ng/kg/day to 20 ng/kg/day, 5 ng/kg/day to 10 ng/kg/day, 10 ng/kg/day to 500 ng/kg/day, 10 ng/kg/day to 250 ng/kg/day, 10 ng/kg/day to 100 ng/kg/day, 10 ng/kg/day to 50 ng/kg/day, 10 ng/kg/day to 20 ng/kg/day, 20 ng/kg/day to 500 ng/kg/day, 20 ng/kg/day to 250 ng/kg/day, 20 ng/kg/day to 100 ng/kg/day, 20 ng/kg/day to 50 ng/kg/day; 20 ng/kg/day to 50 ng/kg/day, 30 ng/kg/day to 500 ng/kg/day, 30 ng/kg/day to 250 ng/kg/day, 30 ng/kg/day to 100 ng/kg/day, 30 ng/kg/day to 50 ng/kg/day, 50 ng/kg/day to 500 ng/kg/day, 50 ng/kg/day to 250 ng/kg/day or 50 ng/kg/day to 100 ng/kg/day. In other embodiments, a method of the invention is practiced by administering 5 ng/kg/day, 10 ng/kg/day, 20 ng/kg/day, 25 ng/kg/day, 30 ng/kg/day or 50 ng/kg/day of an IGF or active fragment or analog thereof.

In further embodiments, a method of the invention is practiced by administering EPO, or an active fragment or analog thereof, in a range of 1 U/kg/day to 100 U/kg/day, 1 to 50 U/kg/day, 1 U/kg/day to 15 U/kg/day, 2 U/kg/day to 100 U/kg/day, 2 U/kg/day to 50 U/kg/day, 2 U/kg/day to 15 U/kg/day, 3 U/kg/day to 100 U/kg/day, 3 U/kg/day to 50 U/kg/day, or 3 U/kg/day to 15 U/kg/day in combination with an IGF, or active fragment or analog thereof, administered in a range of 1 ng/kg/day to 500 ng/kg/day, 5 ng/kg/day to 200 ng/kg/day or 10 ng/kg/day to 100 ng/kg/day.

EPO, or an active fragment or analog thereof, and an IGF or an active fragment or analog thereof, generally are administered to a subject in a pharmaceutical composition. It is understood that the EPO and IGF can be administered in the same or separate pharmaceutical compositions and further can be administered simultaneously or in any order, and by the same or different routes of administration. A pharmaceutical composition useful in the invention includes EPO or an active fragment or analog thereof, or an IGF or an active fragment or analog thereof, or both, each in a concentration range of, for example, approximately 0.0001% to approximately 0.1% weight by volume but not to exceed 2000 U/kg EPO or active fragment or analog thereof. A pharmaceutical composition useful in the methods of the invention further can include an excipient well known in the art for preparing pharmaceutical compositions including compositions suitable for intranasal administration. Pharmaceutical compositions useful in the invention further encompass, without limitation, those containing carrier proteins such as albumin. As non-limiting examples, a pharmaceutical composition of the invention can include about 0.1% to 0.4% of a carrier protein such as albumin.

A pharmaceutical composition includes a pharmaceutically acceptable carrier, which is any carrier that has substantially no long term or permanent detrimental effect when administered. Examples of pharmaceutically acceptable carriers include, without limitation, water, such as distilled or deionized water; saline; and other aqueous media. It is understood that the active ingredients can be soluble or can be delivered as a suspension in a suitable carrier.

A preservative or tonicity adjustor can be included, if desired, in a pharmaceutical composition useful in the invention. Useful preservatives include, without limitation, benzalkonium chloride, chlorobutanol, thimerosal, phenylmercuric acetate, and phenylmercuric nitrate. Tonicity adjustors useful in the invention include salts such as sodium chloride, potassium chloride, mannitol or glycerin and other pharmaceutically acceptable tonicity adjustor.

Various buffers and means for adjusting pH can be-used to prepare a pharmaceutical composition useful in the invention, provided that the resulting preparation is pharmaceutically acceptable. Such buffers include, without limitation, acetate buffers, citrate buffers, phosphate buffers and borate buffers. It is understood that acids or bases can be used to adjust the pH of the composition as needed. Pharmaceutically acceptable antioxidants useful in the invention include, yet are not limited to, sodium metabisulfite, sodium thiosulfate, acetylcysteine, butylated hydroxyanisole and butylated hydroxytoluene.

A variety of routes of administration can be useful in the invention depending, in part, on the size and characteristics of the polypeptide or analog to be administered and the history, risk factors and symptoms of the subject to be treated. Routes of administration suitable for the methods of the invention include both systemic and local administration. In specific embodiments, EPO or an active fragment or analog thereof, is administered through oral, intravenous, subcutaneous, intraperitoneal, intravitreal, transcleral, intranasal, intrathecal or epidural administration, or via intracerebro ventricular injection or a shunt surgically inserted into the cerebro ventricle. In further embodiments, IGF-I or an active fragment or analog thereof, is administered orally, intravenously, intranasally, intrathecally, epidurally, or via cerebro ventricular injection or a shunt surgically inserted into the cerebro ventricle.

Routes of administration useful in the methods of the invention encompass, without limitation, oral delivery; intravenous injection; intramuscular injection; subcutaneous injection; intraperitoneal injection; transdermal diffusion and electrophoresis; topical eye drops and ointments; periocular and intraocular injection including subconjunctival injection; extended release delivery devices including locally implanted extended release devices including a bioerodible or reservoir-based implants. It is understood that an implant useful in the invention generally releases the implanted pharmaceutical composition over an extended period of time.

Intranasal administration can be useful in the methods of the invention for preventing or reducing the severity of a neurological condition that affects the brain. Such conditions include yet are not limited to cerebral ischemia; stroke; hypoxia or anoxia; mechanical trauma to the head; HIV-associated dementia (AIDs dementia complex); Alzheimer's disease or Parkinson's disease; and drug addiction, tolerance and dependency, as well as other neurological disorders that affect the brain described hereinabove or known in the art. In one embodiment, intranasal administration is used to deliver a peptide or peptidomimetic analog of EPO. In another embodiment, intranasal administration is used to deliver a peptide or peptidomimetic analog of IGF-I. In a further embodiment, intranasal administration is used to deliver a peptide or peptidomimetic analog of EPO and a peptide or peptidomimetic analog of IGF-I. In further embodiments, the peptide or peptidomimetic analogs of EPO administered intranasally have a length of up to 50 residues, 40 residues, 30 residues, 25 residues, 20 residues, 15 residues, 12 residues or 10 residues. In yet further embodiments, the peptide or peptidomimetic analogs of IGF administered intranasally have a length of up to 50 residues, 40 residues, 30 residues, 25 residues, 20 residues, 15 residues, 12 residues or 10 residues.

Intranasal administration of EPO or IGF-I, or a peptide or peptidomimetic of one of these factors, can bypass the blood-brain barrier and thereby deliver the therapeutic agent to the brain. As an example, Liu et al., *J. Neur. Sci.* 187:91-97 (2001), demonstrate that recombinant human IGF-I can protect against focal cerebral ischemic damage when administered intranasally. Intranasal administration can be accomplished by routine methods, for example, using a Rhinüle (Ferring; Germany) to blow a liquid substance containing the desired active ingredients into each nostril (Pietrowsky et al., *Biol. Psych.* 39:332-240 (1996)). The Rhinüle is a small, flexible tube with a tip on one end that allows one to deliver a defined volume of 0.2 ml of a liquid substance into a nostril. Additional means of intranasal administration, including the use of nose drops (Liu et al., supra, 2001), also are encompassed by the methods of the invention. Nasal formulations of EPO, IGF-I or both, can be prepared by routine methods. As an example, a nasal formulation of IGF-I can contain 0.1-10% IGF-1 and 0.05 to 2.0% by weight carboxyvinyl polymer.

Any of the methods of the invention can include the additional step of expressing in the neuronal cells, or in neuronal precursor cells as described further below, one or more nucleic acid molecules encoding gene products that are therapeutically useful. As an example, for treatment of Parkinson's disease, a neuronal cell or neuronal precursor cell can express, for example, a nucleic acid molecule encoding the catecholamine enzyme tyrosine hydroxylase, thereby increasing dopamineβ-hydroxylase activity upon intracerebral grafting (Jiao et al., *Nature* 362:450 (1993); see, also, Dhawan et al., *Science* 254: 1509 (1991); and Barr and Leiden, Science 254:1507 (1991)). Similarly, for treatment of Alzheimer's disease, a neuronal cell or neuronal precursor cell can express a nucleic acid molecule encoding nerve growth factor, thereby promoting cell survival of the cholinergic neurons that are typically lost in Alzheimer's disease (Rosenberg et al., *Science* 242:1575-1578 (1988)). In a similar manner, a neuronal cell or neuronal precursor cell can be engineered to express encephalin for treatment of neuropathic disorders involving intractable pain. One skilled in the art recognizes that these and other combinations are encompassed by the methods of the invention.

A neuronal cell or neuronal precursor cell further can be engineered to express one or more anti-apoptotic gene products including, without limitation, members of the Bcl-2 family such as Bcl-2 and Bcl-XL and members of the inhibitor of apoptosis (IAP) family such as c-IAP-1, c-IAP-2, XIAP or NIAP. ((Anderson, *Trends Pharm. Sci.* 18:51 (1997); Gross and et al., *Genes Dev.* 13:1899-1911 (1999); and Deveraux and Reed, *Genes Dev.* 13:239-252 (1999)).

In any of the methods of the invention, the neuronal cells or neuronal precursor cells optionally can be treated to promote cell survival. In one embodiment, mature neuronal cells are treated with a p38 inihibitor. In another embodiment, neuronal cells or neuronal precursor cells are treated to inhibit caspase activity. A variety of caspase inhibitors are useful in the invention including, for example, nucleic acids, polypeptides, peptides, peptidomimetics and non-peptide inhibitors such as small molecule drugs known in the art. As used herein, the term "caspase inhibitor" means any molecule that binds to and inhibits the activity of one or more caspases. Caspase inhibitors useful in the methods of the invention generally are cell permeable and have inhibitory activity in vivo and include viral and cellular gene products as well as synthetic inhibitors such as synthetic small molecules (Ekert et al., *Cell Death and Differentiation* 6:1081-1086 (1999)).

A caspase inhibitor can be a general (non-selective) caspase inhibitor or can be a selective caspase inhibitor. Selective inhibitors are those inhibitors which do not inhibit non-caspase cysteine proteases or serine proteases. Non-selective caspase inhibitors, which also inhibit one or more non-caspase protease inhibitors, include, for example, the cysteine protease inhibitor iodoacetamide. A caspase inhibitor also can be selective for one or more specific caspases. A caspase inhibitor can selectively inhibit caspase-3 or caspase-7 or a combination thereof and can be combined, for example, with any form of EPO or IGF or an active fragment or analog thereof disclosed herein or known in the art. Caspase inhibitors selective for caspases-3 and -7 include non-peptide inhibitors such as isatin sulfonamides (see, for example, Lee et al., *J. Biol. Chem.* 275:16007-16014 (2000)). A selective caspase inhibitor also can be selective for caspase-3, caspase-6, caspase-7 or caspase-8, or any combination thereof, and can be combined, for example, with any form of EPO and IGF.

A caspase inhibitor can be, for example, the cytokine response modifier A (CrmA) polypeptide, or an encoding nucleic acid molecule, which inhibits caspases -1 and -8; or the p35 baculovirus protein, or an encoding nucleic acid molecule, which inhibits caspases-1, -3, -6, -7, -8 and -10 but does not inhibit non-caspase cysteine proteases or serine proteases (Clem et al., *Science* 254:1388-1390 (1991)). A caspase inhibitor also can be an inhibitor of apoptosis protein (IAP) or an encoding nucleic acid molecule. IAPs useful as caspase inhibitors in a method of the invention include XIAP and Survivin.

A caspase inhibitor also can be a synthetic caspase inhibitor such as a pseudosubstrate which acts as a reversible or irreversible competitive inhibitor of one or more caspases. Active site mimetic peptide ketones are useful, for example, as selective caspase inhibitors. Such caspase inhibitors include, for example, benzylcarbonyl (z)-VAD-fluoromethylketone (fmk), z-VAD-fmk/chloromethylketone (CMK), z-DEVD-fmk/cmk; and z-D-cmk. Additional caspase inhibitors include the halomethyl ketone-linked peptide YVAD, Ac-WEHD-CHO, Ac-DEVD-CHO, Ac-YVAD-CHO, t-butoxycarbonyl-IETD-CHO, and t-butoxycarbonyl-AEVD-CHO (Ekert et al., supra, 1999). The skilled person understands that these and other caspase inhibitors known in the art can be useful in the methods of the invention. See, for example, Nicholson, *Nature* 407:810-816 (2000); WO 00/55114; and Garcia-Calvo et al., *J. Biol. Chem.* 273:32608-32613 (1998)).

As disclosed herein, EPO or an active fragment or analog thereof can cross the blood-brain barrier following intranasal administration, whereby unwanted systemic effects such as increased hematocrit can be avoided. In particular, intranasally applied radiolabeled EPO migrated into olfactory tissue and was observed in the rostral migratory stream (RMS). Furthermore, autoradiography demonstrated that radiolabeled erythropoietin accumulated in brain tissue when applied intranasally. These results demonstrate that intranasal administration can be used to deliver erythropoietin and active fragments and analogs thereof to the brain, for example, via the rostral migratory stream. These results further indicate that intranasal administration of EPO, or active fragments or analogs thereof, can be useful for treating neurologic conditions such as stroke or neurodegenerative conditions while avoiding side effects associated with chronic systemic erythropoietin administration.

Thus, the present invention provides a method of preventing or reducing the severity of a neurologic condition in a subject by intranasally administering to the subject EPO or an active fragment or analog thereof, thereby preventing or reducing the severity of the neurologic condition. In one embodiment, the EPO or an active fragment or analog thereof is administered at a dose of at most 2000 U/kg.

A variety of forms of erythropoietin, as well as active fragments and analogs thereof, can be administered intranasally in the methods of the invention. In one embodiment, a method of the invention is practiced by intranasal administration of EPO or an active fragment thereof, for example, by intranasal administration of human EPO or an active fragment thereof. In another embodiment, a method of the invention is practiced by intranasal administration of an EPO analog, which can be, without limitation, a peptide, peptidomimetic, small molecule or nucleic acid EPO analog. In further embodiments, a method of the invention is practiced by intranasal administration of an EPO analog that includes the amino acid sequence GGTYSCHFG-PLTWVCKPQGG (SEQ ID NO: 7); GGDYHCRMG-PLTWVCKPLGG (SEQ ID NO: 8); GGVYACRMGPIT-WVCSPLGG (SEQ ID NO: 9); VGNYMCHFGPITWVCRPGGG (SEQ ID NO: 10); GGLYLCRFGPVTWDCGYKGG (SEQ ID NO: 11); or GGCRIGPITWVCGG (SEQ ID NO: 12).

In another embodiment, a method of the invention is practiced by intranasal administration of EPO, or an active fragment or analog thereof, which has at least 10-fold higher affinity for the EPO receptor than native human EPO. In another embodiment, a method of the invention is practiced by intranasal administration of EPO or active fragment or analog thereof which is oligomeric, for example, dimeric. As an example, such a dimeric form of EPO can be a dimer in which each monomer contains the amino acid sequence GGTYS<u>CHFGPLTWVC</u>KPQGG (SEQ ID NO: 7). In further embodiments, the invention is practiced with EPO or an active fragment or analog thereof that has a half-life greater than the half-life of native human EPO, or with EPO or an active fragment or analog thereof that is hyper-glycosylated compared to native human EPO, for example, Darbepoietin. In any embodiment of the invention involving intranasal administration of EPO or an active fragment or analog thereof, soluble EPO receptor can be optionally included, for example, to prolong the half-life of EPO or the active fragment or analog thereof.

It is understood that any of a variety of acute and chronic neurologic conditions can be treated by intranasal administration of EPO, or an active fragment or analog thereof, in a method of the invention. Such neurologic conditions include, for example, stroke and neurodegenerative disorders. The methods of the invention which rely on intranasal administration of EPO or an active fragment or analog thereof can be useful for preventing or reducing the severity of neurologic conditions such as, without limitation, stroke, head or spinal cord trauma, Alzheimer's disease, Parkinson's disease, Huntington's disease, epilepsy, amyotrophic lateral sclerosis, multiple sclerosis, a movement disorder, dementia, HIV-associated dementia, fronto-temporal dementia, HIV-associated neuropathy, chronic pain, neuropathic pain, migraine, glaucoma, drug addiction, drug withdrawal, drug dependency, depression and anxiety. One skilled in the art understands that these and other acute and chronic neurologic conditions can be treated by intranasal administration of EPO or an active fragment or analog thereof according to a method of the invention.

Intranasal administration can be accomplished by any method wherein the EPO or an active fragment or analog thereof is introduced via the nasal cavity, with or without enhancers or mechanical devices such as a Rhinüle (Pietrowsky et al., supra, 1996). One skilled in the art understands that nose drops can be useful for intranasal administration, as can other nasal formulations including polymers and formulations as described in Shimoda et al., *Biol. Pharm. Bull.* 18:734-739 (1995).

The present invention also provides a method of differentiating neuronal precursor cells to produce an enriched neuronal cell population by contacting the neuronal precursor cells with EPO or an active fragment or analog thereof; and contacting the neuronal precursor cells with IGF-I or an active fragment or analog thereof, thereby differentiating the neuronal precursor cells to produce an enriched cell population containing at least 70% neurons. In particular embodiments, a method of the invention produces an enriched cell population containing at least 80% neurons, at least 90% neurons or at least 95% neurons. If desired, the neuronal precursor cells further can be contacted with a differentiating agent, for example, retinoic acid. In particular embodiments, the invention is practiced by contacting the neuronal precursor cells with a concentration of at most 2000 U/ml, 1500 U/ml, 1000 U/ml, 750 U/ml, 500 U/ml, 250 U/ml, 100 U/ml or 50 U/ml EPO or active fragment or analog thereof.

Neuronal precursor cells useful in the methods of the invention can be, for example, human stem cells; embryonic stem cells such as human embryonic stem cells; or hematopoietic neuronal precursor cells such as human hematopoietic stem cells. Neuronal precursor cells useful in the methods of the invention also can be, without limitation, selected CD133-positive (AC133-positive); CD133-positive/CD34-positive; CD133-positive/CD34-negative; CD133-positive/CD34-negative/CD45-negative; CD34-negative/CD38-negative/Lin-negative; or CD34-positive/CD38-negative/Lin-negative/Thy-1-negative human neuronal precursor cells.

A method of the invention for differentiating neuronal precursor cells can further include the step of introducing into the neuronal precursor cells a nucleic acid molecule encoding a MEF2 polypeptide or an active fragment thereof. Such a MEF2 polypeptide can be, for example, human MEF2C, or an active fragment thereof, and further can be, if desired, a constitutively active MEF2 polypeptide such as a MEF2/VP16 fusion protein or a constitutively active MEF2 polypeptide containing one or more serine/threonine to aspartic acid/glutamic acid substitutions in the MEF2 transactivation domain. A method of the invention also can include, if desired, the step of inhibiting caspase activity; treating with a protective factor such as minocycline or another tetracycline derivative; or expressing a Bcl-$X_L$ family member in the neuronal precursor cells, for example, to prolong survival during subsequent transplantation.

As used herein, the term "MEF2 polypeptide" means a polypeptide that has MEF2 DNA binding activity in addition to activity as a transcriptional activator and includes polypeptides having substantially the amino acid sequence of MEF2A, MEF2B, MEF2C or MEF2D. Thus, a MEF2 polypeptide can have, for example, substantially the amino acid sequence of human MEF2A; human MEF2B; human MEF2C; or human MEF2D. A MEF2 polypeptide includes a MADS domain, a MEF2 domain and a transcriptional activation domain. It is understood that, while the MADS domain and MEF2 domains of a MEF2 polypeptide will be similar in structure to the MADS domain and MEF2 domain of a naturally occurring MEF2 polypeptide such as human MEF2C, the transcriptional activation domain of a MEF2 polypeptide may be structurally unrelated and can be, for example, a synthetic transcriptional activation or a heterologous transcriptional activation domain derived, for example, from VP16 or GAL4. One skilled in the art appreciates that a fragment of a MEF2 polypeptide that retains MEF2 DNA binding activity and transcriptional activity also can be useful in the methods of the invention.

The term MEF2 polypeptide encompasses a polypeptide having the sequence of a naturally occurring human MEF2A polypeptide (GenBank accession NM 005587), naturally occurring human MEF2B polypeptide (GenBank accession NM 005919), naturally occurring human MEF2C polypeptide (GenBank accession L08895) or naturally occurring human MEF2D polypeptide (GenBank accession NM 005920) and is intended to include related polypeptides having substantial amino acid sequence similarity to one of these polypeptides. Such related polypeptides typically exhibit greater sequence similarity to hMEF2A, hMEF2B, hMEF2C or hMEF2D than to other MADS box proteins such as serum response factor (SRF) and include species homologs such as primate, mouse, rat and *D. rerio* homologs, alternatively spliced forms, and isotype variants of human MEF2A, MEF2B, MEF2C and MEF2D.

Induction of the MEF2 pathway also can be achieved using a MEF2 activator, which is a small molecule that results in increased expression or activity of a MEF2 polypeptide or which is a mimetic of MEF2 function. A MEF2 activator can result in increased expression or activity of one or more MEF2 polypeptides, for example, may result in increased expression or activity of MEF2C without effecting expression or activity of MEF2A, MEF2B or MEF2D. Such a MEF2 activator can be an organic chemical, drug, nucleic acid molecule, peptide, peptidomimetic, polypeptide or other naturally or non-naturally occurring organic molecule, and can be, for example, a MEF2 mimetic. Exemplary MEF2 activators are transcription factors that upregulate MEF2 expression, molecules that compete for binding to a MEF2 inhibitor such as Cabin1, histone deacetylase inhibitors including, but not limited to, VX-563 (Vertex Pharmaceuticals; Cambridge, Mass.), and kinases that activate MEF2 polypeptides such as p38α. It is understood that a MEF2 activator can be useful in any of the methods of the invention disclosed herein.

A variety of differentiating agents optionally are useful in the methods of the invention including, for example, retinoic acid. Other differentiating agents useful in a method of the invention include, without limitation, neurotrophic factor 3, epidermal growth factor, IGF-I, platelet-derived growth factor and other agents that increase cAMP.

A method of the invention for differentiating neuronal cells optionally includes the step of transplanting into a subject cells treated to induce the EPO and IGF pathways. In a method of the invention, cells can be transplanted, for example, into the brain, eye (retina) or spinal cord after neuronal injury or damage. Thus, cells treated to induce the EPO and IGF pathways can be transplanted into a subject having or at risk of, for example, stroke or a neurodegenerative disease such as Alzheimer's disease; Huntington's disease; amyotrophic lateral sclerosis; Parkinson's disease; epilepsy; brain or spinal cord trauma; multiple sclerosis; optic neuropathy such as glaucoma, macular degeneration, or light-induced retinal degeneration such as photoreceptor degeneration; infection of the central nervous system; multiple system atrophy affecting the brain; or another acute or chronic neurodegenerative condition. Upon transplantation, the cells begin to differentiate or continue differentiating to produce a cell population containing protected neuronal cells.

Cells can be transplanted into a subject, for example, into the eye, brain or spinal cord using well known methods for transplanting or "grafting" neurons as described, for example, in McDonald et al., *Nat. Med.* 5:1410-1412 (1999), and summarized in Dunnett et al., *Brit. Med. Bulletin* 53:757-776 (1997). Methods for preventing or ameliorating rejection, for example, using cyclosporine A treatment, also are known in the art.

Those skilled in the art understand that the steps of inducing the EPO pathway, inducing an IGF pathway, and optionally contacting the neuronal precursor cells with a differentiating agent can be performed in any order or simultaneously. It further is understood that a neuronal precursor population in which the EPO and IGF pathways have been induced can be transplanted into a subject prior to, during or after differentiation of the neuronal precursor cells into neuronal cells. In one embodiment, cells are transplanted prior to or during differentiation. Where cells are transplanted prior to differentiation, the neuronal environment can drive the cells into the desired neuronal cell type due to the presence of the appropriate environmental cues. In view of the above, it is clear that differentiation can occur in vitro or in vivo, or can occur partially in vitro and partially in vivo.

As used herein in reference to a neuronal cell, the term "protected" means a cell that is more resistant to injury, apoptosis or cell death than a cell in which EPO and IGF pathways have not been induced, or in which these pathways have been induced to a lesser extent. Thus, a population containing protected neuronal cells can exhibit reduced apoptosis as compared to a population that does not contain "protected" neuronal cells. Assays for determining the extent of apoptosis are known in the art, as described hereinabove.

It is understood that a method of the invention can be used to produce a population that contains protected neuronal cells and in which a large proportion of the cell population is neuronal. For example, a method of the invention can be used to produce a cell population containing, for example, at least 50% neuronal cells. In other embodiments, the population produced includes at least 55%, 60%, 65%, 70%, 75%, 80%, 85%, 90%, 95% or more neuronal cells. The proportion of neuronal cells can be determined by assaying for one or more characteristic neuronal markers such as the presence of NeuN, neurofilament or MAP2.

The methods of the invention for differentiating neuronal precursor cells can include, if desired, contacting the neuronal precursor cells with a differentiating agent. As used herein, the term "differentiating agent" means a naturally occurring or synthetic cytokine, growth factor or other compound that causes or enhances a neuronal precursor cell to have one or more characteristics of a neuronal cell. A differentiating agent useful in the invention can be, for example, a retinoic acid such as all-trans retinoic acid; neurotrophic factor 3 (NT3); epidermal growth factor (EGF); EPO; IGF-I; platelet derived growth factor (PDGF), or a combination of two or more of these factors. For example, EGF, IGF-I and PDGF can be used together as a differentiating agent. Basic fibroblast growth factor (bFGF) or another factor that enhances proliferation of precursor cells optionally can be used prior to treating with a differentiating agent such as EGF, IGF-I and PDGF. One skilled in the art understands that, if desired, one or more factors such as brain-derived neurotrophic factor (BDNF) also can be added to promote neuronal cell survival. A neuronal precursor cell also can be engineered to express one or more factors that promote differentiation including, for example, MEF2, neuroD, neuroD2, neuroD3, neurogenin1, neurogenin2, neurogenin3, MATH1 or MATH2 (Lee, *Curr. Opin. Neurobiol.* 7:13-20 (1997)). Such a factor can be expressed instead of or in addition to application of an extrinsic differentiating agent.

As used herein, the term "neuronal precursor cell" means any cell that is not a neuron but which is capable of differentiating into a neuron under the appropriate conditions. Neuronal precursor cells can be multipotent or unipotent and can be stem cells, precursor cells, primary cells or established cells. Neuronal precursor cells such as stem cells generally can be distinguished from neurons in that they lack neuronal markers such as the nuclear protein NeuN, neurofilament and microtubule-associated protein 2 (MAP2) as well as the neuronal-like processes characteristic of mature neurons. In one embodiment, the neuronal precursor cells are primary cells, which is a well known term in the art for cells which are derived directly from an organism and which have limited growth capacity in culture.

A neuronal precursor cell useful in the invention can be multipotent or unipotent. As used herein in reference to a neuronal precursor cell, the term "multipotent" is synonymous with "pluripotent" and means a neuronal precursor cell capable of differentiating into two or more distinct lineages, including the neuronal lineage. Multipotent neuronal precursor cells such as stem cells, which are generally nestin-positive cells, are distinguished from unipotent precursor cells, which are generally Hu-positive cells. Expression of nestin and Hu can be determined, for example, by well-established immunocytochemistry methods. A multipotent neuronal precursor cell is capable of differentiating into at least three or more, four or more, or five or more distinct lineages, including the neuronal lineage.

As used herein, the term "stem cell" means a pluripotent cell type which can differentiate under the appropriate conditions to give rise to all cellular lineages. Thus, a stem cell differentiates to neuronal cells, hematopoietic cells, muscle cells, adipose cells, germ cells and all other cellular lineages. A stem cell can be an embryonic stem cell. Where the term "hematopoietic stem cell" is used, it is understood that this term refers to cells that are committed to the hematopoietic lineage but which can differentiate to all cells of the hematopoietic lineage.

As used herein, the term "embryonic stem cell" is synonymous with "ES cell", and means a pluripotent cell type derived from an embryo which can differentiate to give rise to all cellular lineages. Examples of cell markers that indicate a human embryonic stem cell include the Oct-4 transcription factor, alkaline phosphatase, SSEA-4, TRA 1-60, and the GCTM-2 epitope. Examples of cell markers that indicate a differentiated neuronal cell including neurofilament proteins, β-tubulin, Map2a+b, synaptophysin, glutamic acid decarboxylase, TuJ1, SNAP 25, transcription factor Brn-3, and GABA$_A$ α2 receptor subunit as described in Reubinoff et al., *Nat. Biotech.* 18:399-404 (2000); Ghosh and Greenberg, *Neuron* 15:89-103 (1995); Bain et al., *Devel. Biol.* 168:342-357 (1995); and Williams et al., *Neuron* 18:553-562 (1997).

Embryonic stem cells useful in the methods of the invention can be obtained from a variety of sources. Embryonic stem cells can be obtained, for example, from mice, cows, primates and humans by methods well known in the art. As an example, murine embryonic cells can be isolated from a mouse as described in Forrester et al., *Proc. Natl. Acad. Sci. USA* 88:7514-7517 (1991), or Bain et al., *Devel. Biol.* 168: 342-357 (1995). Briefly, two-stage cell embryos are isolated from fertilized female mice about 45 hours after injection with human chorionic gonadotropin. The two blastomeres are fused by electrical impulse and cultured in M16 medium until the four cell stage is reached. The ES cells are grown on gelatin coated tissue culture flasks in DMEM (Dulbeco's modified Eagle's medium) containing high glucose and 1 mM glutamine (BRL) supplemented with 10% fetal bovine serum, 10% newborn calf serum, nucleosides, 1000 units/ml leukemia inhibitory factor, and 0.1 mM 2-mercaptoethanol.

Embryonic stem cells also can be isolated from primates as described in Thomson (U.S. Pat. No. 5,843,780). Briefly, blastocysts are removed from fertilized female monkeys 6-8 days after onset of ovulation, treated with pronase (Sigma) to remove the zona pellucida, rabbit anti-rhesus monkey spleen cell antiserum and guinea pig complement (Gibco BRL), and washed in DMEM. The inner cell mass (ICM) is removed from the lysed blastocyst with a pipette and plated on mouse gamma irradiated embryonic fibroblasts. After 7 to 21 days, the ICM derived masses are removed with a micropipette, treated with 0.05% trypsin-EDTA (Gibco BRL) and 1% chicken serum, and replated on embryonic feeder cells. Colonies demonstrating ES morphology, characterized by compact colonies with a high nucleus to cytoplasm ratio and prominent nucleoli, are subcultured. The ES cells are divided, for example, by trypsinization or exposure to Dulbecco's phosphate buffered saline containing 2 mM EDTA every 1-2 weeks when cultures become dense.

Embryonic stem-like cells also can be isolated from cows as described in Cibelli et al., *Nat. Biotech.* 16:642-646 (1998). Briefly, oocytes are removed from freshly slaughtered cows and placed in maturation medium M199 (Gibco), 10% fetal calf serum (FCS), 5 ug/ml bovine leutinizing hormone (Nobl) and 10 ug/ml pen-strep (Sigma) for 22 hours at 38.5° C. Oocytes are subsequently fertilized in vitro and cultured on mouse embryonic fibroblast feeder layers and CR2 with 6 mg/ml BSA until they reach the blastocyst stage. ES cells are isolated from the blastocyst by mechanical removal of the zona pellucida and trophoblast with a 22 gauge needle and placed under mouse embryonic fibroblast feeder layers for one week. A small colony of the resulting cell mass is removed and cultured on top of a gamma irradiated mouse embryonic fibroblast feeder layer as cultures become dense.

Embryonic stem cells also can be isolated from human blastocysts as described in Reubinoff et al., supra, 2000. Briefly, fertilized oocytes are cultured to the blastocyst stage and the zona pellucida digested by pronase (Sigma). The inner cell mass is removed by immunosurgery with anti-human serum antibody (Sigma) and exposure to Guinea pig complement (BRL), and cultured on a mitomycin C mitotically inactivated mouse embryonic feeder cell layer in DMEM (BRL) supplemented with 20% fetal bovine serum (Hyclone), 0.1 mM 2-mercaptoethanol, 1% non essential amino acids, 2 mM glutamine, 50 units/ml penicillin and 50 ug/ml streptomycin (BRL) and 2,000 units/ml recombinant leukemia inhibitory factor. Cell mass clumps are removed with a micropipette and replated on fresh feeder layer every six to eight days.

Human stem cells can be obtained, for example, from cord blood, which is highly enriched in primitive cells and contains a CD133-positive/CD34-positive population. These cells can be efficiently isolated by methods well known in the art, for example, the Miltinyl MACS system. If desired, the CD133-positive/CD34-positive population can be expanded by culturing in vitro with Flt3L+TPO to produce as much as an 160-fold expansion in long-term culture potential and a $2 \times 10^6$ fold expansion in the number of neuronal precursor cells.

Human neuronal precursor cells useful in the invention include human embryonic stem cells, human hematopoietic stem cells and other neuronal precursor cells isolated from adult human blood or from cord blood of newborn infants. A neuronal precursor cell population can be enriched, for example, in CD133 (AC133)-positive/CD34-positive or CD133-positive/CD34-negative neuronal precursor cells. Such enriched neuronal precursor cells can be isolated, for example, with magnetic-activated cell sorting, fluorescence-activated cell sorting (FACS), or related methods well known in the art as described further below. It further is understood that in vitro expansion of neuronal precursor cells such as human stem cells can be performed, if desired, in the presence of one or more of the following factors: SCF, IL-3, IL-6, flt3L, LIF, IL-II, TGF-β, TPO, and bFGF, which are commercially available, for example, from Biosource (Camarillo, Calif.), R & D Systems (Minneapolis, Minn.) and Chemicon (Temecula, Calif.). Various protocols for expansion and useful concentrations of particular factors are well known in the art.

Human neuronal precursor cells can be obtained, for example, from peripheral blood. Donors can be treated with recombinant human G-CSF (rhG-CSF), such as Neupogen (Amgen; Thousand Oaks, Calif.), or recombinant human GM-CSF (rhGM-CSF), such as Leukine (Immunex; Seattle, Wash.), or both. The human neuronal precursor cells can be primitive cells characterized as CD34+, Thy-/dim, CD38-, which can be obtained, if desired, from G-CSF or GM-CSF treated to donors to increase long-term-culture potential. Apheresis can be used to collect white blood cells, for example, four to five days following treatment with G-CSF, GM-CSF or a combination of G-CSF and GM-CSF, generally yielding $4 \times 10^6$ CD34-positive cells per kilogram of body weight.

A Ceprate SC immunoaffinity column commercially available from Cellpro (Bothell, Wash.) can be used to isolate a CD133-positive neuronal precursor cell population. The desired cell population binds the column matrix via a biotin conjugated antibody linked to the column matrix and is released by mechanical shaking. Ceprate SC immunoaffinity can be used to yield about 50% CD34-positive cells with about 16-99% purity. CD133-positive human neuronal precursor cells also can be isolated, for example, using an Isolex 300 magnetic cell separator (Baxter Healthcare Corporation; Deerfield, Ill.), which relies on mouse monoclonal IgG1 antibodies and magnetic beads coated with anti-mouse IgG1 antibody. Release of the precursor cells by peptidase treatment yields about 50% CD34-positive cells with 33-100% purity.

Additional art-accepted procedures for isolation of human stem and other neuronal precursor cells include the magnetic activated cell sorting system (MACS) commercially available from Miltenyi Biotech (Auburn, Calif.) and fluorescence-activated cell sorting (FACS). In the MACS sorting system, small magnetic beads coated with secondary antibody are bound to the primary antibody-treated cells and retained on a ferromagnetic matrix column by a strong magnet. Cells are released by removal of the magnet to give greater than 50% recovery and greater than 90% purity of the desired cells. Fluorescence-activated cell sorting (FACS) is a well known method whereby cells are selected by attachment of fluorescent-conjugated antibodies to give greater than 90% purity of the recovered stem or other neuronal precursor cells. If desired, isolated stem or other neuronal precursor cells can be assayed for the ability to repopulate bone marrow of a sublethally irradiated nonobese diabetic/severe combined immunodeficient (NOD-SCID) mouse using methods well known in the art, as described, for example, in Miyoshi et al., *Science* 283: 682-686 (1999).

Human CD34-negative bone marrow cells such as CD133-positive/CD34-negative cells or CD133-positive/CD34-negative/Lin-negative cells can be useful in the methods of the invention. Such cells can be, for example, CD34-negative/Lin-negative cells, which can have characteristics of stromal cells and are capable of repopulating the bone marrow of NOD/SCID mice following sublethal irradiation. Methods of preparing neuronal precursor cell populations enriched for particular markers are well known in the art. As an example, CD133-positive/CD34-positive hematopoietic stem and other neuronal precursor cells can be prepared as set forth in Yin et al., *Blood* 90:5002-5012 (1997); CD133-positive/CD34-negative/CD45-negative neuronal precursor cells cells can be prepared as described, for example, in Uchida et al., *Proc. Natl. Acad. Sci., USA* 97:14720-14725 (2000); and CD34-negative/CD38-negative/Lin-negative human hematopoietic stem cells and CD34-positive/CD38-negative/Lin-negative/Thy-1-negative hematopoietic stem cells can be prepared, for example, as described in Bhatia et al., *Nature Medicine* 4:1038-1045 (1998).

In the methods of the invention, neuronal precursor cells such as embryonic stem cells can be contacted with a differentiating agent to induce differentiation of the cells along the neuronal pathway. Methods for differentiating embryonic stem cells by growth of the cells to high density are described in Reubinoff et al., supra, 2000. Methods differentiating expanded CNS cells by initial growth in the presence of a mitogen such as basic fibroblast growth factor (bFGF) followed by removal of bFGF are described in Johe et al., *Genes Develop.* 10:3129-3140 (1996). Induction of neurogenesis by addition of growth factors can be achieved with platelet derived growth factor (PDGF) such as PDGF-AA, PDGF-AB or PDGF-BB administered in the absence of bFGF as described in Johe et al., supra, 1996. Induction of neuronal differentiation also can be achieved in vitro by removal of fibroblast growth factor-2 and subsequent addition of insulin like growth factor-1, heparin or neurotrophin-3 as described in Brooker et al., *J. Nerosci. Res.* 59:332-341 (2000) and Ghosh and Greenberg, *Neuron* 15:89-103 (1995); addition of platelet-derived growth factor as described in Williams et al., *Neuron* 18:553-562 (1997); addition of insulin-like growth factor-1 alone or in combination with brain derived neurotrophic factor as described in Arsenijevic and Weiss, *J Neurosci.* 18:2118-2128 (1998); and exposure to retinoic acid as described in Bain et al., *Devel. Biol.* 168:342-357 (1995).

The following examples are intended to illustrate but not limit the present invention.

EXAMPLE I

Amelioration Of NMDA-Induced Neurotoxicity by EPO in Combination with IGF-I does not Require Preincubation Before Neurotoxic Insult This example demonstrates that simultaneous application of EPO and IGF-I at the time of neurotoxic insult effectively reduces apoptosis of mature neurons in rat primary cerebrocortical cultures exposed to NMDA.

The neuroprotective effects of concurrent EPO and IGF-I administration were compared to individual treatment with EPO or IGF-I in rat primary cerebrocortical cultures. Incubation of the cultures with 200 μM NMDA for 20 minutes induced death only in neurons in the mixed neuronal/glial cultures as reported previously (Bonfoco et al., supra, 1995).

Neuronal apoptosis was quantified by double labeling for TUNEL reactivity, which in conjunction with condensed morphology is indicative of apoptosis, and the neuron-specific protein microtubule associated protein-2 (MAP2) 16 hours after NMDA insult. As shown in FIG. 3, a brief 20 minute exposure to NMDA produced an apoptotic appearance and TUNEL reactivity in 76+7% of MAP2-labeled neurons. Preincubation for three hours with either EPO (10 U/ml) or IGF-I (100 ng/ml) alone significantly attenuated neuronal apoptosis ($p<0.05$). The EPO and IGF-I doses assayed represent maximally effective concentrations of these factors as previously determined from dose-response curves (Heck et al., *Biol. Chem.* 274:9828-9835 (1999); and Digicaylioglu and Lipton, *Nature* 412:641-647 (2001)). Control incubations with IGF-I or EPO in the absence of NMDA exposure did not affect neuronal viability.

As expected, treatment of neurons with EPO or IGF-I individually at the time of NMDA insult did not significantly reduce cell death (see FIG. 3). In contrast, application of EPO together with IGF-I at the time of NMDA exposure was about as effective in preventing apoptosis as a three hour preincubation with both factors either alone or together. In particular, modest, 5-10%, reductions in neuronal apoptosis were seen with either EPO or IGF-I alone, while about 50% neuronal apoptosis was suppressed with combined EPO and IGF-I treatment at the time of NMDA insult. These results demonstrate that signal transduction pathways activated by IGF-I and EPO converge to promote more rapid neuroprotection than either factor mediates in the absence of the other. These results further indicate that IGF-I and EPO synergize to mediate acute neuroprotection.

For these experiments, mixed neuronal/glial cerebrocortical cultures were prepared as described previously (Bonfoco et al., supra, 1995); Lei et al., *Neuron* 8:1087-1099 (1992); and Lipton et al., *Nature* 364:626-632 (1993)). In brief, cortical tissue from embryonic day 16 Sprague-Dawley rats was dissociated in 0.5% trypsin and plated on poly-L-lysine coated glass coverslips at a density of $10^5$ cells per 35 mm culture dish in serum-containing medium. Prior to experimental use, cerebrocortical neurons were kept at 37° C. and 5% $CO_2$ for at least 17 days to permit full expression of NMDA receptors (Lei et al., supra, 1992; and Lipton et al., supra, 1993).

EPO and IGF-I incubations were performed essentially as follows. Human recombinant EPO purchased from Amgen (Epoietin alfa, 2000 IU/ml) was diluted in cell culture medium to a final concentration of 5-10 U/ml. Insulin-like growth factor-I (IGF-I) (Calbiochem; La Jolla, Calif.) was diluted in cell culture medium to a final concentration of 50-100 ng/ml.

NMDA incubations were performed as follows. Cerebrocortical cultures were exposed to 200 µM NMDA in nominally $Mg^{2+}$-free Earle's Balanced Salt Solution (EBSS), containing 1.8 mM $CaCl_2$ and 5 µM glycine for 20 minutes. After NMDA exposure, cultures were washed with EBSS and then placed in conditioned tissue culture medium filtered with a 0.2 µM Acrodisk filter (Perkin-Elmer; Wellesley, Mass.) to remove activated microglia. Where indicated, EPO, IGF-I or both EPO and IGF-I were added to the conditioned media.

Detection of apoptotic neurons was performed essentially as follows. After experimental incubation, cerebrocortical cultures were fixed in PBS (150 mM NaCl, 1.7 mM monobasic sodium phosphate, 9.1 mM dibasic sodium phosphate) with 4% paraformaldehyde, and permeabilized in PBS containing 1% Tween-20. Apoptotic cells were identified by condensed morphology in conjunction with TUNEL using the Apoptosis Detection System (Promega; Madison, Wis.). Cultures were labeled according to the manufacturer's protocol using FITC-labeled 12-dUTP to visualize DNA strand breaks.

In order to specifically evaluate neuronal apoptosis in cerebrocortical cultures, neurons were double-labeled for TUNEL reactivity and MAP2 16 hours after NMDA insult. MAP-2 staining was performed essentially as described in Budd et al., *Proc. Natl. Acad. Sci., USA* 97:6161-6166 (2000). Apoptotic neurons were identified using a Zeiss inverted Axiovert microscope equipped with camera and software for deconvolution (Intelligent Imaging Innovations; Denver, Colo.).

EXAMPLE II

PI3-Kinase is Required for Neuroprotection by EPO And IGF-I

This example demonstrates that the PI3 kinase can play a role in mediating the neuroprotective effects of EPO and IGF-I.

PI3-kinase is involved in IGF-I and EPO signaling (Mayeux et al., supra, 1993; Kermer et al., supra, 2000; and Damen et al., *J. Biol. Chem.* 270:23402-23408 (1995)). In order to elucidate the role of PI3-kinase in the neuroprotective effects of EPO and IGF-I, rat cerebrocortical neurons were preincubated for three hours with EPO, IGF-I, or EPO in combination with IGF-I (EPO/IGF-I) in the presence or absence of 10 µM LY294002, a specific PI3-kinase inhibitor. As shown in FIG. 4, neuronal apoptosis resulting from NMDA exposure (200 µM NMDA and 5 µM glycine for 20 minutes) decreased in cells preincubated with EPO, IGF-I or EPO/IGF-I. As further shown in FIG. 4, LY294002 abolished the neuroprotective effect of EPO and IGF-I either alone or in combination ($p<0.05$) but did not itself cause neuronal apoptosis in cerebrocortical cultures or increase the amount of apoptosis induced by NMDA. These results indicate that PI3-kinase activity is required for EPO- and IGF-I-mediated neuroprotection.

For PI3-kinase inhibition, cultures were prepared and incubated with NMDA alone, or with EPO or IGF-I individually, or EPO in combination with IGF-I, as described above. PI3-kinase activity was inhibited pharmacologically with 10 µM LY294002 (Calbiochem; San Diego, Calif.) dissolved in dimethylsulfoxide (DMSO, Sigma) and added to cultures 30 minutes prior to the addition of the indicated growth factor or factors. Neuronal apoptosis was assessed 16 hours after NMDA application by determining the percentage of MAP2-positive cells that were also TUNEL positive, as described above.

PI3-kinase is activated by phosphorylation of a p85 regulatory subunit, which leads to release of the catalytic subunit (Pleiman et al., *Science* 263:1609-1612 (1994)). To determine if EPO or IGF-I induces phosphorylation of the p85 subunit of PI3-kinase, rat cerebrocortical cultures were treated with EPO or IGF-I for 10, 20 or 30 minutes, and protein lysates from these cultures analyzed by immunoblotting for the presence of phospho-p85. As shown in FIG. 5B (upper and lower panels), both factors induced p85 phosphorylation in a time-dependent manner. However, IGF-I incubation resulted in maximal phosphorylation of p85 subunit of PI3-kinase after 10 minutes, whereas EPO-induced phosphorylation was observed after 20 to 30 minutes. Equal protein loading was confirmed by analyzing the amounts of total p85 with a second antibody. These results indicate that EPO and IGF-I induce phosphorylation of the p85 regulatory subunit of PI3 kinase, with IGF-I activation occurring more rapidly.

In the murine interleukin-3-dependent cell line DA-3, liganded EPO receptor (EPO-R) has been shown to directly associate with PI3-kinase (Damen et al., supra, 1995; He et al., *Blood* 82:1609-1612 (1993)). To determine if binding of EPO to the EPO receptor promotes a PI3-kinase/EPO-R interaction in primary neurons, EPO-R complex was immunoprecipitated from cerebrocortical culture lysates that were either untreated or treated with EPO for 5 or 10 minutes. Blots of the immunoprecipitated proteins were probed with antibody recognizing the p85 subunit of PI3-kinase (FIG. 5A, top), and equal protein loading confirmed by probing with anti-EPO-R antibody (FIG. 5A, bottom). As shown in the FIG. 5B, brief incubation with EPO (5-10 minutes) promoted an association between EPO-R and the p85 subunit of PI3-kinase. However, in the absence of EPO, only very low levels of the p85/EPO-R complex were detected. These results demonstrate that ligand binding to neuronal EPO-R promotes the association of PI3-kinase with this receptor and indicate that this association can result in phosphorylation and activation of PI3-kinase (Scheid and Woodgett, *Nat. Rev. Mol. Cell. Biol.* 2:760-768 (2001)).

Preparation of total cell extracts for immunoblotting or immunoprecipitation was performed essentially as follows. Cultures were washed briefly in cold PBS. After addition of ice cold lysis buffer (50 mM Tris-Cl, 150 mM NaCl, 1.1 mM PMSF, 10 µg/ml Aprotinin, 1% Triton X-100, pH 8.0, 2 mM Ortho-Vanadate, 0.1% deoxycholate), cells were scraped off the culture dishes. Lysates were transferred to a microcentrifuge tube, vortexed for 15 seconds at 4° C., and cleared by centrifugation for 20 minutes at 14,000×g at 40° C. Protein concentrations were determined using a BCA Protein assay kit (Pierce; Rockford, Ill.).

Immunoblotting was performed as follows. Total protein (30 mg) was resolved on a 10% NuPage Bis-Tris SDS gel (Invitrogen; Carlsbad, Calif.) with MOPS electrode buffer under reducing conditions and electroblotted onto a nitrocellulose membrane (Amersham; Piscataway, N.J.) for three hours. Nonspecific binding was blocked by incubation with 5% non-fat dry milk in Tris-buffered saline (pH 7.5) containing 0.1% Tween-20 for one hour at room temperature. After blocking, the blots were incubated overnight at 4° C. with the appropriate primary antibody diluted in blocking buffer. Anti-EPO-R was used at 1:200 dilution (R&D; Minneapolis, Minn.), and anti-p85 was used at 1:400 dilution (Upstate; Waltham, Mass.). After the primary antibody incubations, membranes were washed in Tris buffered saline with 0.1% Tween-20 for 10 minutes with three changes and incubated with the secondary antibody conjugated with horseradish peroxidase (Vector Labs, 1:400) for one hour at room temperature and washed again in Tris buffered saline with 0.1% Tween-20. Blots were developed with an enhanced chemiluminescence kit obtained from Amersham and exposed to X-ray film.

Immunoprecipitations were performed using precleared whole-cell lysates, which were incubated with 2 μg of anti-EPO-R antibody (Cell Signaling Technologies; Beverly, Mass.) for one hour at room temperature, followed by addition of protein A/G-Sepharose beads (Santa Cruz Biotechnology; Santa Cruz, Calif.). Immunoprecipitates were run on SDS gels as described above and probed with the appropriate antibody. For loading controls, blots were stripped and reprobed with the indicated primary antibody and appropriate secondary antibody.

EXAMPLE III

EPO And IGF-I Cooperate in Activating Akt

This example demonstrates that the Akt kinase can be cooperatively activated by EPO and IGF-I in neuronal cells.

Akt-kinase is activated downstream of PI3-kinase-mediated production of 3' phospholipids. In response to production of phosphotidylinositol-3,4,5-trisphosphate, Akt is phosphorylated at two critical sites: serine-473 and threonine-308 (Russell et al., *Nuerobiol.* 36:455-467 (1998); Scheid and Woodgett, supra, 2001).

To assess possible activation of the Akt kinase, cerebrocortical-cultures were exposed to EPO or IGF-I for three hours and immunoblotted as described above using anti-phospho Akt (anti-pAkt) and anti-Akt antibodies from Cell Signaling Technologies at 1:2000 dilution. A three hour incubation with EPO or IGF-I resulted in moderate Akt activation, as evidenced by increased phospho-serine-473 Akt detected by western blotting (FIG. 6A). Co-incubation with EPO and IGF-I resulted in a much larger increase in phospho-serine-473 Akt. Furthermore, a 20-minute exposure to NMDA reduced constitutive levels of Akt phosphorylation but did not inhibit the Akt phosphorylation mediated by EPO in combination with IGF-I. Total Akt, measured by reprobing with an anti-Akt antibody, was unchanged either by the addition of EPO/IGF-I or NMDA. Taken together, these results indicate that phosphorylation of Akt on serine-473 is synergistically induced by the combination of EPO and IGF-I.

As described above, rat cerebrocortical cultures contain a mixture of neuronal and glial cells. Double immunofluorescence labeling with anti-phosphorylated Akt (serine-473) and neuron-specific MAP2 antibodies demonstrated that Akt activation in response to EPO/IGF-I treatment occurred predominantly in neurons. In cerebrocortical cultures treated with EPO in combination with IGF-I and exposed to NMDA, there was an increase in phospho-Akt labeling similar to that observed in cultures treated with EPO/IGF-I alone. These results demonstrate that EPO and IGF-I synergize to produce activated Akt in neuronal cells.

Double immunofluorescence staining for phosphorylated Akt and the neuron-specific marker MAP2 was performed as follows. Cerebrocortical cells were fixed in ice-cold PBS containing 4% paraformaldehyde for 10 minutes at >4° C., rinsed 3 times in PBS, and permeabilized in PBS containing 1% Tween-20 for 10 minutes at room temperature. Phosphorylated Akt was detected by incubation with specific polyclonal antibodies (Cell Signaling Technologies) diluted 1:1000, followed by detection with FITC-conjugated secondary antibody at 1:125 dilution (Sigma; St. Louis, Mo.). Neurons were identified by using a primary antibody against MAP2 (Sigma) and a secondary antibody conjugated to Texas-Red (Vector Labs; Irvine, Calif.).

EXAMPLE IV

The Akt Kinase can Play a Role in Mediating the Neuroprotective Effects of EPO and IGF-I This example demonstrates that inhibition of Akt activity with a dominant negative form of Akt reduces the neuroprotective effects of EPO and IGF-I.

Figure 7:
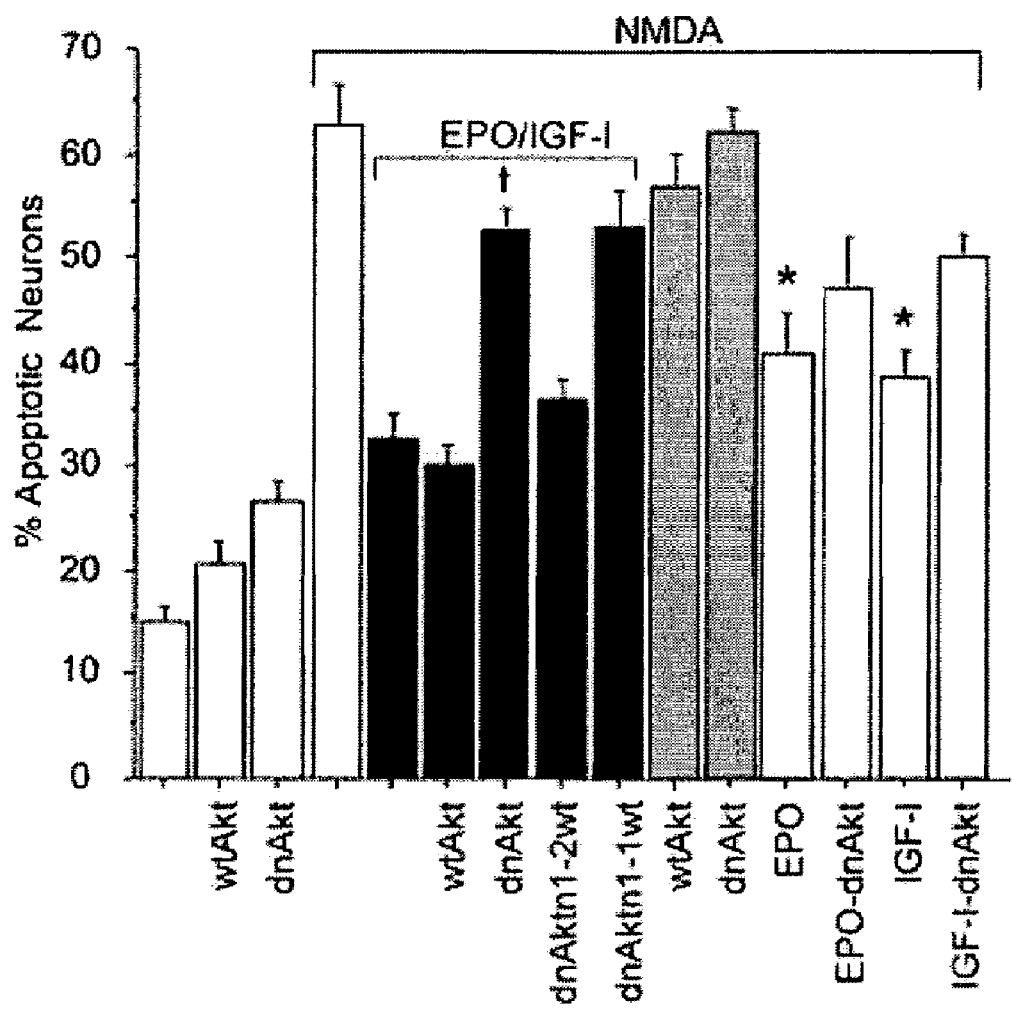
FIG. 7 shows that Akt contributes to neuroprotection mediated by combined treatment with EPO and IGF-I. Cerebrocortical cultures were exposed to an adenoviral vector encoding a wild-type (wt) or dominant-negative (dn) form of Akt for four hours. Other cultures were coinfected with wt and dn Akt in a molar ratio of 1:1 or 2:1 (wt-Akt:dn-Akt). Thirty-six hours later, cells were incubated with 10 U/ml EPO, 100 ng/ml IGF-I, or both EPO/IGF-I, with or without simultaneous application of 200 µM NMDA. After an additional 16 hours, cells staining positive for TUNEL (to identify apoptotic cells) and MAP2 (to specifically identify neurons) were scored as apoptotic neurons. *, $p<0.05$ by ANOVA versus EPO/IGF-I plus NMDA; t, $p<0.01$ versus EPO/IGF-I plus NMDA with or without wt-Akt.

The role of Akt in the EPO/IGF-I signaling pathway was analyzed using a dominant negative Akt construct (dn-Akt) in which a critical phosphorylation site has been mutated (Fujio and Walsh, *J. Biol. Chem.* 274:16349-16354 (1999)). Cerebrocortical cultures were infected with an adenoviral vector encoding dn-Akt (Fujio and Walsh, supra, 1999) and assayed for the effects of NMDA alone or in cultures also treated with EPO in combination with IGF-I. Parallel cerebrocortical cultures were infected with an adenoviral vector encoding wild-type Akt (wt-Akt) as a control. As shown in FIG. 7, infection for 36 hours with either dominant negative or wild type Akt had no significant effect on neuronal viability. Overexpression of wt-Akt also had no significant effect on NMDA-induced apoptosis or EPO/IGF-I-mediated neuroprotection of cultures exposed to NMDA. Furthermore, overexpression of dn-Akt did not affect neuronal apoptosis-consequent to NMDA exposure. However, cerebrocortical cultures expressing dn-Akt and incubated with EPO/IGF-I displayed significantly higher levels of NMDA-induced neuronal apoptosis in comparison with uninfected cultures or cultures infected with wt-Akt ($p<0.01$). Overexpression of wt-Akt abrogated the pro-apoptotic effects of dn-Akt expression when co-infected in a molar excess ratio of 2:1 (wt-Akt:dn-Akt), indicating that the increased neuronal apoptosis seen in dn-Akt infected cells resulted from specific expression of dn-Akt rather than a non-specific effect of protein overexpression. In sum, these results indicate that Akt phosphorylation and activation play a role in the neuroprotection mediated by the combination of EPO and IGF-I.

Cultures were prepared and treated with NMDA, EPO, IGF-I, or EPO in combination with IGF-I, where indicated, as described above, and the percentage of apoptotic neurons was determined by TUNEL in combination with morphology and MAP2-reactivity as described above. An adenoviral vector expressing hemagglutinin (HA)-tagged, nonphosphorylatable, dominant-negative mutant of Akt (Fujio and Walsh, supra, 1999) was obtained from Dr. K. Walsh. Infections were performed with a multiplicity of infection (MOI) of 10 and using HA-tagged wild type Akt as a control. After a four hour exposure to the adenovirus, primary neurons were incubated in filtered preconditioned medium for 24-36 hours before being used in experiments. Expression of the viral Akt constructs was confirmed by immunofluorescence labeling with monoclonal anti-HA antibody (1:100, Roche; Basel, Switzerland).

EXAMPLE V

EPO/IGF-I Treatment does not Prevent NMDA-Induced Caspase-3 Activation

This example demonstrates that treatment with EPO in combination with IGF-I prevents NMDA-induced neurotoxicity in the presence of the active form of caspase-3, indicating that EPO/IGF-I-mediated neuroprotection occurs downstream of caspase-3.

In cerebrocortical cultures briefly exposed to an excitotoxic dose of NMDA, mitochondrial cytochrome c is released, followed by activation of the intrinsic caspase pathway (Budd et al., *Proc. Natl. Acad. Sci. USA* 97:6161-6166 (2000); Yuan and Yankner, *Nature* 407:802-809 (2000)). Constitutively active Akt prevents activation of caspase-9 and caspase-3 downstream of cytochrome c release (Zhou et al., supra, 2000), indicating that Akt is an important factor that regulates the intrinsic caspase cascade (see, also, Kermer et al., supra, 2000).

The effect of EPO/IGF-I incubation on caspase activation was analyzed in cerebrocortical cells following NMDA insult. Cerebrocortical cultures were exposed to NMDA with or without co-administration of EPO in combination with IGF-I, and the cultures fixed 6, 12, 16, or 48 hours following NMDA exposure. Caspase-3 activation was assessed by immunodetection using an antibody recognizing only the active form of caspase-3. The results showed that many MAP2 labeled neurons expressed the active form of caspase-3 in their condensed nuclei as early as 16 hours after NMDA exposure, and EPO/IGF-I treatment did not prevent initial activation of caspase-3 by NMDA. However, EPO-IGF-I treated neurons showed reduced immunoreactivity for active caspase-3 and did not lose MAP2 labeling in their processes. Prolonged survival of the neurons following treatment indicates that neuroprotection mediated by the combination of EPO and IGF-I occurs, at least in part, downstream of initial caspase-3 activation, which is typically associated with neuronal apoptosis within 16 hours of NMDA insult (Tenneti et al., supra, 1998, Budd et al., supra, 2000).

For these experiments, neuron-rich cerebrocortical cultures were continuously exposed to EPO and IGF-I (10 U/ml and 100 ng/ml, respectively) from the time of NMDA exposure (200 μM for 20 minutes) until they were fixed. Immunofluorescence assays were performed as described above, with neurons expressing active caspase-3 identified by double labeling with monoclonal anti-MAP2 and a polyclonal antibody specific for the cleaved form of caspase-3 (Cell Signaling Technologies) using a 1:100 dilution.

In order to determine if prolonged neuroprotective effects are mediated by combined EPO and IGF-I treatment, the number of surviving cerebrocortical neurons was determined at various intervals after exposure to NMDA. The total number of viable MAP2 positive cells was assayed to avoid the effects of secondary necrosis seen at longer survival times (Bonfoco et al., supra, 1995). As shown in FIG. 8A, NMDA exposure alone resulted in a dramatic decrease in the number of surviving neurons. Combined application of EPO and IGF-I prevented neuronal cell death at 6, 12, 16 and 48 hours after NMDA exposure. These results demonstrate that EPO/IGF-I supports long-term neuronal survival after NMDA exposure to a greater extent than observed with either factor alone.

Primary cultures were prepared and incubated with NMDA with or without EPO/IGF-I as described above. Neuronal survival was assayed as the total number of MAP2 positive cells to avoid the confounding effects of secondary necrosis, which can occur at later time points and obfuscate the number of apoptotic cells (Bonfoco et al., supra, 1995).

In mixed cerebrocortical cultures, EPO is known to induce expression of XIAP and c-IAP, two related factors capable of inhibiting caspase-3 proteolytic activity (Digicaylioglu and Lipton, supra, 2001; and Holcik and Korneluk, *Nat. Rev. Mol. Cell. Biol.* 2:550-556 (2001)). Here, cerebrocortical cultures were analyzed for the effect of combined EPO and IGF-I treatment on association of XIAP and active caspase-3. Cultures were incubated with EPO, IGF-I and NMDA and, after immunoprecipitation of the active form of caspase-3, immunoprecipitates were probed for the presence of XIAP using western blotting. As shown in FIG. 8B, active caspase-3 was associated with XIAP in cultured neurons, and treatment with EPO and IGF-I increased the relative amount of XIAP associated with active caspase-3. In particular, in cultures treated with EPO and IGF-I for 16 hours, densitometric analysis revealed a 2.5 to 3-fold increase in the amount of XIAP bound to active caspase-3 (see FIG. 8C), although NMDA exposure alone also produced a modest increase in the amount of XIAP associated with active caspase-3. The presence of an active caspase-3/XIAP complex in neurons indicates that, following activation of caspase-3 by proteolytic cleavage, the active form can be negatively regulated by association with XIAP.

To study the effect of combined EPO/IGF-I treatment on proteolytic activity of caspase-3, protein lysates were prepared from cerebrocortical cultures 16 hours after NMDA exposure, and caspase-3 activity was assayed using the fluorescent caspase-3 substrate, DEVD-7-amino-4-trifluoromethyl-coumarin (DEVD-AFC). FIG. 8D shows that, despite the presence of basal levels of XIAP in the lysates, NMDA exposure resulted in increased DEVD cleavage. Simultaneous application or 3 hour preincubation with EPO in combination with IGF-I diminished the NMDA-induced increase in caspase-3-like activity by increased XIAP expression. Furthermore, the reduction in caspase-3 activity was partially inhibited by infection with dn-Akt in cultures preincubated with EPO and IGF-I (FIG. 8D). These results indicate that Akt can play a role in regulating the proteolytic activity of neuronal caspase-3.

To perform these experiments, cerebrocortical cultures were exposed to NMDA, or EPO and IGF-I, or concurrently exposed to NMDA and EPO/IGF-I as described above. Immunoprecipitation of culture lysates was performed using precleared whole-cell lysates, incubated with a 1:100 dilution of antibody specifically recognizing the cleaved form of caspase-3 (Cell Signaling Technologies) for one hour at room temperature, followed by addition of protein A/G-Sepharose beads and immunoprecipitation as described above. The immunoprecipitates were separated by electrophoresis and transferred to a nitrocellulose membrane, which was blotted with a 1:200 dilution of anti-XIAP antibody (Trevigen; Gaithersburg, Md.).

Caspase-3 (DEVD) cleavage assays were performed as described previously. Briefly, cerebrocortical cultures were lysed in cold buffer containing 10% sucrose, 0.1% CHAPS, 100 mM HEPES (pH 7.5), and 10 mM dithiothreitol (DTT). Cytoplasmic protein extracts (200 μg) were incubated for 30 minutes at 37° C. with 80 μM caspase-3 peptide substrate DEVD-AFC (Enzyme Systems Products; Livermore, Calif.). Free fluorescent AFC released by caspase-3 activity was measured on a FluoroMax2 fluorometer at 400 nm excitation and 505 nm emission.

To determine if the prolonged survival afforded by combined EPO and IGF-I treatment was mediated by non-neuronal cells in the mixed cerebrocortical cultures, primary cultures were grown under conditions that inhibit growth of non-neuronal cells. As shown in FIG. 8E, the relatively pure neuronal cultures also were protected from NMDA-induced apoptosis by the combination of EPO and IGF-I treatment. These results indicate that non-neuronal cells are not required for the neuroprotective benefits of combined treatment with EPO and IGF-I. Taken together, these results demonstrate that combined EPO and IGF-I treatment promotes neuronal survival downstream of caspase-3 activation by a signal transduction pathway intrinsic to neurons.

Relatively pure neuronal cultures were prepared from rat cortices in a similar manner as preparation of mixed neuronal/glial cultures but with the following modifications. Culture medium was replaced on the second day after plating with Neurobasal medium containing B27 supplements (Life Technologies; Carlsbad, Calif.). The cultures were then maintained for an additional 15 to 16 days; the cultures were composed of greater than 95% neurons (Johnson et al., *J. Neurosci.* 19:2996-3006 (1999)).

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

APPENDIX A

Table of Concordance

| Previous Claim | Current Claim |
| --- | --- |
| 1 | 116, 129, 143, 160, 173, 187, 204, 218, 233 |
| 3 | 117, 130, 161, 174, 205, 219 |
| 6 | 144, 188, 234 |
| 7 | 145, 189, 235 |
| 8 | 146, 190, 236 |
| 9 | 118, 131, 147, 162, 175, 191, 206, 220, 237 |
| 10 | 119, 132, 148, 163, 176, 192, 207, 221, 238 |
| 11 | 120, 133, 149, 164, 177, 193, 208, 222, 239 |
| 12 | 134, 150, 178, 194, 223, 240 |
| 13 | 121, 135, 151, 165, 179, 195, 209, 224, 241 |
| 14 | 122, 136, 152, 166, 180, 196, 210, 225, 242 |
| 15 | 153, 197, 243 |
| 16 | 123, 137, 154, 167, 181, 198, 211, 226, 244 |
| 18 | 124, 138, 155, 168, 182, 199 |
| 19 | 125, 139, 156, 169, 183, 200 |
| 22 | 212, 227, 245 |
| 23 | 213, 228, 246 |
| 24 | 214, 229, 247 |
| 25 | 126, 140, 157, 170, 184, 201, 215, 230, 248 |
| 26 | 127, 141, 158, 171, 185, 202, 216, 231, 249 |
| 27 | 128, 142, 159, 172, 186, 203, 217, 232, 250 |

We claim:

1. A method of providing neuroprotection from N-methyl-D-aspartic acid (NMDA) receptor-mediated excitatory insult, comprising:
   (a) contacting neuronal cells in vitro with erythropoietin (EPO) close to or subsequent to the time of excitatory insult; and
   (b) contacting said neuronal cells with an insulin-like growth factor (IGF) close to or subsequent to the time of excitatory insult,
   thereby producing a synergistic neuroprotective effect from NMDA receptor-mediated excitatory insult in said neuronal cells.

2. The method of claim 1, wherein said EPO is human EPO.

3. The method of claim 1, wherein said EPO has at least 10-fold higher affinity for the EPO receptor than native human EPO.

4. The method of claim 1, wherein said EPO is oligomeric.

5. The method of claim 4, wherein said oligomeric EPO is dimeric.

6. The method of claim 1, wherein said EPO has a half-life greater than native human EPO.

7. The method of claim 1, wherein said EPO is hyperglycosylated compared to native human EPO.

8. The method of claim 1, further comprising contacting said neuronal cells with soluble EPO receptor.

9. The method of claim 1, wherein said IGF is IGF-I.

10. The method of claim 9, wherein said IGF-I is human IGF-I.

11. The method of claim 1, wherein said IGF has at least 10-fold higher affinity for the IGF-I receptor than native human IGF-I.

12. The method of claim 1, wherein said IGF active fragment has an altered affinity for an IGF-binding protein (IBP).

13. The method of claim 1, wherein said IGF has a half-life greater than native human IGF.

14. A method of providing neuroprotection from NMDA receptor-mediated excitatory insult, comprising:
(a) contacting neuronal cells in vitro with an active fragment of erythropoietin (EPO) close to or subsequent to the time of excitatory insult; and
(b) contacting said neuronal cells with an insulin-like growth factor (IGF) close to or subsequent to the time of excitatory insult,
thereby producing a synergistic neuroprotective effect from NMDA receptor-mediated excitatory insult in said neuronal cells.

15. The method of claim 14, wherein said EPO is human EPO.

16. The method of claim 14, wherein said EPO active fragment has at least 10-fold higher affinity for the EPO receptor than native human EPO.

17. The method of claim 14, wherein said EPO active fragment is oligomeric.

18. The method of claim 17, wherein said oligomeric EPO active fragment is dimeric.

19. The method of claim 14, wherein said EPO active fragment has a half-life greater than native human EPO.

20. The method of claim 14, wherein said EPO active fragment is hyper-glycosylated compared to native human EPO.

21. The method of claim 14, further comprising contacting said neuronal cells with soluble EPO receptor.

22. The method of claim 14, wherein said IGF is IGF-I.

23. The method of claim 22, wherein said IGF-I is human IGF-I.

24. The method of claim 14, wherein said IGF has at least 10-fold higher affinity for the IGF-I receptor than native human IGF-I.

25. The method of claim 14, wherein said IGF active fragment has an altered affinity for an IGF-binding protein (IBP).

26. The method of claim 14, wherein said IGF has a half-life greater than native human IGF.

27. A method of providing neuroprotection from NMDA receptor-mediated excitatory insult, comprising:
(a) contacting neuronal cells in vitro with erythropoietin (EPO) close to or subsequent to the time of excitatory insult; and
(b) contacting said neuronal cells with an active fragment of insulin-like growth factor (IGF) close to or subsequent to the time of excitatory insult,
thereby producing a synergistic neuroprotective effect from NMDA receptor-mediated excitatory insult in said neuronal cells.

28. The method of claim 27, wherein said EPO is human EPO.

29. The method of claim 27, wherein said EPO has at least 10-fold higher affinity for the EPO receptor than native human EPO.

30. The method of claim 27, wherein said EPO is oligomeric.

31. The method of claim 30, wherein said oligomeric EPO is dimeric.

32. The method of claim 27, wherein said EPO has a half life greater than native human EPO.

33. The method of claim 27, wherein said EPO is hyper-glycosylated compared to native human EPO.

34. The method of claim 27, further comprising contacting said neuronal cells with soluble EPO receptor.

35. The method of claim 27, wherein said IGF active fragment is an IGF-I active fragment.

36. The method of claim 35, wherein said IGF-I active fragment is an active fragment of human IGF-I.

37. The method of claim 27, wherein said IGF active fragment has at least 10-fold higher affinity for the IGF-I receptor than native human IGF-I.

38. The method of claim 27, wherein said IGF active fragment has an altered affinity for an IGF-binding protein (IBP).

39. The method of claim 27, wherein said IGF active fragment has a half-life greater than native human IGF.

40. A method of providing neuroprotection from NMDA receptor-mediated excitatory insult, comprising:
(a) contacting neuronal cells in vitro with an active fragment of erythropoietin (EPO) close to or subsequent to the time of excitatory insult; and
(b) contacting said neuronal cells with an active fragment of insulin-like growth factor (IGF) close to or subsequent to the time of excitatory insult,
thereby producing a synergistic neuroprotective effect from NMDA receptor-mediated excitatory insult in said neuronal cells.

41. The method of claim 40, wherein said EPO active fragment is an active fragment of human EPO.

42. The method of claim 40, wherein said EPO active fragment has at least 10-fold higher affinity for the EPO receptor than native human EPO.

43. The method of claim 40, wherein said EPO active fragment is oligomeric.

44. The method of claim 43, wherein said oligomeric EPO active fragment is dimeric.

45. The method of claim 40, wherein said EPO active fragment has a half-life greater than native human EPO.

46. The method of claim 40, wherein said EPO active fragment is hyper-glycosylated compared to native human EPO.

47. The method of claim 40, further comprising contacting said neuronal cells with soluble EPO receptor.

48. The method of claim 40, wherein said IGF active fragment is an active fragment of IGF-I.

49. The method of claim 48, wherein said IGF-I active fragment is an active fragment of human IGF-I.

50. The method of claim 40, wherein said IGF active fragment has at least 10-fold higher affinity for the IGF-I receptor than native human IGF-I.

51. The method of claim 40, wherein said IGF active fragment has an altered affinity for an IGF-binding protein (IBP).

52. The method of claim 40, wherein said IGF active fragment has a half-life greater than native human IGF.

53. A method of providing neuroprotection from NMDA receptor-mediated excitatory insult, comprising:
(a) contacting neuronal cells in vitro with erythropoietin (EPO) close to or subsequent to the time of excitatory insult; and
(b) contacting said neuronal cells with an insulin-like growth factor (IGF) peptide analog close to or subsequent to the time of excitatory insult, wherein said IGF peptide analog is selected from SEQ ID NOS:13-20,
thereby producing a synergistic neuroprotective effect from NMDA receptor-mediated excitatory insult in said neuronal cells.

54. The method of claim 53, wherein said EPO is human EPO.

55. The method of claim 53, wherein said EPO has at least 10-fold higher affinity for the EPO receptor than native human EPO.

56. The method of claim 53, wherein said EPO is oligomeric.

57. The method of claim 56, wherein said oligomeric EPO is dimeric.

58. The method of claim 53, wherein said EPO has a half-life greater than native human EPO.

59. The method of claim 53, wherein said EPO is hyper-glycosylated compared to native human EPO.

60. The method of claim 53, further comprising contacting said neuronal cells with soluble EPO receptor.

61. A method of providing neuroprotection from NMDA receptor-mediated excitatory insult, comprising:
   (a) contacting neuronal cells in vitro with an active fragment of erythropoietin (EPO) close to or subsequent to the time of excitatory insult; and
   (b) contacting said neuronal cells with an insulin-like growth factor (IGF) peptide analog close to or subsequent to the time of excitatory insult, wherein said IGF peptide analog is selected from SEQ ID NOS:13-20,
   thereby producing a synergistic neuroprotective effect from NMDA receptor-mediated excitatory insult in said neuronal cells.

62. The method of claim 61, wherein said EPO active fragment is an active fragment of human EPO.

63. The method of claim 61, wherein said EPO active fragment has at least 10-fold higher affinity for the EPO receptor than native human EPO.

64. The method of claim 61, wherein said EPO active fragment is oligomeric.

65. The method of claim 64, wherein said oligomeric EPO active fragment is dimeric.

66. The method of claim 61, wherein said EPO active fragment has a half-life greater than native human EPO.

67. The method of claim 61, wherein said EPO active fragment is hyper-glycosylated compared to native human EPO.

68. The method of claim 61, further comprising contacting said neuronal cells with soluble EPO receptor.

* * * * *

SEQUENCE LISTING

```
<160> NUMBER OF SEQ ID NOS: 20

<210> SEQ ID NO 1
<211> LENGTH: 1342
<212> TYPE: DNA
<213> ORGANISM: Homo sapiens
<220> FEATURE:
<221> NAME/KEY: CDS
<222> LOCATION: (182)...(763)

<400> SEQUENCE: 1
cccggagccg gaccggggcc accgcgcccg ctctgctccg acaccgcgcc ccctggacag      60
ccgccctctc ctccaggccc gtggggctgg ccctgcaccg ccgagcttcc cgggatgagg     120
gcccccggtg tggtcacccg gcgcgcccca ggtcgctgag ggacccggc caggcgcgga     180 g atg ggg gtg cac gaa tgt cct gcc tgg ctg tgg ctt ctc ctg tcc ctg     229
  Met Gly Val His Glu Cys Pro Ala Trp Leu Trp Leu Leu Leu Ser Leu
  1               5                  10                  15 ctg tcg ctc cct ctg ggc ctc cca gtc ctg ggc gcc cca cca cgc ctc        277
Leu Ser Leu Pro Leu Gly Leu Pro Val Leu Gly Ala Pro Pro Arg Leu
            20                  25                  30 atc tgt gac agc cga gtc ctg gag agg tac ctc ttg gag gcc aag gag        325
Ile Cys Asp Ser Arg Val Leu Glu Arg Tyr Leu Leu Glu Ala Lys Glu
        35                  40                  45 gcc gag aat atc acg acg ggc tgt gct gaa cac tgc agc ttg aat gag        373
Ala Glu Asn Ile Thr Thr Gly Cys Ala Glu His Cys Ser Leu Asn Glu
    50                  55                  60 aat atc act gtc cca gac acc aaa gtt aat ttc tat gcc tgg aag agg        421
Asn Ile Thr Val Pro Asp Thr Lys Val Asn Phe Tyr Ala Trp Lys Arg
65                  70                  75                  80 atg gag gtc ggg cag cag gcc gta gaa gtc tgg cag ggc ctg gcc ctg        469
Met Glu Val Gly Gln Gln Ala Val Glu Val Trp Gln Gly Leu Ala Leu
                85                  90                  95 ctg tcg gaa gct gtc ctg cgg ggc cag gcc ctg ttg gtc aac tct tcc        517
Leu Ser Glu Ala Val Leu Arg Gly Gln Ala Leu Leu Val Asn Ser Ser
```

-continued

```
                         100                 105                 110
cag ccg tgg gag ccc ctg cag ctg cat gtg gat aaa gcc gtc agt ggc    565
Gln Pro Trp Glu Pro Leu Gln Leu His Val Asp Lys Ala Val Ser Gly
        115                 120                 125 ctt cgc agc ctc acc act ctg ctt cgg gct ctg cga gcc cag aag gaa    613
Leu Arg Ser Leu Thr Thr Leu Leu Arg Ala Leu Arg Ala Gln Lys Glu
130                 135                 140 gcc atc tcc cct cca gat gcg gcc tca gct gct cca ctc cga aca atc    661
Ala Ile Ser Pro Pro Asp Ala Ala Ser Ala Ala Pro Leu Arg Thr Ile
145                 150                 155                 160 act gct gac act ttc cgc aaa ctc ttc cga gtc tac tcc aat ttc ctc    709
Thr Ala Asp Thr Phe Arg Lys Leu Phe Arg Val Tyr Ser Asn Phe Leu
                165                 170                 175 cgg gga aag ctg aag ctg tac aca ggg gag gcc tgc agg aca ggg gac    757
Arg Gly Lys Leu Lys Leu Tyr Thr Gly Glu Ala Cys Arg Thr Gly Asp
            180                 185                 190 aga tga ccaggtgtgt ccacctgggc atatccacca cctccctcac caacattgct    813
Arg  * tgtgccacac cctcccccgc cactcctgaa ccccgtcgag gggctctcag ctcagcgcca    873
gcctgtccca tggacactcc agtgccagca atgacatctc aggggccaga ggaactgtcc    933
agagagcaac tctgagatct aaggatgtca cagggccaac ttgagggccc agagcaggaa    993
gcattcagag agcagcttta aactcaggga cagagccatg ctgggaagac gcctgagctc    1053
actcggcacc ctgcaaaatt tgatgccagg acacgctttg gaggcgattt acctgttttc    1113
gcacctacca tcagggacag gatgacctgg agaacttagg tggcaagctg tgacttctcc    1173
aggtctcacg ggcatgggca ctcccttggt ggcaagagcc cccttgacac cggggtggtg    1233
ggaaccatga agacaggatg ggggctggcc tctggctctc atggggtcca agttttgtgt    1293
attcttcaac ctcattgaca agaactgaaa ccaccaaaaa aaaaaaaaa              1342
```

<210> SEQ ID NO 2
<211> LENGTH: 193
<212> TYPE: PRT
<213> ORGANISM: Homo sapiens

<400> SEQUENCE: 2

```
Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Arg Ala Gln Lys Glu
    130                 135                 140

Ala Ile Ser Pro Pro Asp Ala Ala Ser Ala Ala Pro Leu Arg Thr Ile
```

```
                145                 150                 155                 160
Thr Ala Asp Thr Phe Arg Lys Leu Phe Arg Val Tyr Ser Asn Phe Leu
                    165                 170                 175
Arg Gly Lys Leu Lys Leu Tyr Thr Gly Glu Ala Cys Arg Thr Gly Asp
                180                 185                 190
Arg

<210> SEQ ID NO 3
<211> LENGTH: 166
<212> TYPE: PRT
<213> ORGANISM: Homo sapiens

<400> SEQUENCE: 3

Ala Pro Pro Arg Leu Ile Cys Asp Ser Arg Val Leu Glu Arg Tyr Leu
1               5                   10                  15
Leu Glu Ala Lys Glu Ala Glu Asn Ile Thr Thr Gly Cys Ala Glu His
                20                  25                  30
Cys Ser Leu Asn Glu Asn Ile Thr Val Pro Asp Thr Lys Val Asn Phe
            35                  40                  45
Tyr Ala Trp Lys Arg Met Glu Val Gly Gln Gln Ala Val Glu Val Trp
    50                  55                  60
Gln Gly Leu Ala Leu Leu Ser Glu Ala Val Leu Arg Gly Gln Ala Leu
65                  70                  75                  80
Leu Val Asn Ser Ser Gln Pro Trp Glu Pro Leu Gln Leu His Val Asp
                85                  90                  95
Lys Ala Val Ser Gly Leu Arg Ser Leu Thr Thr Leu Leu Arg Ala Leu
                100                 105                 110
Arg Ala Gln Lys Glu Ala Ile Ser Pro Pro Asp Ala Ala Ser Ala Ala
            115                 120                 125
Pro Leu Arg Thr Ile Thr Ala Asp Thr Phe Arg Lys Leu Phe Arg Val
    130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 4
<211> LENGTH: 725
<212> TYPE: DNA
<213> ORGANISM: Homo sapiens
<220> FEATURE:
<221> NAME/KEY: CDS
<222> LOCATION: (12)...(473)

<400> SEQUENCE: 4
cttcagaagc a atg gga aaa atc agc agt ctt cca acc caa tta ttt aag        50
           Met Gly Lys Ile Ser Ser Leu Pro Thr Gln Leu Phe Lys
           1               5                   10 tgc tgc ttt tgt gat ttc ttg aag gtg aag atg cac acc atg tcc tcc        98
Cys Cys Phe Cys Asp Phe Leu Lys Val Lys Met His Thr Met Ser Ser
        15                  20                  25 tcg cat ctc ttc tac ctg gcg ctg tgc ctg ctc acc ttc acc agc tct       146
Ser His Leu Phe Tyr Leu Ala Leu Cys Leu Leu Thr Phe Thr Ser Ser
30                  35                  40                  45 gcc acg gct gga ccg gag acg ctc tgc ggg gct gag ctg gtg gat gct       194
Ala Thr Ala Gly Pro Glu Thr Leu Cys Gly Ala Glu Leu Val Asp Ala
                50                  55                  60 ctt cag ttc gtg tgt gga gac agg ggc ttt tat ttc aac aag ccc aca       242
```

```
Leu Gln Phe Val Cys Gly Asp Arg Gly Phe Tyr Phe Asn Lys Pro Thr
            65                  70                  75 ggg tat ggc tcc agc agt cgg agg gcg cct cag aca ggt atc gtg gat    290
Gly Tyr Gly Ser Ser Ser Arg Arg Ala Pro Gln Thr Gly Ile Val Asp
        80                  85                  90 gag tgc tgc ttc cgg agc tgt gat cta agg agg ctg gag atg tat tgc    338
Glu Cys Cys Phe Arg Ser Cys Asp Leu Arg Arg Leu Glu Met Tyr Cys
    95                 100                 105 gca ccc ctc aag cct gcc aag tca gct cgc tct gtc cgt gcc cag cgc    386
Ala Pro Leu Lys Pro Ala Lys Ser Ala Arg Ser Val Arg Ala Gln Arg
110             115                 120                 125 cac acc gac atg ccc aag acc cag aag gaa gta cat ttg aag aac gca    434
His Thr Asp Met Pro Lys Thr Gln Lys Glu Val His Leu Lys Asn Ala
                130                 135                 140 agt aga ggg agt gca gga aac aag aac tac agg atg tag gaagaccctc    483
Ser Arg Gly Ser Ala Gly Asn Lys Asn Tyr Arg Met  *
            145                 150 ctgaggagtg aagagtgaca tgccaccgca ggatcctttg ctctgcacga gttacctgtt    543
aaactttgga acacctacca aaaataagt tgataacat ttaaaagatg gcgtttccc     603 ccaatgaaat acacaagtaa acattccaac attgtcttta ggagtgattt gcaccttgca    663
aaaatggtcc tggagttggt agattgctgt tgatctttta tcaataatgt tctatagaaa    723
ag                                                                  725

<210> SEQ ID NO 5
<211> LENGTH: 153
<212> TYPE: PRT
<213> ORGANISM: Homo sapiens

<400> SEQUENCE: 5

Met Gly Lys Ile Ser Ser Leu Pro Thr Gln Leu Phe Lys Cys Cys Phe
  1               5                  10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Glu Thr Leu Cys Gly Ala Glu Leu Val Asp Ala Leu Gln Phe
        50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150

<210> SEQ ID NO 6
<211> LENGTH: 70
<212> TYPE: PRT
<213> ORGANISM: Homo sapiens

<400> SEQUENCE: 6
```

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65              70

<210> SEQ ID NO 7
<211> LENGTH: 20
<212> TYPE: PRT
<213> ORGANISM: Artificial Sequence
<220> FEATURE:
<223> OTHER INFORMATION: synthetic construct

<400> SEQUENCE: 7

Gly Gly Thr Tyr Ser Cys His Phe Gly Pro Leu Thr Trp Val Cys Lys
1               5                   10                  15

Pro Gln Gly Gly
            20

<210> SEQ ID NO 8
<211> LENGTH: 20
<212> TYPE: PRT
<213> ORGANISM: Artificial Sequence
<220> FEATURE:
<223> OTHER INFORMATION: synthetic construct

<400> SEQUENCE: 8

Gly Gly Asp Tyr His Cys Arg Met Gly Pro Leu Thr Trp Val Cys Lys
1               5                   10                  15

Pro Leu Gly Gly
            20

<210> SEQ ID NO 9
<211> LENGTH: 20
<212> TYPE: PRT
<213> ORGANISM: Artificial Sequence
<220> FEATURE:
<223> OTHER INFORMATION: synthetic construct

<400> SEQUENCE: 9

Gly Gly Val Tyr Ala Cys Arg Met Gly Pro Ile Thr Trp Val Cys Ser
1               5                   10                  15

Pro Leu Gly Gly
            20

<210> SEQ ID NO 10
<211> LENGTH: 20
<212> TYPE: PRT
<213> ORGANISM: Artificial Sequence
<220> FEATURE:
<223> OTHER INFORMATION: synthetic construct

<400> SEQUENCE: 10

Val Gly Asn Tyr Met Cys His Phe Gly Pro Ile Thr Trp Val Cys Arg
1               5                   10                  15

Pro Gly Gly Gly
            20
```

```
<210> SEQ ID NO 11
<211> LENGTH: 20
<212> TYPE: PRT
<213> ORGANISM: Artificial Sequence
<220> FEATURE:
<223> OTHER INFORMATION: synthetic construct

<400> SEQUENCE: 11

Gly Gly Leu Tyr Leu Cys Arg Phe Gly Pro Val Thr Trp Asp Cys Gly
 1               5                  10                  15

Tyr Lys Gly Gly
            20

<210> SEQ ID NO 12
<211> LENGTH: 14
<212> TYPE: PRT
<213> ORGANISM: Artificial Sequence
<220> FEATURE:
<223> OTHER INFORMATION: synthetic construct

<400> SEQUENCE: 12

Gly Gly Cys Arg Ile Gly Pro Ile Thr Trp Val Cys Gly Gly
 1               5                  10

<210> SEQ ID NO 13
<211> LENGTH: 20
<212> TYPE: PRT
<213> ORGANISM: Artificial Sequence
<220> FEATURE:
<223> OTHER INFORMATION: synthetic construct

<400> SEQUENCE: 13

Ala Ser Glu Glu Val Cys Trp Pro Val Ala Glu Trp Tyr Leu Cys Asn
 1               5                  10                  15

Met Trp Gly Arg
            20

<210> SEQ ID NO 14
<211> LENGTH: 15
<212> TYPE: PRT
<213> ORGANISM: Artificial Sequence
<220> FEATURE:
<223> OTHER INFORMATION: synthetic construct

<400> SEQUENCE: 14

Ala Ser Glu Glu Val Cys Trp Pro Val Ala Glu Trp Tyr Leu Cys
 1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: synthetic construct

<400> SEQUENCE: 15

Gly Pro Glu Thr Cys Trp Pro Val Ala Glu Trp Tyr Leu Cys Asn
 1               5                  10                  15

<210> SEQ ID NO 16
<211> LENGTH: 14
<212> TYPE: PRT
<213> ORGANISM: Artificial Sequence
<220> FEATURE:
<223> OTHER INFORMATION: synthetic construct
```

```
-continued

<400> SEQUENCE: 16

Glu Glu Val Cys Trp Pro Val Ala Glu Trp Tyr Leu Cys Asn
 1               5                  10

<210> SEQ ID NO 17
<211> LENGTH: 13
<212> TYPE: PRT
<213> ORGANISM: Artificial Sequence
<220> FEATURE:
<223> OTHER INFORMATION: synthetic construct

<400> SEQUENCE: 17

Glu Val Cys Trp Pro Val Ala Glu Trp Tyr Leu Cys Asn
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: synthetic construct

<400> SEQUENCE: 18

Cys Trp Pro Val Ala Glu Trp Tyr Leu Cys Asn
 1               5                  10

<210> SEQ ID NO 19
<211> LENGTH: 15
<212> TYPE: PRT
<213> ORGANISM: Artificial Sequence
<220> FEATURE:
<223> OTHER INFORMATION: synthetic construct

<400> SEQUENCE: 19

Cys Arg Ala Gly Pro Leu Gln Trp Leu Cys Glu Lys Tyr Phe Gly
 1               5                  10                  15

<210> SEQ ID NO 20
<211> LENGTH: 19
<212> TYPE: PRT
<213> ORGANISM: Artificial Sequence
<220> FEATURE:
<223> OTHER INFORMATION: synthetic construct

<400> SEQUENCE: 20

Ser Glu Val Gly Cys Arg Ala Gly Pro Leu Gln Trp Leu Cys Glu Lys
 1               5                  10                  15

Tyr Phe Gly
```